US010278647B2

United States Patent
Salehizadeh et al.

(10) Patent No.: US 10,278,647 B2
(45) Date of Patent: *May 7, 2019

(54) METHOD AND APPARATUS FOR REMOVING MOTION ARTIFACTS FROM BIOMEDICAL SIGNALS

(71) Applicant: University of Connecticut, Farmington, CT (US)

(72) Inventors: Seyed M. A. Salehizadeh, Coventry, CT (US); Ki H. Chon, Mansfield Center, CT (US); Yeonsik Noh, Willington, CT (US)

(73) Assignee: University of Connecticut, Farmington, CT (US)

( * ) Notice: Subject to any disclaimer, the term of this patent is extended or adjusted under 35 U.S.C. 154(b) by 229 days.

This patent is subject to a terminal disclaimer.

(21) Appl. No.: 15/178,089

(22) Filed: Jun. 9, 2016

(65) Prior Publication Data

US 2016/0361021 A1 Dec. 15, 2016

Related U.S. Application Data

(60) Provisional application No. 62/299,944, filed on Feb. 25, 2016, provisional application No. 62/172,862, filed on Jun. 9, 2015.

(51) Int. Cl.
*A61B 5/00* (2006.01)
*A61B 5/0205* (2006.01)
(Continued)

(52) U.S. Cl.
CPC ............ *A61B 5/721* (2013.01); *A61B 5/0205* (2013.01); *A61B 5/0245* (2013.01);
(Continued)

(58) Field of Classification Search
None
See application file for complete search history.

(56) References Cited

U.S. PATENT DOCUMENTS

| 4,938,228 A | 7/1990 | Righter et al. |
| 5,609,158 A | 3/1997 | Chan |

(Continued)

FOREIGN PATENT DOCUMENTS

| EP | 1 297 784 A1 | 4/2003 |
| EP | 1 724 684 | 11/2006 |

(Continued)

OTHER PUBLICATIONS

Notification and Transmittal of International Search Report and Written Opinion dated Mar. 16, 2017, for International Appl. No. PCT/US2016/036734, entitled "Method and Apparatus for Removing Motion Artifacts From Biomedical Signals", consisting of 17 pages.

(Continued)

*Primary Examiner* — Brian T Gedeon
(74) *Attorney, Agent, or Firm* — Hamilton, Brook, Smith & Reynolds, P.C.

(57) ABSTRACT

A method and corresponding apparatus employ a time-varying spectral analysis approach for reconstructing a heart-related signal that includes motion artifacts. The motion artifacts are produced by motion of a biomedical sensor relative to a sensing location. By comparing time-varying spectra of the heart-related signal and a motion signal, those frequency peaks resulting from the motion artifacts may be suppressed in a time-varying spectrum of the heart-related signal. The time-varying spectral analysis based approach enables the heart-related signal to be reconstructed with accuracy by suppressing the motion artifacts. Example applications for the method and corresponding (Continued)

apparatus include training aids (e.g., runners' heart-rate monitors) and hospital patient heart-rate monitors.

75 Claims, 28 Drawing Sheets

(51) Int. Cl.
```
A61B 5/024      (2006.01)
A61B 5/0245     (2006.01)
A61B 5/04       (2006.01)
A61B 5/11       (2006.01)
A61B 5/1455     (2006.01)
A61B 5/046      (2006.01)
A61B 5/0464     (2006.01)
```
(52) U.S. Cl.
CPC ...... *A61B 5/02416* (2013.01); *A61B 5/02427* (2013.01); *A61B 5/02438* (2013.01); *A61B 5/04012* (2013.01); *A61B 5/725* (2013.01); *A61B 5/7239* (2013.01); *A61B 5/7253* (2013.01); *A61B 5/0077* (2013.01); *A61B 5/02405* (2013.01); *A61B 5/046* (2013.01); *A61B 5/0464* (2013.01); *A61B 5/1102* (2013.01); *A61B 5/14552* (2013.01); *A61B 5/6824* (2013.01); *A61B 5/7275* (2013.01); *A61B 2503/10* (2013.01); *A61B 2505/07* (2013.01); *A61B 2505/09* (2013.01); *A61B 2562/0219* (2013.01)

(56) References Cited

U.S. PATENT DOCUMENTS

| | | | |
|---|---|---|---|
| 8,388,543 | B2 | 3/2013 | Chon et al. |
| 8,417,326 | B2 | 4/2013 | Chon et al. |
| 8,945,017 | B2* | 2/2015 | Venkatraman ......... A61B 5/721 600/500 |
| 8,998,815 | B2 | 4/2015 | Venkatraman et al. |
| 9,713,428 | B2* | 7/2017 | Chon ................ A61B 5/02405 |
| 9,872,652 | B2 | 1/2018 | Salehizadeh et al. |
| 2008/0109041 | A1 | 5/2008 | de Voir |
| 2008/0167564 | A1 | 7/2008 | Hete et al. |
| 2009/0069703 | A1 | 3/2009 | Takla et al. |
| 2011/0066041 | A1 | 3/2011 | Pandia et al. |
| 2012/0123232 | A1 | 5/2012 | Najarian et al. |
| 2014/0005988 | A1 | 1/2014 | Brockway |
| 2014/0222350 | A1 | 8/2014 | Zheng et al. |
| 2014/0275852 | A1 | 9/2014 | Hong et al. |
| 2014/0275854 | A1 | 9/2014 | Venkatraman et al. |
| 2014/0309943 | A1* | 10/2014 | Grundlehner ......... G06F 19/321 702/19 |
| 2016/0360977 | A1 | 12/2016 | Salehizadeh et al. |

FOREIGN PATENT DOCUMENTS

| | | |
|---|---|---|
| EP | 1 757 224 A2 | 2/2007 |
| EP | 2 792 297 | 10/2014 |
| WO | WO 03/000125 | 1/2003 |
| WO | WO 2011/026669 A1 | 3/2011 |
| WO | WO 2012/100175 | 7/2012 |
| WO | WO 2012/123828 A1 | 9/2012 |
| WO | WO 2016/201130 | 12/2016 |
| WO | WO 2017/019184 A2 | 2/2017 |
| WO | WO 2017019184 A2 | 2/2017 |

OTHER PUBLICATIONS

2015 IEEE Signal Processing Cup. Available online: / http://www.zhilinzhang.com/spcup2015/.

Boreom Lee, et al., "Improved Elimination of Motion Artifacts From a Photoplethysmographic Signal Using a Kalman Smoother With Simultaneous Accelerometry," *Physiological Measurement*, 31(12):1585 (2010).

Salehizadeh, S., et al., "Photoplethysmograph Signal Reconstruction Based on a Novel Motion Artifact Detection-Reduction Approach. Part II: Motion and Noise Artifact Removal," *Ann. Biomed. Eng.*, 42:2251-2263 (2014).

Dash S., Chon, K.H. Raeder E. "Automatic real time detection of atrial fibrillation", Ann Biomed Eng, Sep. 2009;37(9):1701-9.

Dash, S., et al., "Estimation of Respiratory Rate From ECG, Photoplethysmogram, and Piezoelectric Pulse Transducer Signals: A Comparative Study of Time– Frequency Methods," *Biomedical Engineering, IEEE Transactions on*, 57(5):1099-1107 (2010).

Deepak Vala , D.T.P., "A Survey on Ambulatory ECG and Identification of Motion Artifact," *International Journal of Engineering Research and Development*, 1(7):38-41 (2012).

Devlin PH, M.R., and Ketchum, J.W., "Detection Electrode Motion Noise in ECG Signals by Monitoring Electrode Impedance," *Computers in Cardiology*, p. 51-56 (1984).

Hamilton, P.S., et al., "Comparison of Methods for Adaptive Removal of Motion Artifact," *Computers in Cardiology*, 2000 (2000).

Hamilton, P.S., et al., "Effect of Adaptive Motion-Artifact Reduction on QRS Detection," *Biomed Instrum. Technol.*, 34(3):197-202 (2000).

Hashim, F.R., et al., "Wavelet Based Motion Artifact Removal for ECG Signals," In: IEEE EMBS International on Biomedical Engineering and Sciences (IECBES). Langkawi: IEEE: 2012, 339-342.

Hyvärinen, A. and Oja, E., "Independent Component Analysis: Algorithms and Applications," *Neural Networks*, 13(4-5):411-430 (2000).

Jinseok, L., et al., "Automatic Motion and Noise Artifact Detection in Holter ECG Data Using Empirical Mode Decomposition and Statistical Approaches,"*Biomedical Engineering, IEEE Transactions on*, 59(6):1499-1506 (2012).

Kalman, R.E., "A New Approach to Linear Filtering and Prediction Problems," *Trans. ASME J. Basic Eng.*, 82:35-45 (1960).

Kearney, K., et al ., "Quantification of Motion Artifact in ECG Electrode Design," *Engineering in Medicine and Biology Society, EMBS 2007. 29th Annual International Conference of the IEEE*, (2007).

Kim, B.S. and Yoo, S.K., "Motion Artifact Reduction in Photoplethysmography Using Independent Component Analysis," *IEEE Trans. Biomed Eng.*,53:566-568 (2006).

Krishnan, R., B., et al., "Two-Stage Approach for Detection and Reduction of Motion Artifacts in Photoplethysmographic Data," *Biomedical Engineering, IEEE Transactions on*, 57(8):1867-1876 (2010).

Maeda, Y., et al., "Relationship Between Measurement Site and Motion Artifacts in Wearable Reflected Photoplethysmography," *J Med Syst*, 35(5):969-76 (2011).

Rahman, M.Z.U., et al., "An Efficient Noise Cancellation Technique to Remove Noise From the ECG Signal Using Normalized Signed Regressor LMS Algorithm," *Bioinformatics and Biomedicine, BIBM '09, IEEE International Conference on* (2009). 257-260.

Raya, M.A.D. and Sison, L.G., "Adaptive Noise Cancelling of Motion Artifact in Stress ECG Signals Using Accelerometer," *Engineering in Medicine and Biology, 24th Annual Conference and the Annual Fall Meeting of the Biomedical Engineering Society EMBS/BMES Conference, Proceedings of the Second Joint* (2002). 1756-1757.

Reyes, B.A., et al., "Novel Electrodes for Underwater ECG Monitoring," *IEEE Trans Biomed Eng.*, 61(6):1863-76 (2014).

Salehizadeh, S., et al., "A Novel Time-Varying Spectral Filtering Algorithm for Reconstruction of Motion Artifact Corrupted Heart Rate Signals During Intense Physical Activities Using a Wearable Photoplethysmogram Sensor," *Sensors*, 16(1):10 (2016).

Sarmiento, S., et al., "Heart Rate Variability During High-Intensity Exercise", *Journal of Systems Science and Complexity*, 26(1):104-116 (2013).

Seyedtabaii, S.S.A.L., "Kalman Filter Based Adaptive Reduction of Motion Artifact From Photoplethysmographic Signal," *World Acad. Sci. Eng. Technol.*, 37:136-137 (2008).

Temko, A., "Estimation of Heart Rate From Photoplethysmography During Physical Exercise Using Wiener Filtering and the Phase

(56) References Cited

OTHER PUBLICATIONS

Bocoder," *37th Annual International Conference of the IEEE Engineering in Medicine and Biology Society* (2015).

Thakor, N.V. and Yi-Sheng, Z., "Applications of Adaptive Filtering to ECG Analysis: Noise Cancellation and Arrhythmia Detection," *Biomedical Engineering, IEEE Transactions on*, 38(8):785-794 (1991).

Wang, H., et al., "A High Resolution Approach to Estimating Time-Frequency Spectra and Their Amplitudes," *Annals of Biomedical Engineering*, 34(2):326-338 (2006).

Yao, J. and Warren, S. "A Short Study to Assess the Potential of Independent Component Analysis for Motion Artifact Separation in Wearable Pulse Oximeter Signals," *IEEE Eng. Med. Biol. Soc. ConfProc.*, 4:3585-3588 (2005).

Yilmaz, T., et al., "Detecting Vital Signs With Wearable Wireless Sensors," *Sensors*, 10(12):10837 (2010).

Yoon, H. et al., "An Automated Motion Artifact Removal Algorithm in Electrocardiogram Based on Independent Component Analysis", in *The Fifth International Conference on eHealth, Telemedicine, and Social Medicine*, Nice, France. p. 15-20 (2013).

Zhang, Z., "Photoplethysmography-Based Heart Rate Monitoring in Physical Activities via Joint Sparse Spectrum Reconstruction," *Biomedical Engineering, IEEE Transactions* PP(99):1,1 (2015).

Zhang, Z., et al., "TROIKA: A General Framework for Heart Rate Monitoring Using Wrist-Type Photoplethysmographic Signals During Intensive Physical Exercise," *IEEE Trans. on Biomedical Engineering*, 62(2):522-531 (2015).

Zhang, et al., "Novel QRS Detection by CWT for ECG Sensor," *Biomedical Circuits and Systems Conference* pp. 211-214 (2007).

\* cited by examiner

ACTUAL ERROR IS 2.8557 AND VFCDM ERROR IS 1.1013

TIME (MIN)

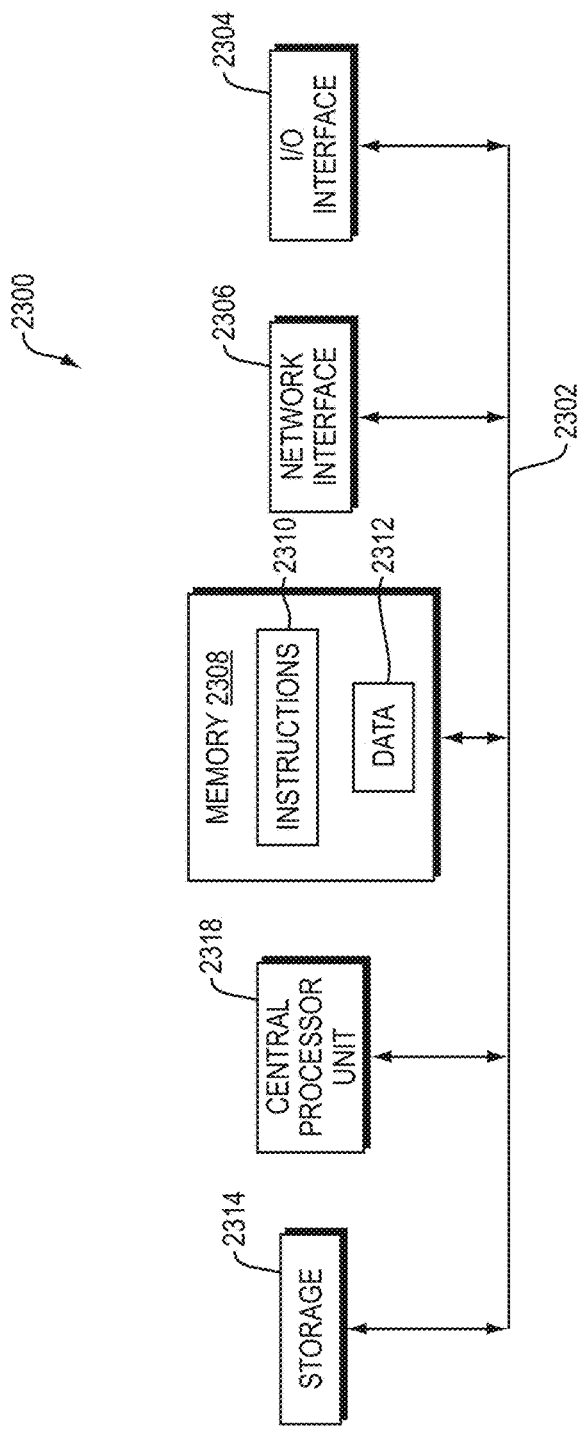

METHOD AND APPARATUS FOR REMOVING MOTION ARTIFACTS FROM BIOMEDICAL SIGNALS

RELATED APPLICATIONS

This application claims the benefit of U.S. Provisional Application No. 62/172,862 filed Jun. 9, 2015 and U.S. Provisional Application No. 62/299,944 filed Feb. 25, 2016. The entire teachings of the above applications are incorporated herein by reference.

GOVERNMENT SUPPORT

This invention was made with government support under Grant No. W81XWH-12-1-0541 from the US Army Medical Research and Material Command (USAMRMC). The government has certain rights in the invention.

BACKGROUND

Heart rate monitors have become widely-used training aids for a variety of sports. Some heart rate monitors use sensors based on photoplethysmography (PPG) technology. The PPG sensors include infrared light-emitting diodes (LEDs) and photodetectors, and offer a simple, reliable, low-cost means of monitoring pulse rate noninvasively, both at rest and during exercise.

SUMMARY

During exercise and other activities, PPG and other sensors may experience movement, such as shifting position or rotating, relative to a sensing location (e.g., wrist or finger) The movement typically results in an introduction of a motion artifact in an electrical signal produced by the sensor. The motion artifact may be interpreted by a processor as a heart-related signal if not addressed in advance of or as part of the processing in the processor. By properly addressing the motion artifact, an embodiment disclosed herein has improved accuracy in reconstructing the heart-related signal, thereby enabling processes that use the heart-related signal to have better performance.

Accordingly, a method for reconstructing a heart-related signal output by a biomedical sensor may comprise reconstructing a representation of the heart-related signal to produce a reconstructed representation of the heart-related signal. The reconstructing may be based on (i) a time-varying spectral analysis of the heart-related signal and a motion signal, the motion signal output by a motion sensor and representative of motion artifacts in the heart-related signal, the motion artifacts being signal artifacts produced by movement of the biomedical sensor relative to a sensing location, and the classification of the movement may be based on (ii) a classification of the movement. The method may further comprise outputting the reconstructed representation of the heart-related signal.

The motion artifacts may be suppressed in the reconstructed representation of the heart-related signal.

The time-varying spectral analysis may include pre-processing the heart-related signal to produce a pre-processed heart-related signal. In an event the classification indicates that the movement does not rise to a level causing the motion artifacts, the reconstructed representation may be based on an average value of peak-to-peak intervals in the pre-processed heart-related signal.

The pre-processing may include filtering the heart-related signal to produce a filtered heart-related signal.

The pre-processing may further include down-sampling the filtered heart-related signal, the down-sampling being at a sampling rate less than an original sampling rate.

The time-varying spectral analysis may include computing a first time-frequency spectrum (TFS) of the heart-related signal and computing a second TFS of the motion signal.

The first TFS computed and the second TFS computed may be 3-dimensional spectra, the first TFS computed and the second TFS computed each including a respective time-varying amplitude or power distribution with respect to time and frequency.

The first TFS computed may be a first time-varying power spectral density (PSD) and the second TFS computed may be a second time-varying PSD.

The reconstructed representation may be a current reconstructed representation. Based on the classification indicating that the movement does rise to a level causing the motion artifacts and is a pseudo-periodic movement or a periodic movement, the reconstructing may include determining whether at least one spectral peak is present having a corresponding frequency within a given frequency range at a point in time in the first TFS computed, the current reconstructed representation being reconstructed for the point in time. Based on a determination that the at least one spectral peak is not present, the current reconstructed representation may be based on a prior reconstructed representation, the prior reconstructed representation associated with a previous point in time in the first TFS computed. The given frequency range may be 0.5 Hz to 3 Hz.

The reconstructing may include retaining up to a predetermined number of candidate spectral peaks located at a first point in time in the first TFS computed. The candidate spectral peaks retained may be based on having corresponding frequencies within a given frequency range and highest amplitude or power values relative to other spectral peaks located at the first point in time, the other spectral peaks having respective frequencies within the given frequency range. The reconstructing may further include discarding each of the candidate spectral peaks retained that is associated with a same frequency as a dominant spectral peak located at a second point in time in the second TFS computed. The first point in time and the second point time may have same time values. The given frequency range may be 0.5 Hz to 3 Hz.

The representation may be a current representation and the reconstructed representation may be a current reconstructed representation. In an event the discarding discards each of the candidate spectral peaks retained, reconstructing the current representation may be based on a prior reconstructed representation, the prior reconstructed representation associated with a previous point in time in the first TFS computed, the previous point in time being an earlier point in time with respect to the first point in time.

The discarding may be a first discarding, the representation may be a current representation and, in an event the first discarding results in at least one remaining candidate spectral peak retained, reconstructing the current representation may further include second discarding. The second discarding may discard remaining candidate spectral peaks, of the at least one remaining candidate spectral peak retained, based on whether a corresponding frequency of the at least one remaining candidate spectral peak retained is distanced by at least a frequency difference threshold from a prior reconstructed representation's frequency. The prior reconstructed representation associated with a previous point in time in the first TFS computed. The previous point in time may be an earlier point in time with respect to the first point in time.

Based on each of the at least one remaining candidate spectral peak retained having been discarded by the second discarding, reconstructing the current representation may be based on the prior reconstructed representation. Based on at least one last candidate spectral peak remaining, the at least one last candidate spectral peak remaining not discarded by the second discarding, reconstructing the current representation may be based on a selected candidate spectral peak. The selected candidate spectral peak may be selected from amongst the at least one last candidate spectral peak remaining having a closest corresponding frequency to the prior reconstructed representation's frequency relative to respective frequencies of each of the at least one last candidate spectral peak remaining.

The dominant spectral peak may have a largest power or amplitude value relative to other peaks located at the second point in time in the second TFS.

The retaining and the discarding may be based on the classification indicating that the movement is a pseudo-periodic movement or a periodic movement, and determining that at least one spectral peak with a corresponding frequency in the given frequency range is present at the first point in time.

The time-varying spectral analysis may further include pre-processing the heart-related signal and the motion signal for the computing of the first TFS and the second TFS.

The pre-processing may include filtering the heart-related signal and the motion signal to produce a filtered heart-related signal and a filtered motion signal, respectively. The pre-processing may further include down-sampling both the filtered heart-related signal and the filtered motion signal, the down-sampling being at a sampling rate less than an original sampling rate.

The method may further include classifying the classification of the movement by comparing an amount of amplitude modulation in the second TFS computed to an amplitude modulation threshold. The amplitude modulation threshold may be dependent on a type of the motion detector sensor. The classification may indicate whether the movement rises to a level causing the motion artifacts based on a result of the comparing. In an event the result indicates that the movement does rise to the level causing the motion artifacts, classifying the classification of the movement may further include determining whether the movement is either a pseudo-periodic movement or a periodic movement, versus a random movement.

In determining whether the movement is either the pseudo-periodic movement or the periodic movement, versus the random movement, the method may further include identifying a first, second, and third frequency associated, respectively, with a first, second, and third spectral peak in the second TFS at a point in time in the second TFS. The first, second, and third peaks may have largest power or amplitude values relative to other peaks in the second TFS at the point in time. The first spectral peak may be a largest spectral peak amongst the first, second, and third spectral peaks.

In determining whether the movement is either the pseudo-periodic movement or the periodic movement, versus the random movement, the method may further include computing a first ratio of the second frequency identified to the first frequency identified. The method may determine a first comparison result by comparing the first ratio computed to a first ratio value. The method may compute a second ratio of the third frequency identified to the first frequency identified. The method may determine a second comparison result by comparing the second ratio computed to a second ratio value. The classification may further indicate the movement is either the pseudo-periodic movement or the periodic movement, versus the random movement, based on the first comparison result and the second comparison result. The first ratio value may be 2 and the second ratio value may be 3.

The time-varying signal analysis may include pre-processing the heart-related signal to produce a pre-processed heart-related signal and, in an event the classification of the movement indicates the random movement, the reconstructing may include computing an average value of a number of prior reconstructed representations outputted prior to the reconstructing. The number may be based on a duration of consecutive motion artifacts, detected prior to the reconstructing. The time-varying signal analysis may further include computing a bandpass filter cutoff frequency based on the average value computed, and filtering the pre-processed heart-rate signal by applying the band pass filter computed to produce a filtered, pre-processed heart-related signal. The reconstructed representation may be based on an average peak-to-peak interval value of the filtered, pre-processed heart-rate signal.

The heart-related signal and the motion signal may be produced, concurrently.

The method may comprise segmenting the heart-related signal into a plurality of windowed heart-related signal data segments and segmenting the motion signal into a corresponding plurality of windowed motion signal data segments. The method may comprise repeating the reconstructing and the outputting for each windowed heart-related signal data segment and each corresponding motion signal data segment. The time window may be a value in a range from 2 to 32 seconds.

The biomedical sensor may be at least one of: a photoplethysmogram (PPG) sensor, piezoelectric sensor, Light Emitting Diode (LED) based sensor, camera sensor, and pulse oximeter sensor, and the motion sensor may be an accelerometer.

The biomedical sensor and the motion sensor may be co-located.

The method may further comprise employing the reconstructed representation to determine a heart rate estimate.

The method may further comprise employing the reconstructed representation to determine an arterial oxygen saturation (SpO2) estimate.

The method may further comprise employing the reconstructed representation to detect or predict a heart-related ailment. The heart-related ailment may include at least one of a heart rate variability (HRV) condition, atrial fibrillation condition, congestive heart failure condition, and tachycardia condition.

The reconstructing and the outputting may be performed in real-time with respect to production of the heart-related signal and the motion signal.

The reconstructing and the outputting may be performed in non-real-time with respect to production of the heart-related signal and the motion signal.

According to another embodiment, an apparatus for reconstructing a heart-related signal output by a biomedical sensor may comprise a reconstruction unit. The reconstruction unit may be configured to reconstruct a representation of the heart-related signal to produce a reconstructed representation of the heart-related signal, the reconstructing based on (i) a time-varying spectral analysis of the heart-related signal and a motion signal, the motion signal output by a motion sensor and representative of motion artifacts in the heart-related signal, the motion artifacts being signal artifacts produced by movement of the biomedical sensor relative to a sensing location, and (ii) a classification of the movement. The apparatus may further comprise an output unit configured to output the reconstructed representation of the heart-related signal.

Yet another example embodiment may include a non-transitory computer-readable medium having stored thereon a sequence of instructions which, when loaded and executed by a processor, causes the processor to complete methods disclosed herein.

It should be understood that embodiments disclosed herein can be implemented in the form of a method, apparatus, system, or computer readable medium with program codes embodied thereon.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 23 is a block diagram of an example internal structure of a computer optionally within an embodiment disclosed herein.

DETAILED DESCRIPTION

Figure 1:
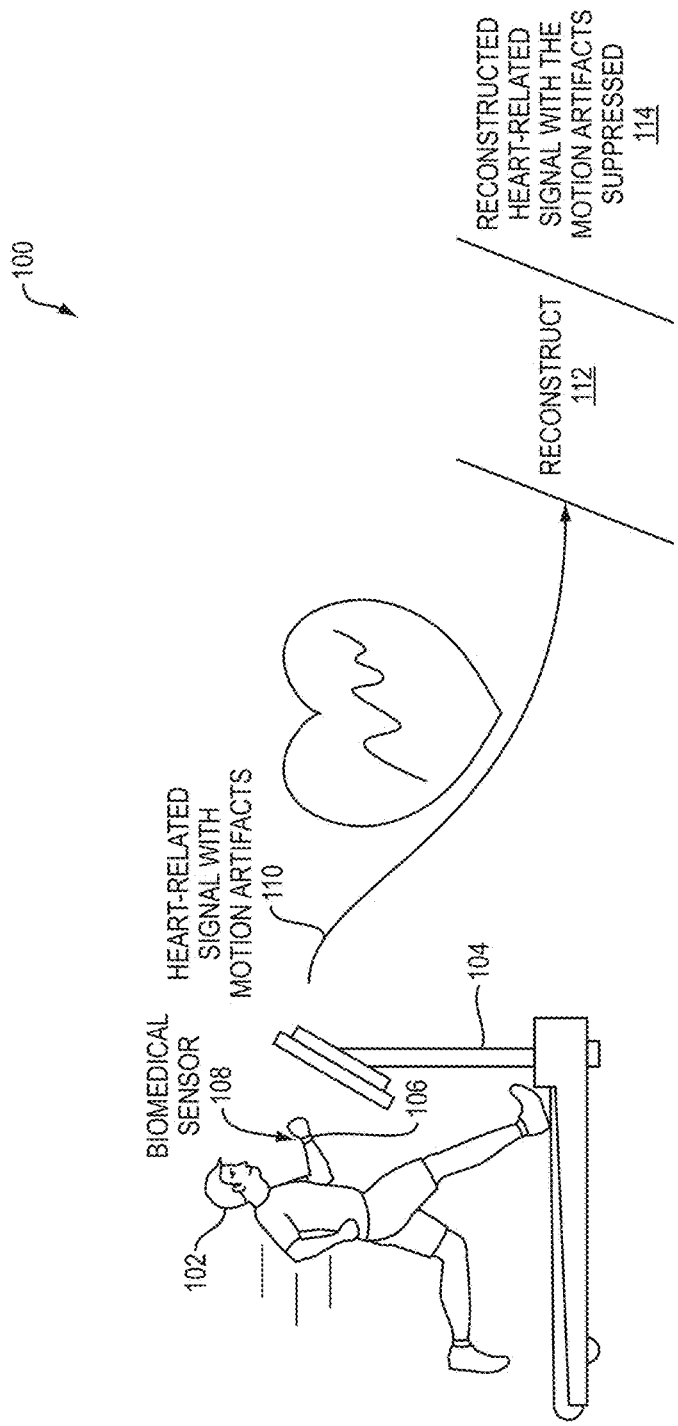
FIG. 1 is a block diagram of an example application for which embodiments disclosed herein may be applied.

A description of example embodiments of the invention follows.

Accurate estimation of a heart rate (HR) and changing arterial oxygen saturation (SpO2) from a heart-related signal, such as a photoplethysmogram (PPG) signal, during intense physical activity is a very challenging problem. This is because strenuous and high intensity exercise can result in severe motion artifacts (MAs) in the heart-related signal, making accurate HR and SpO2 estimation difficult.

HR monitoring using PPG signals has many advantages compared to using traditional ECG sensors, such as simpler hardware implementation, lower cost, and no need for daily application of electrodes (Salehizadeh, S. M. A., et al., Photoplethysmograph Signal Reconstruction based on a Novel Motion Artifact Detection-Reduction Approach. Part II: Motion and Noise Artifact Removal. Annals of Biomedical Engineering, 2014. 42(11): p. 2251-2263). Fluctuations of the PPG signal are caused by changes in arterial blood volume associated with each heartbeat, where the magnitude of the fluctuations depends on the amount of blood rushing into the peripheral vascular bed, the optical absorption of the blood, skin, and tissue, and the wavelength used to illuminate the blood. The pulse oximeter signal contains not only the blood oxygen saturation and heart rate (HR) data, but also other vital physiological information (Chon, K. H., S. Dash, and J. Kihwan, Estimation of Respiratory Rate From Photoplethysmogram Data Using Time-Frequency Spectral Estimation. Biomedical Engineering, IEEE Transactions on, 2009. 56(8): p. 2054-2063; Lee, J. and K. H. Chon, Respiratory Rate Extraction Via an Autoregressive Model Using the Optimal Parameter Search Criterion. Annals of Biomedical Engineering, 2010. 38(10): p. 3218-3225; Dash, S., et al., Estimation of Respiratory Rate From ECG, Photoplethysmogram, and Piezoelectric Pulse Transducer Signals: A Comparative Study of Time-Frequency Methods. Biomedical Engineering, IEEE Transactions on, 2010. 57(5): p.

1099-1107; Jinseok, L. and K. H. Chon, Time-Varying Autoregressive Model-Based Multiple Modes Particle Filtering Algorithm for Respiratory Rate Extraction From Pulse Oximeter. Biomedical Engineering, IEEE Transactions on, 2011. 58(3): p. 790-794). The fluctuations of PPG signals contain the influences of arterial, venous, autonomic and respiratory systems on the peripheral circulation. Utilizing a pulse oximeter as a multi-purpose vital sign monitor has clinical appeal, since it is familiar to the clinician and comfortable for the patient (Salehizadeh, S. M. A., et al., Photoplethysmograph Signal Reconstruction based on a Novel Motion Artifact Detection-Reduction Approach. Part II: Motion and Noise Artifact Removal. Annals of Biomedical Engineering, 2014. 42(11): p. 2251-2263). Even simple knowledge of HR patterns would provide more useful clinical information than just HR and blood oxygenation, especially in situations in which a pulse oximeter is the sole monitor available. One major example of such benefits can be seen in a study by Chong et al. which shows that accurate detection of atrial fibrillation can be obtained from PPG data (Jo Woon, C., et al., Arrhythmia Discrimination Using a Smart Phone. Biomedical and Health Informatics, IEEE Journal of, 2015. 19(3): p. 815-824). In addition to the acquisition of HR in response to exercise, research has recently focused on obtaining HRV information from wearable sensors including devices that use PPGs (Achten, J. and A. E. Jeukendrup, Heart rate monitoring: applications and limitations. Sports medicine (Auckland, N.Z.), 2003. 33(7): p. 517-538). Increased HRV has been associated with lower mortality rates and is affected by both age and sex (Achten, J. and A. E. Jeukendrup, Heart rate monitoring: applications and limitations. Sports medicine (Auckland, N.Z.), 2003. 33(7): p. 517-538). During graded exercise, the majority of studies show that HRV decreases progressively up to moderate intensities, after which it stabilizes (Laughlin, M. H., Cardiovascular response to exercise. Am J Physiol, 1999. 277(6 Pt 2): p. S244-59). Although there are many promising and attractive features of using pulse oximeters for vital sign monitoring, currently they are mainly used on stationary patients. This is because motion artifacts (MAs) result in unreliable HR and $SpO_2$ estimation (Salehizadeh, S. M. A., et al., Photoplethysmograph Signal Reconstruction based on a Novel Motion Artifact Detection-Reduction Approach. Part II: Motion and Noise Artifact Removal. Annals of Biomedical Engineering, 2014. 42(11): p. 2251-2263). Clinicians have cited motion artifacts in pulse oximetry as the most common cause of false alarms, loss of signal, and inaccurate readings (Jubran, A., Pulse oximetry. Crit Care, 1999. 3(2): p. R11-r17). During physical activities, MA contamination in PPG signals seriously interferes with HR estimation. The MAs are mainly caused by ambient light leaking into the gap between the PPG sensor surface and skin surface. Besides, the change in blood flow due to movements is another MA source (Maeda, Y., M. Sekine, and T. Tamura, Relationship between measurement site and motion artifacts in wearable reflected photoplethysmography. J Med Syst, 2011. 35(5): p. 969-76). In practice, MAs are difficult to remove because they do not have a predefined narrow frequency band and their spectrum often overlaps that of the desired signal (Thakor, N. V. and Y. S. Zhu, Applications of adaptive filtering to ECG analysis: noise cancellation and arrhythmia detection. IEEE Trans Biomed Eng, 1991. 38(8): p. 785-94). Consequently, development of methods capable of reconstructing the corrupted signal and removing artifacts is challenging. There are a number of general techniques used for artifact detection and removal. One of the methods used to remove motion artifacts is adaptive filtering (Diniz, P., Adaptive filtering: algorithms and practical implementation. 2008: Springer Science, Business Media L.L.C., Kalman, R. E., A New Approach to Linear Filtering and Prediction Problems Transactions of the ASME—Journal of Basic Engineering, 1960. Series D(82); Morbidi, F., et al., Application of Kalman Filter to Remove TMS-Induced Artifacts from EEG Recordings. Control Systems Technology, IEEE Transactions on, 2008. 16(6): p. 1360-1366; Seyedtabaii, S. S. a.L., Kalman filter based adaptive reduction of motion artifact from photoplethysmographic signal. World Academy of Science, Engineering and Technology, 2008. 37). An adaptive filter is easy to implement and it also can be used in real-time applications, though the requirement of additional sensors to provide reference inputs is the major drawback of such methods. There are many motion and noise artifact reduction techniques based on the concept of blind source separation (BSS). The aim of BSS is to estimate a set of uncorrupted signals from a set of mixed signals which is assumed to contain both the clean and noisy sources (Salehizadeh, S. M. A., et al., Photoplethysmograph Signal Reconstruction based on a Novel Motion Artifact Detection-Reduction Approach. Part Motion and Noise Artifact Removal. Annals of Biomedical Engineering, 2014. 42(11): p. 2251-2263). Some of the popular BSS techniques are independent component analysis (ICA) (Comon, P., Independent component analysis, A new concept? Signal Processing, 1994. 36(3): p. 287-314), canonical correlation analysis (CCA) (Thompson, B., Canonical Correlation Analysis: Uses and Interpretation. 1984: SAGE Publications), principle component analysis (PCA) (Jolliffe, I. T., Principal Component Analysis. 2 ed. Springer Series in Statistics. 2002: Springer-Verlag New York. 488), and singular spectrum analysis (SSA) (Salehizadeh, S. M. A., et al., Photoplethysmograph Signal Reconstruction based on a Novel Motion Artifact Detection-Reduction Approach. Part II: Motion and Noise Artifact Removal. Annals of Biomedical Engineering, 2014. 42(11): p. 2251-2263; Elsner, J. B. and A. A. Tsonis, Singular Spectrum Analysis: A New Tool in Time Series Analysis. 1996: Springer). Kim and Yoo (Kim, B. S. and S. K. Yoo, Motion artifact reduction in photoplethysmography using independent component analysis. IEEE Trans Biomed Eng, 2006. 53(3): p. 566-8) suggested using a basic ICA method and block interleaving to remove MA. Krishnan et al. (Krishnan, R., B. Natarajan, and S. Warren, Two-Stage Approach for Detection and Reduction of Motion Artifacts in Photoplethysmographic Data. Biomedical Engineering, IEEE Transactions on, 2010. 57(8): p. 1867-1876) later proposed using frequency-domain-based ICA. However, the key assumption in ICA, namely statistical independence or uncorrelation, does not hold in PPG signals contaminated by MA (Yao, J. and S. Warren, A short study to assess the potential of independent component analysis for motion artifact separation in wearable pulse oximeter signals. Conf Proc IEEE Eng Med Biol Soc, 2005. 4: p. 3585-8). Salehizadeh et al. (Salehizadeh, S. M. A., et al., Photoplethysmograph Signal Reconstruction based on a Novel Motion Artifact Detection-Reduction Approach. Part II: Motion and Noise Artifact Removal. Annals of Biomedical Engineering, 2014. 42(11): p. 2251-2263) proposed a motion artifact removal method using SSA. In Salehizadeh, S. M. A., et al., Photoplethysmograph Signal Reconstruction based on a Novel Motion Artifact Detection-Reduction Approach. Part II: Motion and Noise Artifact Removal. Annals of Biomedical Engineering, 2014. 42(11): p. 2251-2263, SSA is used to decompose the corrupted segment adjacent to the clean segment and the SSA components are chosen in the corrupted segment that have a similar frequency range to that of the adjunct clean components. Although Salehizadeh, S. M. A., et al., Photoplethysmograph Signal Reconstruction based on a Novel Motion Artifact Detection-Reduction Approach. Part H: Motion and Noise Artifact Removal. Annals of Biomedical Engineering, 2014. 42(11): p. 2251-2263 reports good performance, the method cannot be applied in scenarios where the HR and $SpO_2$ are varying rapidly due to corruption and movement. Acceleration data are also shown to be helpful to remove MA. For example, Fukushima et al. (Fukushima, H., et al., Estimating heart rate using wrist-type Photoplethysmography and acceleration sensor while running. Conf Proc IEEE Eng Med Biol Soc, 2012. 2012: p. 2901-4) suggested a spectral subtraction technique to remove the spectrum of acceleration data from that of a PPG signal. Acceleration data can be also used to reconstruct the observation model for Kalman filtering (Boreom Lee, J. H., Hyun Jae Baek, Jae Hyuk Shin, Kwang Suk Park and Won Jin Yi, Improved elimination of motion artifacts from a photoplethysmographic signal using a Kalman smoother with simultaneous accelerometry. Physiological Measurement, 2010. 31(12): p. 1585) to remove MA.

Two noteworthy methods are TROIKA and JOSS (Zhilin, Z., P. Zhouyue, and L. Benyuan, TROIKA: A General Framework for Heart Rate Monitoring Using Wrist-Type Photoplethysmographic Signals During Intensive Physical Exercise. Biomedical Engineering, IEEE Transactions on, 2015. 62(2): p. 522-531; Zhang, Z., Photoplethysmography-Based Heart Rate Monitoring in Physical Activities via Joint Sparse Spectrum Reconstruction. Biomedical Engineering, IEEE Transactions on, 2015. PP(99): p. 1-1) in which sparsity-based spectrum estimation and spectral peak tracking with verification, are used to estimate and monitor heart rate during intensive physical activity, respectively. Both approaches make use of PPG and accelerometer information to obtain an accurate estimation of heart rate while running on a treadmill. TROIKA has two extra stages of signal decomposition and reconstruction using singular spectrum analysis (SSA) and then applies temporal difference operations on the SSA-reconstructed PPG. SSA components are compared to the accelerometer signals and those components with close frequencies to the accelerometer signals are discarded and the rest are used to reconstruct the signal. In JOSS and TROIKA, spectral peak tracking with verification aims to select the spectral peaks corresponding to HR. JOSS, which has been shown to estimate HR more accurately than TROIKA, is based on the idea that the spectra of PPG signals and simultaneous acceleration signals have some common spectrum structures, and, thus, formulates the spectrum estimation of these signals into a joint sparse signal recovery model using the multiple measurement vector (MMV) model. MMV is used for joint spectrum estimation based on PPG and accelerometer data, which is in contrast to the single measurement vector (SMV) model that was used in TROIKA and was based on only a single PPG signal. Although JOSS has been shown to be much more accurate than previous methods for reconstruction of heart rate from MA-contaminated PPG signals, the main disadvantage of the method is it can merely provide smoothed HR reconstruction estimations. Neither time-domain PPG signal reconstruction nor heart rate variability analysis can be done using JOSS or TROIKA. Temko proposed an approach to FIR estimation based on Wiener Filtering and the Phase Vocoder (WFPV) (Temko, A. Estimation of Heart Rate from Photoplethysmography during Physical Exercise using Wiener Filtering and the Phase Vocoder. in IEEE EMBS International Conference on Engineering in Medicine and Biology. 2015. Milan, Italy: IEEE). This work showed that WFPV on average can perform better than JOSS. The main idea of WFPV is to estimate motion artifacts from accelerometer signals and then use a Wiener filter to attenuate the motion components in the PPG signal. Phase vocoder is also applied to overcome the limited resolution of the Fourier transform and to refine the initial dominant frequency estimation.

According to embodiments disclosed herein, a motion-corrupted heart-related signal, such as a PPG signal, may be reconstructed by employing a method that is based on a time-varying spectral analysis. A method for reconstructing a heart-related signal based on the time-varying spectral analysis for HR estimation may be referred to interchangeably herein as a spectral approach for filtering motion artifacts (SpaMA) method or SpaMA. A method for reconstructing the heart-related signal based on the time-varying spectral analysis for SpO2 estimation may be referred to interchangeably herein as a spectral approach for filtering motion artifacts for oxygen saturation estimation (OxiMA) method or OxiMA.

FIG. 1 is a block diagram 100 of an example application for which embodiments disclosed herein may be applied. In FIG. 1, a subject 102 is running on a treadmill 104. The subject 102 is wearing a wrist band 106 that includes a biomedical sensor 108 that produces a heart-related signal 110. The heart-related signal 110 that is produced by the biomedical sensor 108 includes motion artifacts that are signal artifacts produced by movement of the biomedical sensor 108 relative to a sensing location (not shown). The wrist band 106 may be any suitable type of wrist band, for example, the wrist band 106 may be a smart watch.

The biomedical sensor 108 may be a PPG sensor, or any other suitable biomedical sensor, and the heart-related signal 110 may be a PPG signal, or any other suitable heart-related signal. The sensing location may a skin surface of an area on the subject's wrist where the wrist band 106 is worn, or any other suitable sensing location at which the biomedical sensor 108 senses the heart-related signal 110. For example, the sensing location may be a skin surface on the subject's forehead, and a head band including the biomedical sensor 108 or maintain the biomedical sensor 108 at the sensing location may be used instead of the wrist band 106.

Physical activity of the subject 102 may cause movement of the wrist band 106, and, thus, movement of the biomedical sensor 108, resulting in a gap between the PPG sensor and the sensing location. Ambient light may leak into the gap inducing spectrum corruption in the PPG signal. This is because the power of the PPG signal is dependent on a depth and reflection of the PPG light from the PPG sensor to the subject's skin. As such, strenuous and high intensity exercise of the subject 102, such as running or any other suitable activity, may result in movement that rises to a level causing motion artifacts in the heart-related signal 110. According to embodiments disclosed herein, the heart-related signal 110 may be reconstructed 112, producing a reconstructed heart-related signal with the motion artifacts suppressed 114. The reconstructed heart-related signal with the motion artifacts suppressed 114 may be used to accurately estimate HR, SpO2, or any other suitable heart-related estimate. As such, the reconstructed heart-related signal may be employed to detect or predict a heart-related ailment. The heart-related ailment may include at least one of a heart rate variability (HRV) condition, atrial fibrillation condition, congestive heart failure condition, and tachycardia condition.

It should be understood that the PPG sensor is one example of a biomedical sensor, the PPG signal is one example of a heart-related signal, and that any suitable type of biomedical sensor may be employed to produce any suitable type of a heart-related signal. Further, movement of the biomedical sensor 108 relative to the sensing location may be caused by any suitable source of the movement that causes movement of the biomedical sensor 108 relative to the sensing location. It should also be understood that a subject referred to herein may be any living being, such as a person or an animal, and may be referred to interchangeably herein as a user.

Figure 2:
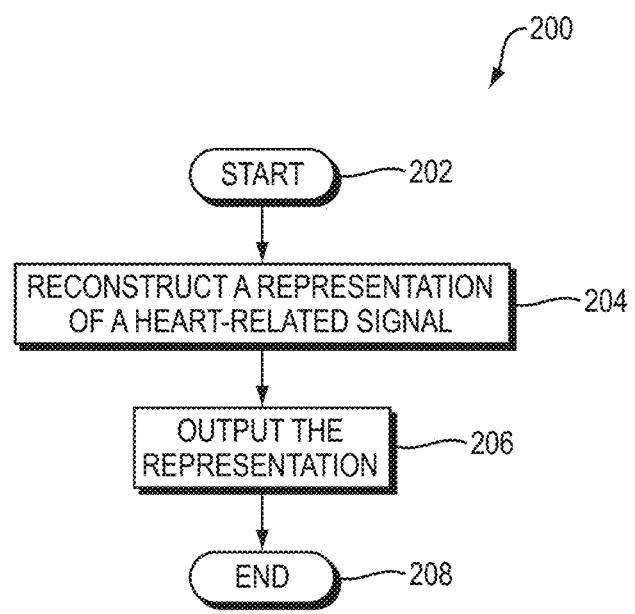
FIG. 2 is a flow diagram of an example embodiment of a method for reconstructing a heart-related signal output by a biomedical sensor.

FIG. 2 is a flow diagram 200 of an example embodiment of a method for reconstructing a heart-related signal output by a biomedical sensor. The example embodiment of the method of FIG. 2 may be applied to either SpaMA or OxiMA and may be applied to other applications that produce a heart-related estimate. The method may start (202) and reconstruct a representation of the heart-related signal to produce a reconstructed representation of the heart-related signal. The reconstructing may be based on (i) a time-varying spectral analysis of the heart-related signal and a motion signal, the motion signal output by a motion sensor and representative of motion artifacts in the heart-related signal, the motion artifacts being signal artifacts produced by movement of the biomedical sensor relative to a sensing location, and (ii) a classification of movement (204). The method may output the reconstructed representation of the heart-related signal (206), and the method thereafter ends (208) in the example embodiment.

The method may comprise segmenting the heart-related signal into a plurality of windowed heart-related signal data segments and the motion signal into a corresponding plurality of windowed motion signal data segments and repeating the reconstructing and the outputting for each windowed heart-related signal data segment and each corresponding motion signal data segment. The time window may be a value in a range from 2 to 32 seconds. For example, the window[k] of raw PPG data of FIG. 3A, element 304, disclosed below, and the window[k] of raw accelerometer data shown in FIG. 3A, element 310, disclosed below, may each include data from the respective PPG and accelerometer signals that may be collected over a time window from 2 to 32 seconds. According to one embodiment, the time window may be 8 seconds.

The method may employ the reconstructed representation to determine a heart rate estimate. The method may employ the reconstructed representation to determine an arterial oxygen saturation (SpO2) estimate. The method may employ the reconstructed representation to detect or predict a heart-related ailment. The heart-related ailment may include at least one of a heart rate variability (HRV) condition, atrial fibrillation condition, congestive heart failure condition, and tachycardia condition.

The heart-related signal and the motion signal may be produced, concurrently.

According to some embodiments, the biomedical sensor may be at least one of: a photoplethysmogram (PPG) sensor, piezoelectric sensor, Light Emitting Diode (LED) based sensor, camera sensor, and pulse oximeter sensor. The motion sensor may be an accelerometer, or any other suitable device that produces a motion signal. If an accelerometer, the accelerometer may be a 3-axial type accelerometer, or any other suitable type of accelerometer.

The biomedical sensor and the motion sensor may be co-located. For example, the wrist band 106 of FIG. 1, disclosed above, may be a smartwatch and the biomedical sensor and motion sensor may be a PPG sensor and an accelerometer, respectively, that are both disposed in the smartwatch or other suitable wearable device.

Figure 3A:
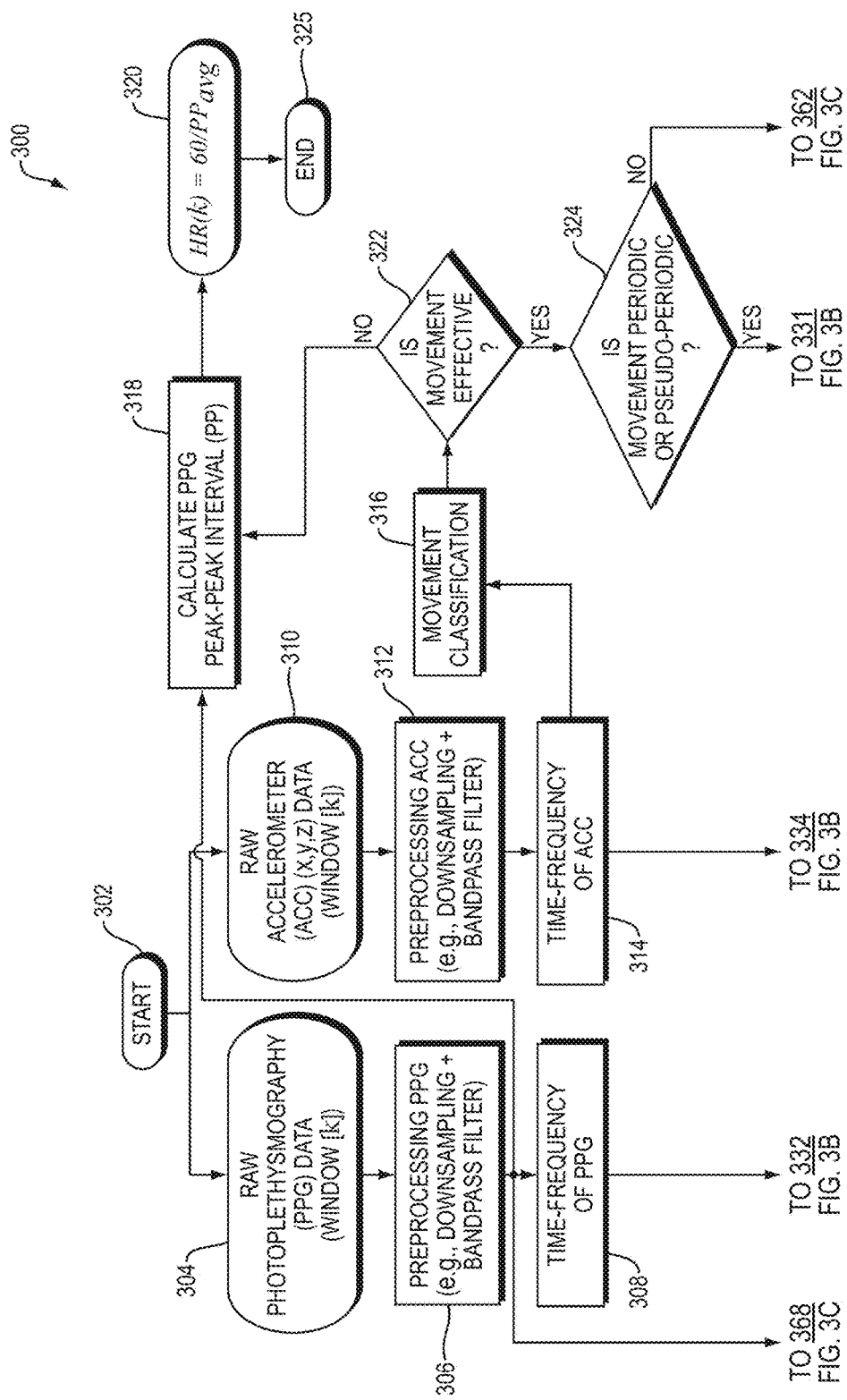
FIGS. 3A-C are flow diagrams of example embodiments of a method for reconstructing a heart-related signal output by a biomedical sensor.
Figure 3B:
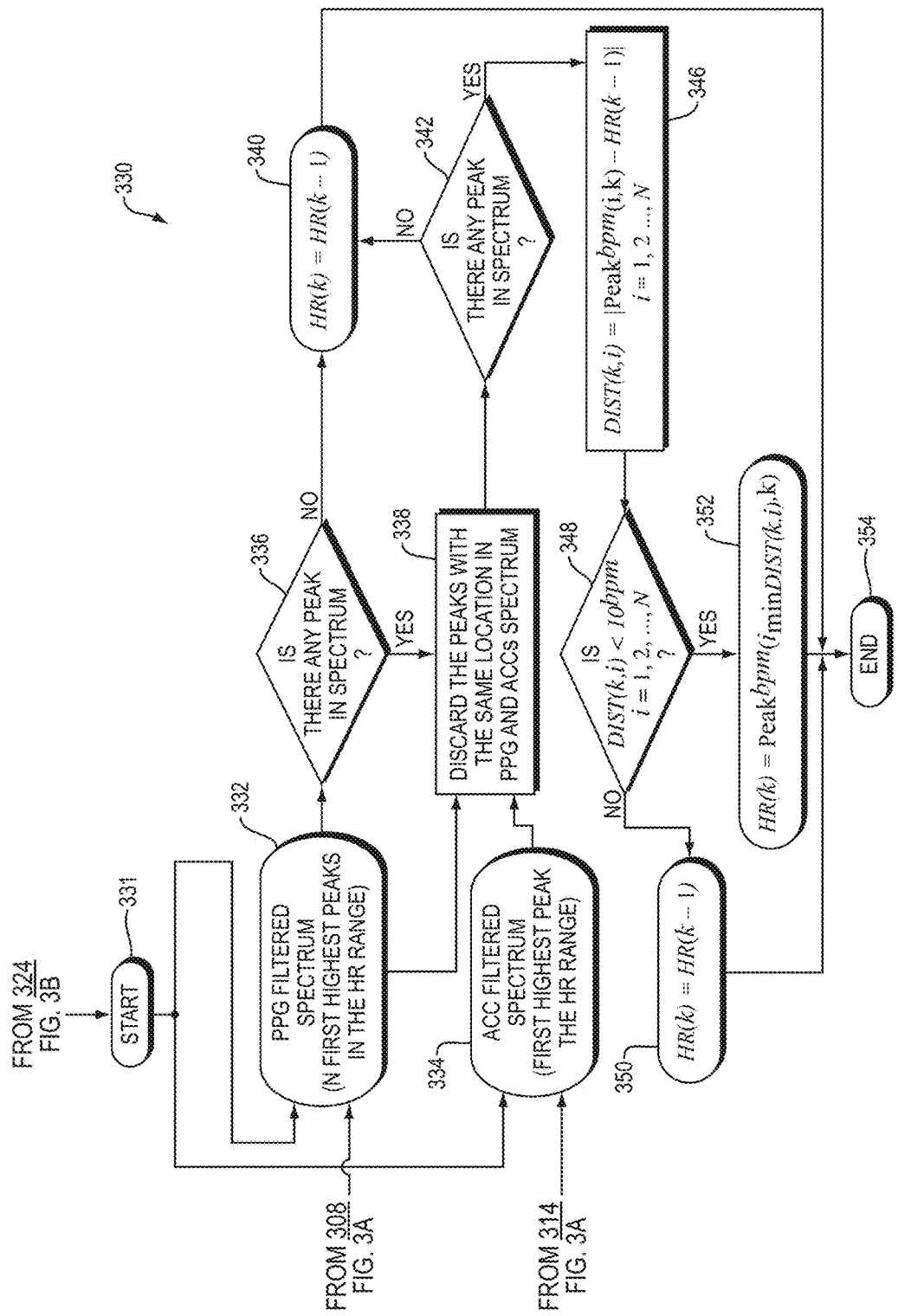
Figure 3C:
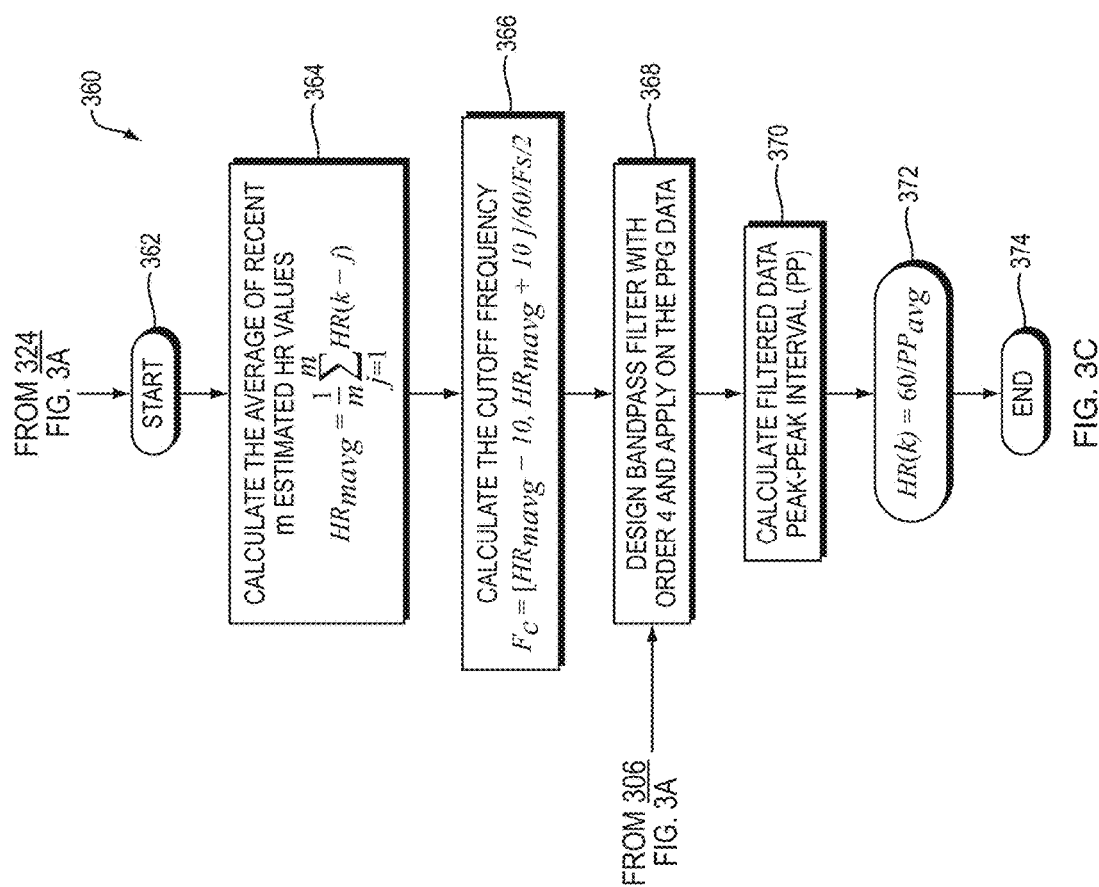

FIGS. 3A-C are flow diagrams of example embodiments of a method for reconstructing a heart-related signal output by a biomedical sensor based on embodiments disclosed in Tables 1-3, disclosed below. The method may be either a SpaMA or OxiMA method.

TABLE 1

Stages 1 and 2

Stage 1. Time-Varying Spectral analysis (see FIG. 3A)
    1.1. Filter the PPG and Accelerometer signal with cutoff frequency [1, 50]/Fs/2 Hz.
    1.2. Down sample the PPG and Accelerometer signal to ¼ of original sampling rate (Fs).
    1.3. Compute the time frequency spectrum of both PPG and Accelerometers [0-10 Hz].
Stage 2. Movement Classification (see FIG. 3A)
    2.1. Check each accelerometer (X, Y or Z) amplitude modulation at each window and
    compare to a pre-defined motion amplitude threshold. (The threshold varies depending on
    the type of accelerometer sensor).
    Signal is clean if AM [$Acc_{x\ or\ y\ or\ z}$ (k)] < Motion_Threshold and the signal is corrupted by
    motion otherwise. If the signal is clean calculate the Heart Rate from peak-to-peak intervals,
    otherwise go to step 2.2.
    2.2. If the signal is corrupted check if the movement is pseudo-periodic (e.g. during walk, jog,
    run) or non-periodic (e.g. any random movements)
    The assumption is when movement is pseudo-periodic the accelerometer data should
    comprised of a fundamental frequency component and harmonics of the fundamental
    frequency at its double and third frequency band. This means the ratio of the first harmonic to
    the fundamental frequency should be almost 2 and the second harmonic to the fundamental
    should be around 3.
        2.2.1. Extract the fundamental frequency component, the $1^{st}$ and $2^{nd}$ harmonics from
        (e.g., VFCDM) time-frequency spectrum of accelerometers. The first three
        highest peaks in spectral array should represent the fundamental, $1^{st}$ and $2^{nd}$
        harmonics as long as the movement is pseudo-periodic.
        2.2.2. Calculate the ratio of the extracted 1st and 2nd fundamental frequency to the
        extracted fundamental frequency. If the ratios are close to 2 and 3, this indicates
        that the movement is most likely pseudo-periodic otherwise it is non-periodic.
        2.2.3. If the movement is pseudo-periodic do the Stages 3-5 (See Table 2 and FIG.
        3B), otherwise go to Stage 6 (See Table 3 and FIG. 3C).

TABLE 2

Stages 3-5

Stage 3. Spectral Filtering (see FIG. 3B)
    3.1. Assume HR to be in the frequency range of [0.5 Hz-3 Hz], this accounts for both low and high heart rates.
    3.2. The first highest three peaks and their corresponding frequencies in the PPG filtered spectrum are assumed to have HR information.
    3.3. Only the largest frequency peak (that represents the fundamental frequency of movement) of the accelerometers' spectra is used for motion artifact detection in Stage 4.
Stage 4. Motion Artifact Detection (see FIG. 3B)
    4.1. Compare the frequencies of the three peaks in the PPG spectrum with the frequency of the largest peak in the accelerometers' spectra. If the first or second largest peaks in the PPG spectrum are similar to that of the accelerometers' peaks, then motion artifact is present in the PPG.
    4.2. If motion artifact is detected from 3.1, then the corresponding frequency peak (usually the first or second largest peak) in the PPG spectrum should be discarded.
Stage 5. Heart Rate Tracking and Extraction from PPG Spectrum (see FIG. 3B)
    Case (1): From 3.1- if the spectrum is corrupted by movement and only the first largest peak is corrupted,
    then the HR frequency should be the frequency of the second peak in the spectrum.
    Case (2): From 3.1- if the spectrum is corrupted by movement and both the first and second largest peaks have similar frequencies to those of the accelerometers' peaks, then the HR frequency should be the frequency of the third peak in the spectrum.
    Case (3): Due to a gap between the pulse oximeter and a subject's skin, the HR frequency cannot be extracted from the spectrum and in this case the previous HR frequency is used or for offline implementation a cubic spline interpolation can be applied to fill in the missing HR information.

TABLE 3

Stage 6

Stage 6. Adaptive Bandpass Filtering (non-periodic movements) (see FIG. 3C)
When the movement is random and non-periodic it is difficult or not possible to identify HR trace from time-frequency spectrum (for example if stage 5 is not applicable). In this case which may happen more often, a new procedure is adopted that is called adaptive bandpass filtering. The assumption here is that HR does not deviate more than 10 bpm from the average of previous m HR values within 2 seconds.
6.1. Set averaging window length to m (e.g. m = 5) and calculate theaverage of recent m estimated HR values.

$$HR_{mavg} = \frac{1}{m}\sum_{j=1}^{m} HR(k-j)$$

Where k is the current window. The window length m = 5 should only be used for up to 10 seconds of consecutive motion artifact corrupted datapoints. If motion corrupted data last more than 10 seconds, m should be increased to more than 5.
6.2. Take the most recent estimated HR value and calculate bandpass filter cutoff frequency.
$F_{Cutoff} = [HR_{mavg} - 10, HR_{mavg} + 10]/60/Fs/2$
Design a bandpass filter of order 4 with cutoff frequency ($F_{CutOff}$).
Apply the filter on the PPG segment.
6.3. Calculate HR from peak-to-peak intervals of the filtered data segment obtained from 6.2.
Take the average of the instantaneous HR as estimated HR value at window k.

FIG. 3A is a flow diagram (300) of an example embodiment of a method for a time-varying spectral analysis and movement classification, as disclosed in Stage 1 (time-varying spectral analysis) and Stage 2 (movement classification), respectively, in Table 1, for reconstructing the representation. The method may start (302) and the time-varying spectral analysis may be employed on a first windowed segment window[k] of raw PPG data (304) and a second windowed segment window[k] of raw accelerometer (ACC) data (310). The raw PPG data (304) and the raw ACC data (310) may be extracted from a heart-related signal that is a PPG signal and a motion signal that is an accelerometer signal, respectively.

As disclosed in Stage 1 of Table 1, the time-varying spectral analysis of FIG. 3A may include pre-processing the heart-related signal (306) to produce a pre-processed heart-related signal. The pre-processing (306) may include filtering the heart-related signal to produce a filtered heart-related signal. The pre-processing (306) may further include down-sampling the filtered heart-related signal, the down-sampling being at a sampling rate less than an original sampling rate, to produce a down-sampled, filtered heart-rate signal. The time-varying spectral analysis may further include pre-processing the motion signal (312) to produce a pre-processed motion signal. The pre-processing (312) may include filtering the motion signal to produce a filtered motion signal. The pre-processing (312) may further include down-sampling the filtered motion signal, the down-sampling being at a sampling rate less than an original sampling rate, to produce a down-sampled, filtered motion signal.

As further disclosed in Stage 1 of Table 1, the time-varying spectral analysis of FIG. 3A may include computing a first time-frequency spectrum (TFS) to produce a first TFS (308) of the down-sampled, filtered heart-related signal and computing a second TFS to produce a second TFS (314) of the down-sampled, filtered motion signal. According to some embodiments, filtering and down-sampling of the heart-related signal and motion signal for computing the first TFS (308) and the second TFS (314), respectively, may be optional. The first TFS (308) (also referred to interchangeably herein as the first TFS computed) and the second TFS (314) (also referred to interchangeably herein as the second TFS computed) may be 3-dimensional spectra, the first TFS computed and the second TFS computed each including a respective time-varying amplitude or power distribution with respect to time and frequency.

For example, the first TFS computed may be a first time-varying power spectral density (PSD) and the second TFS computed may be a second time-varying PSD. A time-frequency technique, such as a variable frequency complex demodulation (VFCDM), disclosed in U.S. Pat. No. 8,388,543 B2, incorporated herein in its entirety by reference, may be used for computing the first TFS (308), that is, a TFS of the PPG signal, and the second TFS (314), that is, a TFS of the accelerometer signal. However, it should be understood that any suitable time-frequency technique may be used, such as a smoothed pseudo wigner-ville method, or a wavelet based method.

As disclosed in Stage 2 of Table 1, classifying the classification of the movement (316) in FIG. 3A may include comparing an amount of amplitude modulation in the second TFS (314) computed to an amplitude modulation threshold. The amplitude modulation threshold may be dependent on a type of the motion detector sensor, such as a type of the accelerometer. The classification of the movement may indicate whether the movement rises to a level causing motion artifacts in the heart-related signal, that is, the PPG signal, based on a result of the comparing, as disclosed in Stage 2 of Table 1.

In an event the movement classification (316) of FIG. 3A indicates that the movement does not rise to a level causing the motion artifacts (322), a peak-peak interval (PP) of the filtered heart-related signal, or alternatively, the filtered, down-sampled heart-rate signal, may be computed (318) and the reconstructed representation HR(k) may be based on an average value of peak-to-peak intervals (320) in the pre-processed heart-related signal, and the method thereafter ends (325) in the example embodiment.

In an event the movement classification (316) indicates that the movement does rise to the level causing the motion artifacts (323), classifying the classification of the movement may further include determining (324) whether the movement is either a pseudo-periodic movement or a periodic movement, versus a random movement, as disclosed in Stage 2 of Table 1.

With reference to Stage 2 of Table 1, in determining whether the movement is either the pseudo-periodic movement or the periodic movement, versus the random movement, the method may further include identifying a first, second, and third frequency associated, respectively, with a first, second, and third spectral peak in the second TFS at a point in time in the second TFS. The first, second, and third peaks may have largest power or amplitude values relative to other peaks in the second TFS at the point in time. The first spectral peak may be a largest spectral peak amongst the first, second, and third spectral peaks.

In determining whether the movement is either the pseudo-periodic movement or the periodic movement, versus the random movement, the method may compute a first ratio of the second frequency identified to the first frequency identified. The method may determine a first comparison result by comparing the first ratio computed to a first ratio value. The method may compute a second ratio of the third frequency identified to the first frequency identified and determine a second comparison result by comparing the second ratio computed to a second ratio value. The classification may further indicate the movement is either the pseudo-periodic movement or the periodic movement, versus the random movement, based on the first comparison result and the second comparison result. The first ratio value may be 2 and the second ratio value may be 3. The classification of the movement may be periodic if the first ratio and the second ratio are exactly 2 and 3, respectively, while the classification of the movement may be pseudo-periodic if the first ratio and the second ratio are approximately 2 and 3, respectively, within a pre-determined level of accuracy.

In an event the classification of the movement is periodic or pseudo-periodic, the method of FIG. 3A may continue with the method of FIG. 3B, disclosed below. In an event the classification of the movement is random, the method of FIG. 3A continues to the method of FIG. 3C, disclosed below.

FIG. 3B is a flow diagram (330) of an example embodiment of a method for spectral filtering, motion artifact detection, and heart rate tracking and extraction, as disclosed in Stages 3, 4, and 5, respectively, of Table 2, for reconstructing the representation. The reconstructed representation may be referred to herein as a current reconstructed representation or HR(k). As disclosed above with regard to FIG. 3A, in an event the classification of the movement (316) is periodic or pseudo-periodic, the method of FIG. 3A may continue with the method of FIG. 3B.

The method of FIG. 3B may start (331) and retain (332) up to a pre-determined number N of candidate spectral peaks located at a first point in time in the first TFS, that is, the first TFS from FIG. 3A. It should be understood that the method of FIG. 3B may be performed for each point in time of the first TFS and the second TFS. According to one embodiment, the pre-determined number N may be 3. The candidate spectral peaks retained may be based on having corresponding frequencies within a given frequency range. The candidate spectral peaks may be N peaks in the given frequency range that have highest amplitude or power values relative to other spectral peaks, that is, the first N highest peaks. It should be understood that the other spectral peaks have respective frequencies also within the given frequency range and are peaks located at the first point in time in the first TFS. The given frequency range may be 0.5 Hz to 3 Hz. As such, the N first highest peak in the range 0.5 Hz to 3 Hz in the first TFS may be retained at the first time point. Since no peaks in the given frequency range may be present at the first time point, the method may determine (336) whether at least one spectral peak is present.

Based on the determination (336) that no peak is present, the current reconstructed representation HR(k) may be based on a prior reconstructed representation HR(k−1) (340), the prior reconstructed representation HR(k−1) associated with a previous point in time, such as the previous window k−1, in the first TFS computed, and the method thereafter ends (354) in the example embodiment.

Based on a determination (336) that the at least one spectral peak is present, the method may discard (338) each of the candidate spectral peaks retained, that is, each peak of the N first highest peaks determined at (332), if the peak is associated with a same frequency as a dominant spectral peak located at a second point in time in the second TFS (314) computed as disclosed above with regard to FIG. 3A. The first point in time and the second point time may have same time values. The dominant spectral peak may have a largest power or amplitude value relative to other peaks located at the second point in time in the second TFS. The method may determine (342) whether any peaks are retained after the discarding (338). The discarding (338) may be referred to herein as a first discarding.

In an event the discarding (338) discards each of the candidate spectral peaks retained, reconstructing the current representation HR(k) may be based on the prior reconstructed representation, HR(k−1) (340), and the method thereafter ends (354) in the example embodiment.

In an event the first discarding (338) results in at least one remaining candidate spectral peak retained, reconstructing the current representation may further include second discarding (348). The second discarding (348) may discard remaining candidate spectral peaks, of the at least one remaining candidate spectral peak retained, based on whether a corresponding frequency of the at least one remaining candidate spectral peak retained is distanced (346) by at least a frequency difference threshold, such as 10 bpm, from a prior reconstructed representation's frequency, that is, a frequency associated with, for example, HR(k−1).

Based on each at least one remaining candidate spectral peak retained having been discarded by the second discarding (348), reconstructing the current representation may be based on the prior reconstructed representation HR(k−1) (350), and the method thereafter ends (354) in the example embodiment.

Based on at least one last candidate spectral peak remaining from the second discarding (348), reconstructing the current representation may be based on a selected candidate spectral peak (352). The selected candidate spectral peak may be selected from amongst the at least one last candidate spectral peak remaining having a closest corresponding frequency to the prior reconstructed representation's frequency relative to respective frequencies of each of the at least one last candidate spectral peak remaining, and the method thereafter ends (354) in the example embodiment.

As disclosed above with regard to FIG. 3A, in an event the classification of the movement (316) is random, the method of FIG. 3A may continue with the method of FIG. 3C.

FIG. 3C is a flow diagram (330) of an example embodiment of a method for adaptive bandpass filtering of non-periodic movements, that is, random movements, for reconstructing the representation, as disclosed in Stage 6 of Table 3. The method of FIG. 3C may start (362) and compute an average value of a number m of prior reconstructed representations outputted prior to the reconstructing (362). The number m may be based on a duration of consecutive motion artifacts, detected prior to the reconstructing of the representation HR(k). For example, if motion artifacts were detected for windows k−1, k−2, and k−3, m may be understood to be 3.

The method may compute a bandpass filter cutoff frequency (366). The cutoff frequency may be based on the average value computed $HR_{mavg}$. The method may filter the pre-processed heart-rate signal (306), disclosed in FIG. 3A, above, by applying the band pass filter computed (368) to produce a filtered, pre-processed heart-related signal. The reconstructed representation HR(k) may be based on an average peak-to-peak interval value (372) of the filtered, pre-processed heart-rate signal, and the method thereafter ends (374) in the example embodiment.

Figure 4:
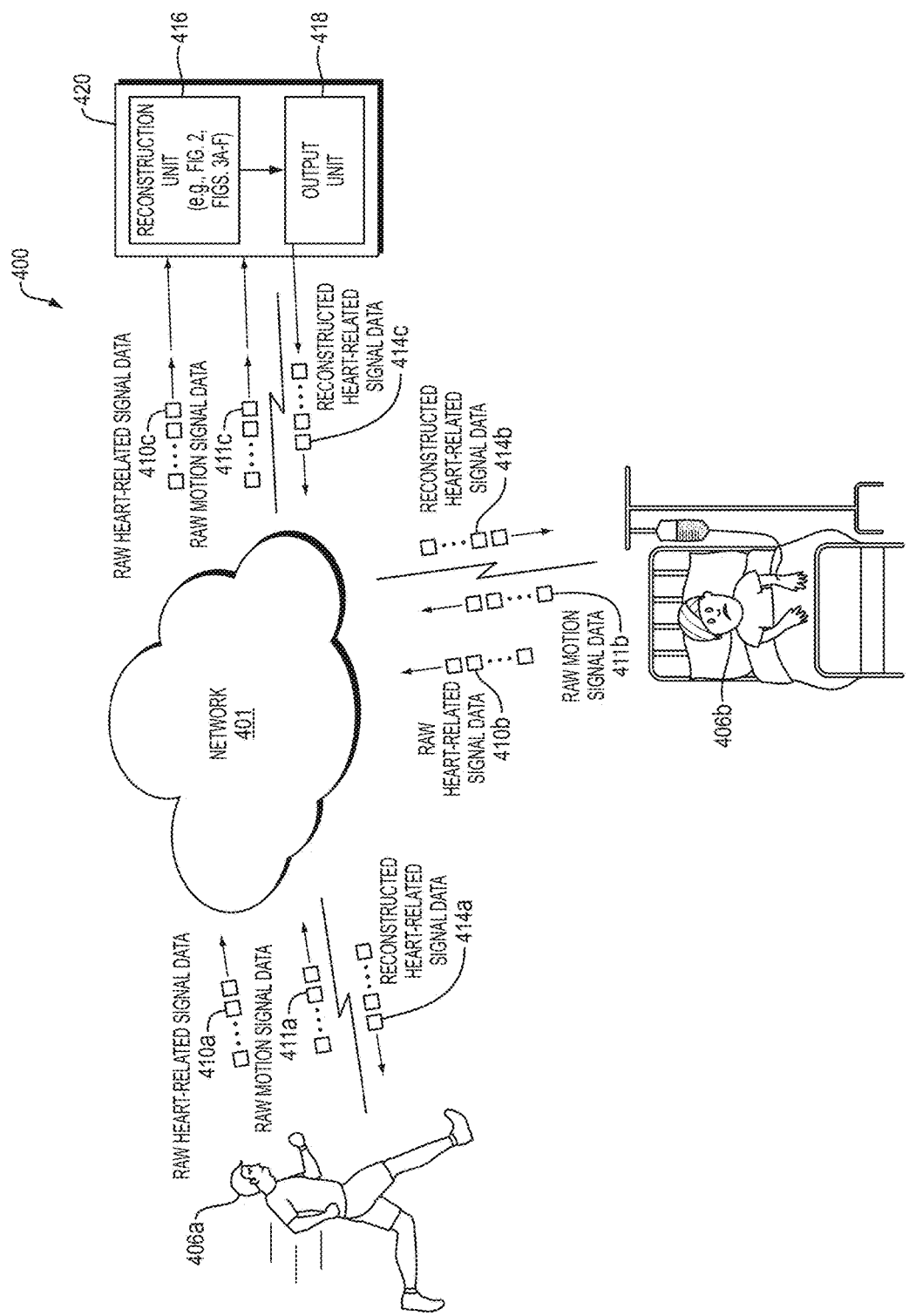
FIG. 4 is a block diagram of an example embodiment of a system.

FIG. 4 is a block diagram of an example embodiment of a system (400). The system includes an apparatus 420 for reconstructing a heart-related signal 410c output by a biomedical sensor (not shown). The apparatus 420 includes a reconstruction unit 416 and an output unit 418. The reconstruction unit 416 may be configured to produce a reconstructed representation of the heart-related signal 414c. The reconstructing may be based on (i) a time-varying spectral analysis of the heart-related signal 410c and a motion signal 411c, the motion signal 411c output by a motion sensor (not shown) and representative of motion artifacts in the heart-related signal 410c, the motion artifacts being signal artifacts produced by movement of the biomedical sensor (not shown) relative to a sensing location (not shown), and (ii) a classification of the movement. The output unit 418 may be configured to output the reconstructed representation of heart-related signal 414c.

The apparatus 420 may be communicatively coupled to a network 401 to receive the heart related signal 410c and the motion signal 411c. The network may be a wireless network or any other suitable network. The reconstructing and the outputting may be performed in near real-time with respect to production of the heart-related signal 410c and the motion signal 411c. Alternatively, the apparatus may be coupled to a database (not shown) storing representations of the heart related signal 410c and the motion signal 411c, and the reconstructing and the outputting may be performed in non-real-time with respect to production of the heart-related signal 410c and the motion signal 414c.

The heart-related signal 410c may include raw heart-related signal data that includes the raw heart-related signal data 410a and the raw heart-related signal data 410b produced by biometric sensors (not shown) that sense the heart-related signal data 410a and the raw heart-related signal data 410b from sensing locations (not shown) on a first user 406a and a second user 406b, respectively. The motion signal 411c may include raw motion signal data that includes the raw motion signal data 411a and the raw motion signal data 411b from motion sensors (not shown). The raw motion signal data 411a and the raw motion signal data 411b may represent motion artifacts in the heart-related signal data 410a and the raw heart-related signal data 410b, respectively.

It should be understood that the raw heart-related signal data 410a-b and the raw motion signal data 411a-b may be sent to the apparatus 420 in any suitable way. For example, the raw heart-related signal data 410a and the raw motion signal data 411a may be sent in a payload of a packet; alternatively the raw heart-related signal data 410a and the raw motion signal data 411a may be sent in payloads of different packets. Similarly, the raw heart-related signal data 410b and the raw motion signal data 411b may be sent in a payload of a packet; alternatively, the raw heart-related signal data 410b and the raw motion signal data 411b may be sent in payloads of different packets.

The user 406a may be at a gym where the user 406a is exercising, and such physical activity by the user 406a may cause motion artifacts in the raw heart-related signal data 410a. The user 406b may be in a different location, such as a hospital. The user 406b may perform movements out of boredom, such wrist shaking, causing motion artifacts in the raw heart-related signal data 410b. As such, the corresponding motion artifacts may be suppressed in the reconstructed representations 414a and 414b of the heart-related signals 414a and 414b, respectively, according to embodiments disclosed herein. The reconstructed representations 414a and 414b, or information derived therefrom, may sent to biometric devices or other devices communicatively coupled to the network 401 the user 406a and 406 may have access to such device, respectively. Alternatively, the reconstructed representations 414a and 414b, or information derived therefrom, may sent in any suitable manner to another device communicatively coupled to the network 401 such that the reconstructed representations 414a and 414b, or information derived therefrom, may be accessible to a third party, such as doctor, or any other suitable party.

Figure 5:
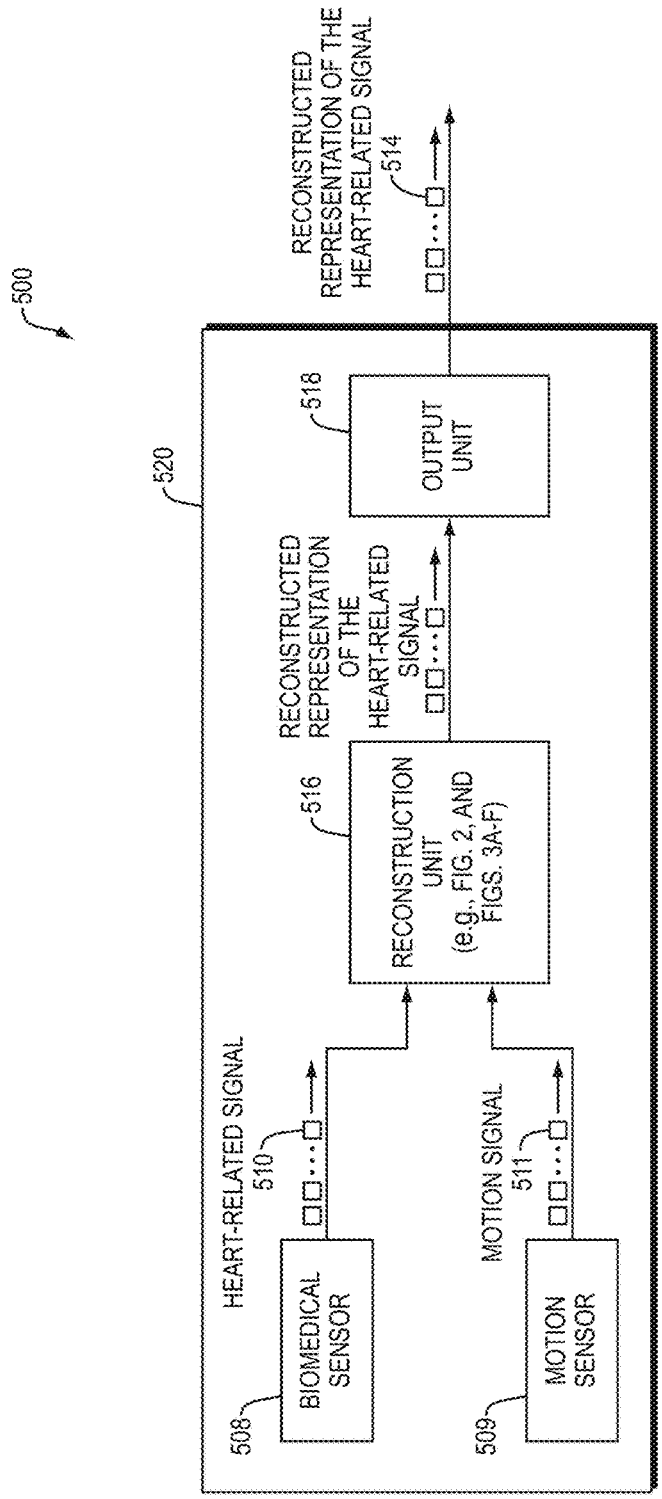
FIG. 5 is a block diagram of an example embodiment of an apparatus for reconstructing a heart-related signal output by a biomedical sensor.

FIG. 5 is a block diagram 500 of an example embodiment of an apparatus (520) for reconstructing a heart-related signal 510 output by a biomedical sensor 508. The apparatus 520 includes a reconstruction unit 516 and an output unit 518. The reconstruction unit 516 may be configured to produce a reconstructed representation of the heart-related signal 514. The reconstructing based on (i) a time-varying spectral analysis of the heart-related signal 510 and a motion signal 511, the motion signal 511 output by a motion sensor 509 and representative of motion artifacts in the heart-related signal 510. The motion artifacts may be signal artifacts produced by movement of the biomedical sensor 508 relative to a sensing location (not shown), and (ii) a classification of the movement.

The output unit 518 may be configured to output the reconstructed representation of the heart-related signal 514. The apparatus 520 may include the biomedical sensor 508 and the motion sensor 509. The reconstructing and the outputting may be performed in real-time with respect to production of the heart-related signal 510 and the motion signal 511.

The apparatus 520 may be a wearable device, such as a smartwatch, or any other suitable device, such as a wearable personal biometric monitoring device. The apparatus 520 may have a user interface (not shown) to present the reconstructed representation of the heart-related signal 514 or information derived therefrom, such as a characteristic, notification, alarm, or any other suitable information. The reconstructed representation of heart-related signal 514 or the information derived therefrom may be presented to a user via a user interface that may be a visual or audio based user interface.

According to one embodiment, the apparatus 520 may include a heart rate unit (not shown) configured to employ the reconstructed representation of the heart-related signal 514 to determine a heart rate estimate. According to another embodiment, the apparatus 520 may include an arterial oxygen saturation (SpO2) unit (not shown) configured to employ the reconstructed representation of the heart-related signal 514 to determine a SpO2 estimate. According to yet another embodiment, the apparatus may include an ailment unit (not shown) configured to employ the reconstructed representation of the heart-related signal 514 to detect or predict a heart-related ailment, the heart-related ailment including at least one of a heart rate variability (HRV) condition, an atrial fibrillation condition, a congestive heart failure condition, and a tachycardia condition. It should be understand that any combination of the heart rate unit, SpO2 unit, and ailment unit may be included in the apparatus 520 in combination with any other units disclosed herein.

SpaMA Results

According to embodiments disclosed herein, HR reconstruction and PPG signal reconstruction may be based on a time-varying spectral analysis. As disclosed above with reference to FIGS. 3A-F, embodiments disclosed herein may be based on power spectral densities (PSDs) of both PPG and accelerometer signals for each time shift of a corresponding windowed data segment of the respective signal. According to embodiments disclosed herein, by comparing time-varying spectra of the PPG and accelerometer data, those frequency peaks resulting from motion artifacts may be suppressed from the PPG spectrum.

According to some embodiments, the method may be comprised of six stages, such as the six stages disclosed above in reference to FIGS. 3A-F. According to another embodiment the method may have five distinct stages: (1) time-varying power spectral density (PSD) calculation, (2) spectral filtering, (3) motion artifact detection, (4) HR reconstruction and (5) signal reconstruction. According to embodiments disclosed herein, the method may include computing a window-segmented power spectral density of both PPG and accelerometer signals in real-time to scale each estimate of the PSD by the equivalent noise bandwidth of the window (Stoica, P. and R. L. Moses, Introduction to Spectral Analysis. 1997: Prentice Hall).

The simplest way to approach the PSD calculation may be to employ a periodogram. However, a periodogram has drawbacks in that it is an inconsistent spectrum estimator, has high variance, and has leakage effects (Stoica, P. and R. L. Moses, Introduction to Spectral Analysis. 1997: Prentice Hall). Thus, a dominant spectral peak can lead to an estimated spectrum that contains power in frequency bands where there should be no power. However, both problems can be solved by down-sampling the raw signal, as disclosed above with reference to FIGS. 3A-F, and then using a sufficiently small frequency step by setting a large number of frequency points. Thus, embodiments disclosed herein may resample the signal from the original sampling frequency to, for example ¼ of it, that is, down-sample the signal, and then apply a periodogram method with frequency resolution of 0.001.

Embodiments disclosed herein may limit the spectrum to the heart rate frequency range of [0.5 Hz-3 Hz], as disclosed above with reference to FIGS. 3A-F, and take the frequency and power information of the first three peaks in the PSD at each window and signal segment. Embodiments disclosed herein may be based on an understanding that the heart rate component in a typical clean (motion free) PPG signal is always the dominant frequency component in the time-varying power spectrum, thus, the highest peak of the spectrum corresponds to the HR frequency. Thus, when movement happens the dominant component can be replaced by movement components which shift the HR to the second or third peak in the spectrum. As such, embodiments disclosed herein may compare the first N peaks, such as 3 peaks, disclosed above, and corresponding frequencies of the PPG spectrum to the first peak and frequency of the accelerometers' spectra at each window and choose the frequency components (out of three) that are different from the accelerometers' frequency.

Embodiments disclosed herein may be further based on an understanding that there is coherence between a spectral peak in the PPG and the accelerometers' spectra that signifies a motion noise artifact in the PPG signal and that peak should be discarded in the FIR reconstruction. After discarding these movement peaks in the spectrum, the next highest peak that is closest to the estimated HR of the previous window may be chosen at each window. By reconstructing the HR frequency at each window, simultaneously, the PPG signal may be reconstructed by using the power, frequency and phase of the signal that corresponds to the HR frequency. That is, the time-domain signals may be reconstructed from the time-frequency domain.

The SpaMA method was applied to three different datasets and 4 types of activities. The three different datasets included: 1) training datasets from the 2015 IEEE Signal Processing Cup Database recorded from 12 subjects while performing treadmill exercise from 1 km/h to 15 km/h; 2) test datasets from the 2015 IEEE Signal Processing Cup Database recorded from 11 subjects while performing forearm and upper arm exercise; and 3) Chon Lab dataset including 10 min recordings from 10 subjects during treadmill exercise.

Electrocardiogram (ECG) signals from all three datasets provided the reference HRs which were used to determine the accuracy of the SpaMA method. The performance of the SpaMA method was calculated by computing the mean absolute error between the estimated HR from the PPG and the reference HR from the ECG. The average estimation errors using the SpaMA method on the first, second and third datasets are 0.89, 1.93 and 1.38 beats/min respectively, while the overall error on all 33 subjects is 1.86 beats/min and the performance on only treadmill experiment datasets (22 subjects) is 1.11 beats/min. Moreover, it was found that dynamics of heart rate variability (HRV) can be accurately captured using the SpaMA method where the mean Pearson's correlation coefficient was found to be 0.98 between the power spectral densities of the reference and the reconstructed heart rate time series. These results show that the SpaMA method has a potential for PPG-based HR monitoring in wearable devices for fitness tracking and health monitoring during intense physical activities.

Embodiments disclosed herein not only provide PPG signal and HR reconstruction but also the potential to do heart rate variability analysis on the results. As disclosed below, embodiments disclosed herein can outperform the JOSS technique in heart rate estimation by providing less error to the reference, which yields higher accuracy.

Embodiments disclosed herein were evaluated on three different datasets. The first two datasets were provided for the IEEE Signal Processing Cup and are publically available. The three datasets are: 1.) 12 PPG training datasets (running on treadmill) from an IEEE signal processing competition (Available from: http://www.signalprocessingsociety.org/spcup2015/index.html) which was initially used in (Zhilin, Z., P. Zhouyue, and L. Benyuan, TROIKA: A General Framework for Heart Rate Monitoring Using Wrist-Type Photoplethysmographic Signals During Intensive Physical Exercise. Biomedical Engineering, IEEE Transactions on, 2015. 62(2): p. 522-531; Zhang, Z., Photoplethysmography-Based Heart Rate Monitoring in Physical Activities via Joint Sparse Spectrum Reconstruction. Biomedical Engineering, IEEE Transactions on, 2015. PP(99): p. 1-1, 2.) 11 PPG test datasets (e.g., arm exercise) from the IEEE signal processing competition and 3.) 10 PPG recordings from the Chon lab (running on treadmill).

(1) IEEE Signal Processing Competition Training Dataset: A single-channel PPG signal, a three-axis acceleration signal, and an ECG signal simultaneously recorded from 12 Asian male subjects ranging in age from 18 to 35. For each subject, the PPG signal was recorded from their wrist using a pulse oximeter (PO) with green LED (wavelength: 609 nm). The acceleration signal was also recorded from each subject's wrist using a three-axis accelerometer. Both the PO and the accelerometer were embedded in a wristband, which was comfortably worn. The ECG signal was recorded from the chest and it is used as the reference heart rate. All signals were sampled at 125 Hz.

(2) IEEE Signal Processing Competition Test Dataset: The dataset consists of 11 five minute recordings which were collected from 19 to 58 year old subjects performing intensive arm movements (e.g. boxing). For each subject, PPG signals were recorded with a sensing location at the wrist using a pulse oximeter with green LEDs (wavelength: 515 nm). The acceleration signal was also recorded from at the sensing location at the wrist using a three-axis accelerometer. Both the PO and the accelerometer were embedded in a wristband. An ECG signal was recorded simultaneously from each subject's chest using wet ECG sensors. All signals were sampled at 125 Hz and sent to a nearby computer via Bluetooth.

(3) Chon Lab Dataset: This dataset was recorded in the Chon Lab from 10 healthy subjects (9 male/1 female), with ages ranging from 26 to 55. For each subject, the PPG signal was recorded from their forehead using a PO with red and infrared LED (wavelength: 660 and 940 nm). The acceleration signal was also recorded from each subject's forehead using a three-axis accelerometer. Both the pulse oximeter and the accelerometer were embedded in a headband and the signals were sampled at 80 Hz. The ECG signal was recorded as a reference from the chest using ECG sensors, sampled at 400 Hz. During data recording, the subjects walked, jogged and ran on a treadmill with speeds of 3, 5 and 7 mph, respectively, for 9 min. At the end, all experimental subjects were asked to perform random arbitrary movements for 1 min.

For all three datasets, the data was down-sampled to 20 Hz since the estimation of heart rate is carried out in the frequency domain and this sampling rate is sufficiently high to obtain even heart rates that are as high as 240 beats/min or 4 Hz. Moreover, this down-sampling enables a focus on heart rates in the lower frequencies rather than in the physiologically irrelevant higher frequency ranges. Further details of this study's databases are given in Table 4, below. Four types of activities were involved:

Type (1): activity involved walking or running on a treadmill for intervals of 0.5 min-1 min-1 min-1 min-1 min-0.5 min with speeds of 1-2 km/h, 6-8 km/h, 12-15 km/h, 6-8 km/h, 12-15 km/h, 1-2 km/h, respectively. The subjects were asked to purposely move the hand with the wristband to generate motion artifacts.

Type (2): activity included various forearm and upper arm exercise which are common arm motions (e.g., shaking hands, stretching, pushing objects, running, jumping, and push-ups).

Type (3): activity consisted of intensive forearm and upper arm movements (e.g., boxing).

Type (4): activity involved 1 min rest, 1 min walking (3 mph), 1 min rest, 2 min jogging (5 mph), 1 min rest, 2 min running (7 mph), 1 min rest, 1 min arbitrary movement. The ECG-based reference HR was recorded in order to assess the performance of the methods under test.

In summary, the first dataset includes only Type (1) activities, the second dataset includes both Type (1) and (2) activities, and the third dataset includes only Type (4) activities.

TABLE 4

PPG Datasets and Experiments Settings

| Subject | Dataset | Activity Type | Pulse Oximeter Type | Subject's Age/Sex |
|---|---|---|---|---|
| 1 | 1 (IEEE Cup) | Type (1) | Wrist: green LED (wavelength: 609 nm) | 18-38 y (All Male) |
| 2 | | | | |
| 3 | | | | |
| 4 | | | | |
| 5 | | | | |
| 6 | | | | |
| 7 | | | | |
| 8 | | | | |
| 9 | | | | |
| 10 | | | | |
| 11 | | | | |
| 12 | | | | |
| 13 | 2 (IEEE Cup) | Type (2) | Wrist: green LED (wavelength: 515 nm) | 19-58 y (9 Male, 1 Female) |
| 14 | | | | |
| 15 | | | | |
| 16 | | Type (3) | | |
| 17 | | | | |
| 18 | | | | |
| 19 | | | | |
| 20 | | Type (2) | | |
| 21 | | Type (3) | | |
| 22 | | | | |
| 23 | | Type (2) | | |
| 24 | 3 (Chon Lab) | Type (4) | Forehead: Red and Infrared LED (wavelength: 660 nm, 940 nm) | 26-55 y (9 Male, 1 Female) |
| 25 | | | | |
| 26 | | | | |
| 27 | | | | |
| 28 | | | | |
| 29 | | | | |
| 30 | | | | |
| 31 | | | | |
| 32 | | | | |
| 33 | | | | |

An example embodiment for reconstructing a heart-related signal during intensive movements is disclose by the HR monitoring method presented below in Table 5. Details of each stage are described in subsections i to v.

TABLE 5

HR and PPG signal reconstruction method

Stage 1. Time-Varying Spectral analysis
    1.1. Down sample the PPG and Accelerometer signal to 20 Hz.
    1.2. Compute the power spectral density of both PPG and Accelerometers [0-10 Hz].
Stage 2. Spectral Filtering
    2.1. Assume HR to be in the frequency range of [0.5 Hz-3 Hz], this accounts for both low and high heart rates.
    2.2. The first highest three peaks and their corresponding frequencies in the PPG filtered spectrum are assumed to have HR information.
    2.3. Only the largest frequency peak of the accelerometers' spectra is used for MA detection in stage 3.
Stage 3. Motion Artifact Detection
    3.1. Compare the frequencies of the three peaks in the PPG spectrum with the frequency of the largest peak in the accelerometers' spectra. If the first or second largest peaks in the PPG spectrum are similar to that of the accelerometers' peaks, then motion artifact is present in the PPG.
    3.2. If motion artifact is detected from 3.1, then the corresponding frequency peak (usually the first or second largest peak) in the PPG spectrum should be discarded.
Stage 4. Heart Rate Tracking and Extraction from PPG Spectrum
    Case (1): From 3.1- if the spectrum is corrupted by movement and only the first largest peak is corrupted, then the HR frequency should be the frequency of the second peak in the spectrum.
    Case (2): From 3.1- if the spectrum is corrupted by movement and both the first and second largest peaks have similar frequencies to those of the accelerometers' peaks, then the HR frequency should be the frequency of the third peak in the spectrum.
    Case (3): Due to a gap between the pulse oximeter and a subject's skin, the HR frequency cannot be extracted from the spectrum and in this case the previous HR frequency is used or for offline implementation a cubic spline interpolation can be applied to fill in the missing HR information.
Stage 5. PPG Signal Reconstruction
    5.1. The PPG signal is reconstructed by using the amplitude, frequency and phase information corresponding to the HR components (extracted in stage 4) that are calculated from the spectrum at each window.
    Heart Rate Variability Analysis
    By using a sample-by-sample windowing strategy, HR can be extracted, from which dynamics of heart rate variability analysis can be obtained on the motion artifact-removed reconstructed HR time series.

I. Time-Varying Spectral Analysis of PPG and Accelerometer Data

Embodiments disclosed herein may produce a time-varying spectrum by taking a T-sec window of the signal and computing the power spectral density (PSD) of the segment and then sliding the window through the whole dataset which yields a time-frequency matrix in which each array represents the power of the signal corresponding to a specific frequency and sliding time-step (shift) of S-sec. The sliding process and frequency step specify the resolution and dimension of the time-frequency matrix. According to embodiments disclosed herein, two different sliding window approaches may be used, depending on the application. For estimating either heart rates or heart rate variability, data may be shifted sample-by-sample with no overlap for the entire dataset. Such an approach enables capturing beat-to-beat dynamics of HRV which requires sample-to-sample estimation of PSD. Since some data is down-sampled data to 20 Hz in some of the database, as disclosed above, each data point may be shifted by 0.05 seconds. For estimating only the heart rates, the shift may be a data segment-by-segment shift rather than a sample-by-sample shift. This coarse-grain windowing approach has less computational cost and it can provide good tracking of heart rates, but does not apply well to HRV.

As such, according to some embodiments, a window segment length T may be set to 8 seconds and shifted by 2 seconds. The 8 second data segment and a shift of 2 seconds was chosen to compare results according to embodiments disclosed herein to other methods (TROIKA, JOSS and WFPV) which have used this chosen data segment length and time shift (Zhilin, Z., P. Zhouyue, and L. Benyuan, TROIKA: A General Framework for Heart Rate Monitoring Using Wrist-Type Photoplethysmographic Signals During Intensive Physical Exercise. Biomedical Engineering, IEEE Transactions on, 2015. 62(2): p. 522-531; Zhang, Z., Photoplethysmography-Based Heart Rate Monitoring in Physical Activities via Joint Sparse Spectrum Reconstruction. Biomedical Engineering, IEEE Transactions on, 2015. PP(99): p. 1-1). Moreover, the assumption of 8 second data length largely stems from the fact that heart rates do not change instantaneously, hence, an 8 second duration is a reasonable choice.

Figure 6A:
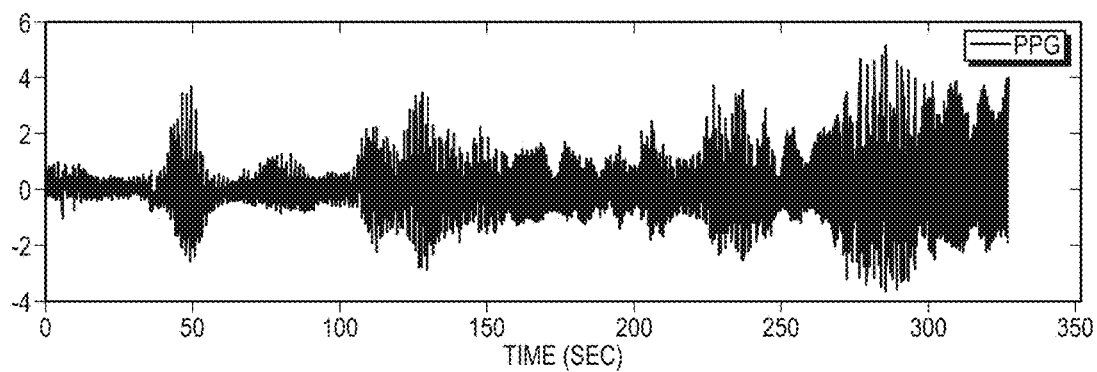
FIGS. 6A-6C show Time-Frequency spectra of a recording from a dataset.

As a representative example, the resultant frequency components in the time-frequency matrix of recordings from subject #8 from the competition training dataset, for a window length of 8 seconds that is shifted by every 2 seconds, is shown in FIG. 6A, disclosed below.

Figure 6B:
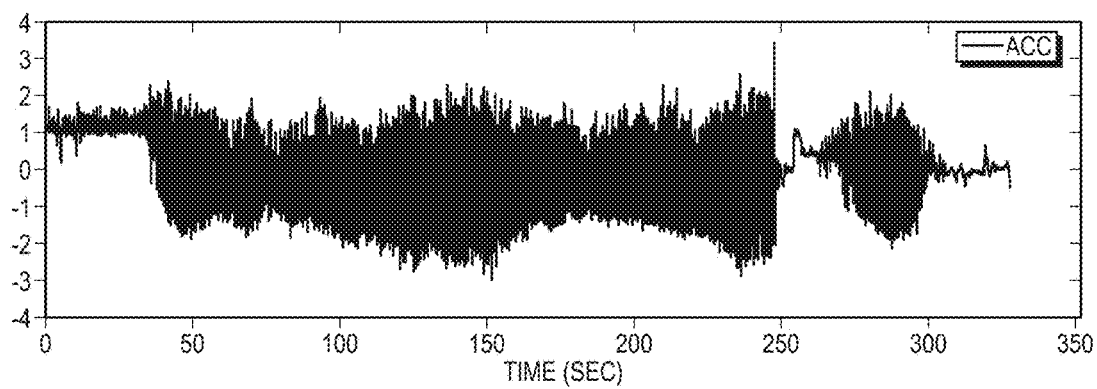
Figure 6C:
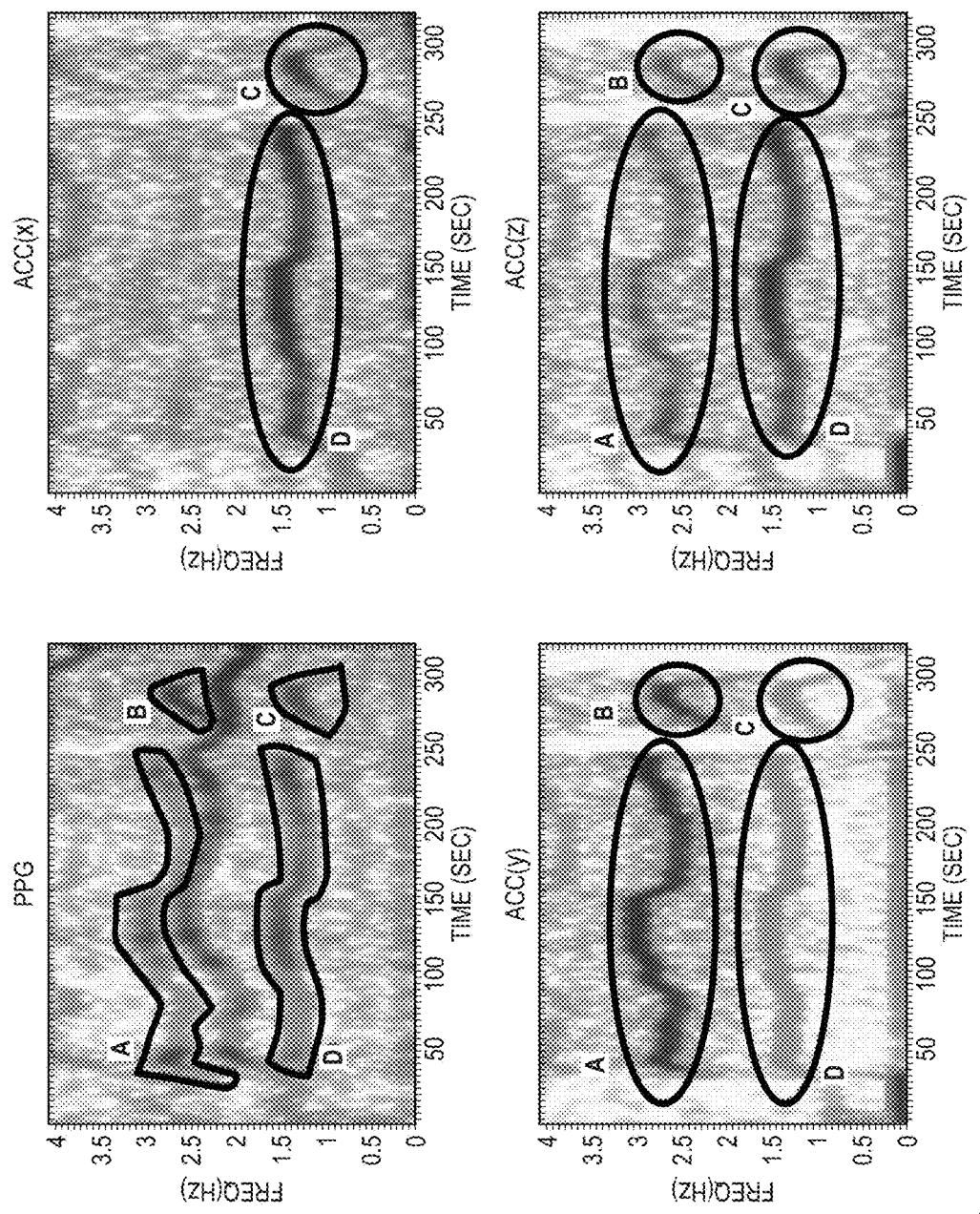

FIGS. 6A-6C show Time-Frequency spectra of recording #8 from dataset (1).

FIG. 6A shows the PPG signal.

FIG. 6B shows the simultaneous Accelerometer-Z signal.

FIG. 6C (Top-Left) shows the TF spectrum of the PPG signal. FIG. 6C (Top-Right) shows the TF spectrum of ACC(x). FIG. 6C (Bottom-Left) shows the TF spectrum of ACC(y). FIG. 6C (Bottom-Right) shows the TF spectrum of ACC(z); all computed from stage (1) of Table 5. The blue circles and letters represent movement elements in all four spectra.

The panels of FIG. 6A and FIG. 6B show a PPG time series and the z-axis accelerometer data, respectively. From the upper left panel of FIG. 6C, which represents the time-frequency plot of the PPG signal, it is observed that there are three dominant frequency components—one of them represents HR and the other two are similar to those of the accelerometers' spectra shown in the upper right and lower left and right panels of FIG. 6C. FIG. 6C illustrates 4 motion artifact elements (A, B, C, D) that are present in exactly the same areas among all spectra. By comparing the time-frequency (TF) spectrum of PPG to those of the accelerometers' spectra, the marked dynamics (A, B, C and D) in the PPG spectrum can be detected as sharing the same frequency dynamics as those of the accelerometer spectra marked in circles. Hence, both the top and bottom marked lines in the PPG spectrum most likely represent the motion artifacts, and the unmarked frequency represents the HR. The next section details how these motion artifact frequency dynamics may be detected and filtered according to embodiments disclosed herein.

II. Spectral Filtering

After obtaining the power spectral density at each window, as disclosed above, embodiments disclosed herein may confine the HR frequency to the range [0.5 Hz-3 Hz], which takes into account both at rest and high HR due to either tachycardia or exercise scenarios. Hence, for HR estimation, the strategy is to eliminate frequencies that are outside of this HR frequency range as they are most likely due to motion artifacts or harmonics of the FIR frequency.

In general, HR frequency in the power spectral density of PPG at each window can have three different scenarios: (1) PPG is devoid of MA and there is no spatial gap between the sensor and the subject's skin during recording, (2) PPG is corrupted by MA and there is no spatial gap between the sensor and the subject's skin during recording and (3) There is a spatial gap between the sensor and the subject's skin during recording. For the ideal case (1), HR can be extracted and it is most likely represented as the highest peak in the PPG spectrum. For case (2), MA dynamics can result in predominately either one or two dominant peaks depending on the severity of repetitive motions, and the HR peak may be relegated to either the second or third highest peak. Non-repetitive motion artifacts will show up as a broadband spectrum without a dominant peak if they are not severe (Marmarelis, V. Z., et al., Nonlinear analysis of renal autoregulation under broadband forcing conditions. Ann Biomed Eng, 1993. 21(6): p. 591-603). The only scenario that makes it difficult to extract HR from the spectrum is scenario (3) when there is a spatial gap between the PPG sensor and the subject's skin during recording. In this scenario, assuming that the motion artifacts are short lasting, the missing HR values can be interpolated using a cubic spline approach.

Figure 7:
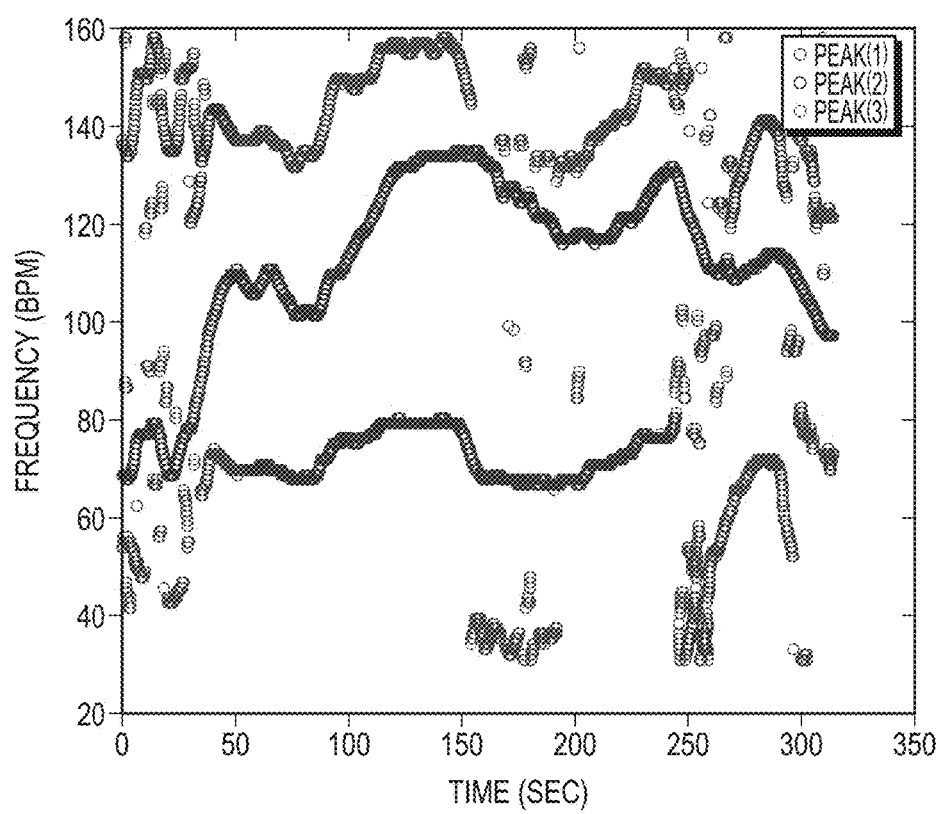
FIG. 7 is a filtered time-frequency spectral plot of a photoplethysmogram (PPG) signal.

FIG. 7 is an example embodiment of spectral filtering. FIG. 7 shows a representative filtered time-frequency spectral plot of a PPG signal. As disclosed above, embodiments disclosed herein may retain only the three largest frequency peaks at each time point within the defined HR range (30-180 bpm) and such retained frequency peaks are represented as blue, green and red colors, respectively. Retaining only the three largest frequency peaks at each time point may be reasonable for the first two cases, as outlined above. In the PPG time-frequency spectrum of FIG. 7, the Blue, Green and Red circles correspond to the first three highest peaks in the defined HR frequency range of (30-180 bpm), respectively, at each sliding window.

III. Motion Artifact Detection

Figure 8A:
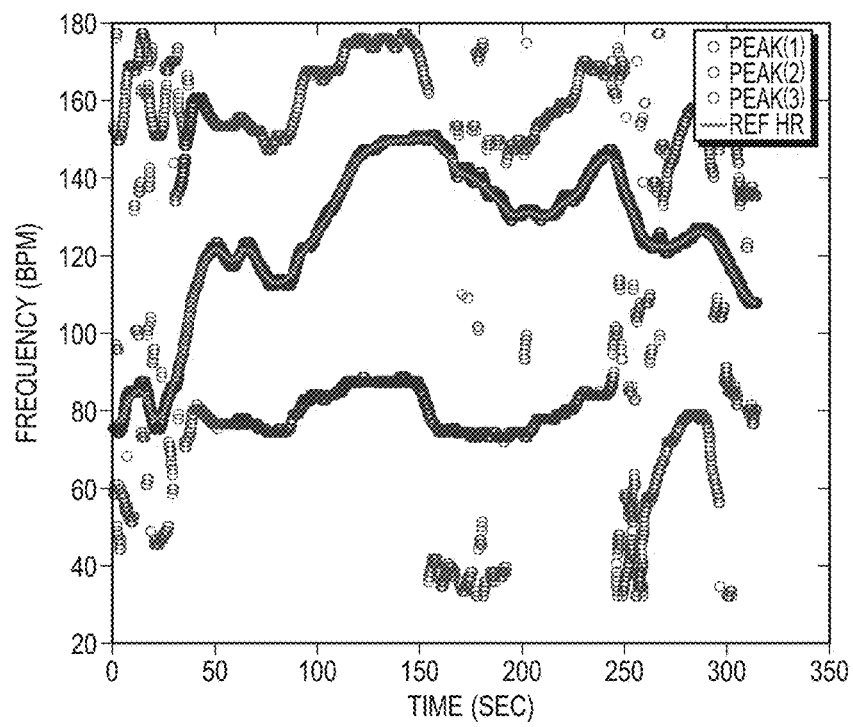
FIGS. 8A-8B show motion artifact detection in a PPG spectrum according to embodiments disclosed herein.
Figure 8B:
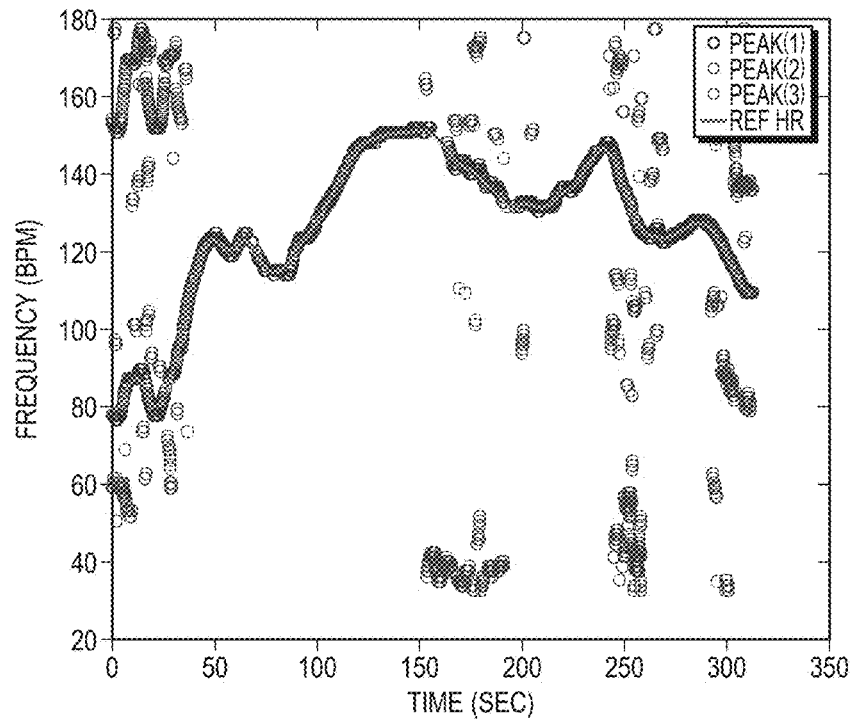

FIGS. 8A-8B show motion artifact detection in the PPG spectrum according to embodiments disclosed herein.

FIG. 8A shows a filtered PPG spectrum with movement and HR components. FIG. 8A is an example embodiment of a PPG spectrum which is identical to FIG. 7, but it also identifies the frequencies associated with accelerometers, as marked by the shaded areas and the letters A-D, in the top left and two bottom panels of FIG. 6C, disclosed above. The shaded yellow elements (A, B, C, D) of FIG. 8A represent motion frequency components in the PPG spectrum, and the light blue line is the reference HR from a clean reference ECG signal. By removing the accelerometers' related frequencies in FIG. 8A, the remaining frequency dynamics which should represent HR frequency and its harmonics are shown in FIG. 8B.

FIG. 8B shows a filtered PPG spectrum after removing motion artifact frequency components.

IV. Heart Rate Tracking & Extraction

A flow diagram for heart rate tracking and extraction is disclosed above, with reference to FIG. 3B. Embodiments disclosed herein may identify HR frequencies with time, such as HR frequencies from FIG. 8B. Note that in FIG. 8B, there are three peaks at each time instance (also referred to interchangeably herein as a time point). Embodiments disclosed herein may identify which of the three peaks represents the HR at each time point. For the initial time window of 8 seconds, a clean data segment may be used so that true HR can be determined. This scenario is case (1), disclosed above, in the spectral filtering section, and the detection of HR is simply the highest peak in the spectrum. Embodiments disclosed herein may estimate FIR for each sliding window of data. Embodiments disclosed herein may choose a HR peak in the PPG spectrum with the knowledge of estimated HR values in previous time windows. Two main scenarios may present: (1) no peak exists in the spectrum that can represent HR, and (2) there is a spectral peak among the first three highest peaks of spectrum that belongs to the HR component.

In case (1), where HR is not detectable in the window (e.g., due to spatial gap between the PO sensor and skin), in real-time implementation embodiments disclosed herein may take a previous window's HR value as the current HR (or simply use a moving average of several past HR beats or some other variant). In post-processing, or offline processing, a cubic spline interpolation may be used to fill in the missing HR information. In the more general case (2), where the HR peak is among the first three highest peaks in the spectrum, three possible scenarios can occur: (2-A) the windowed PPG signal is clean and the first highest peak in the spectrum represents the HR fundamental frequency, (2-B) the windowed PPG signal is corrupted by movement and at most two of the spectral peaks represent the accelerometers' frequency components, thus, the second or the third peak corresponds to HR, (2-C) while the HR spectral peak is detectable, the difference between its value and that of the previous HR is more than 10 bpm, as such, embodiments disclosed herein may replace the HR by the most recent HR value from a previous window segment (or a moving average of several past HR beats or some other variant).

According to embodiments disclosed herein, criterion may be set that the HR value cannot change more than 10 BPM from a previous time window. In FIG. 8B, these cases are illustrated. For example, in most cases, the blue circle which represents the largest spectral peak is chosen but in other cases, either green or red circles are chosen for certain time points. For the HR peaks associated with either the green or red circles, embodiments disclosed herein may choose those peaks because either the first two highest peaks are related to accelerometers or the highest magnitude peak deviates more than 10 BPM from the previous HR value.

Figure 9:
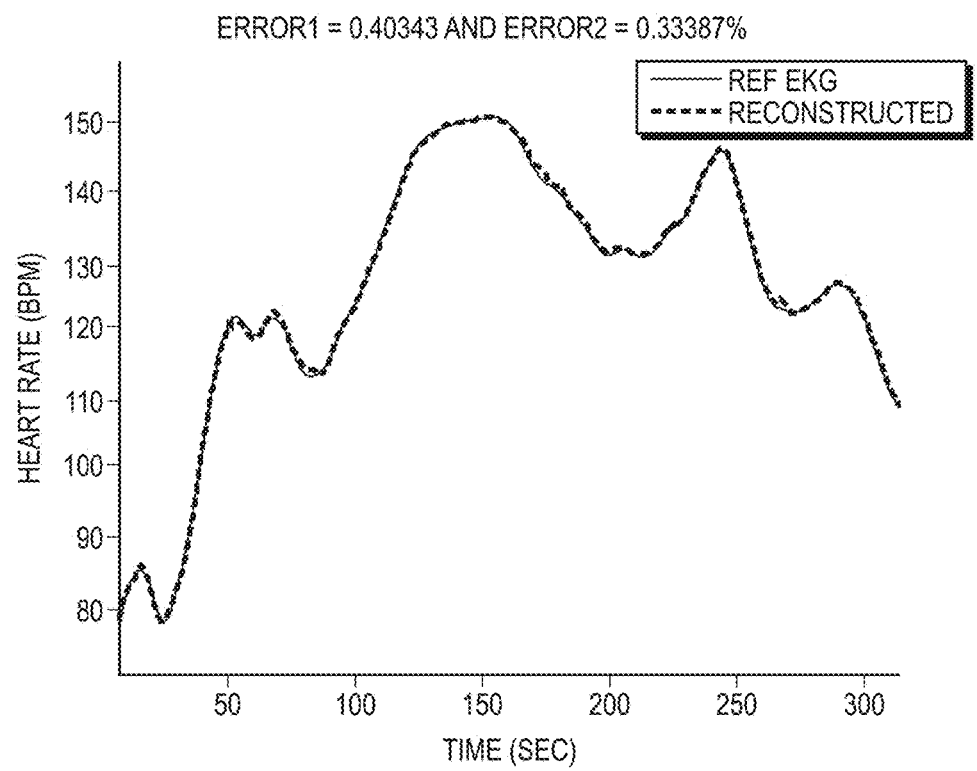
FIG. 9 shows a comparison of reconstructed heart rate (HR) obtained, according to embodiments disclosed herein, to reference HR obtained from simultaneous electrocardiogram (ECG) recordings.

FIG. 9 shows a comparison of reconstructed FIR obtained, according to embodiments disclosed herein, to reference HR obtained from simultaneous ECG recordings. In FIG. 9, the extracted HR (red color) from PPG spectra of recording#8 from the competition training dataset, according to embodiments disclosed herein, is shown in red color and the reference ECG-derived HR is shown in black color. In order to calculate the performance of FIR reconstruction according to embodiments disclosed herein, the error value in each time window was calculated from the estimated FIR to the reference ECG-derived HR. Two measurement indices of absolute error similar to the indices in (Krishnan, R., B. Natarajan, and S. Warren, Two-Stage Approach for Detection and Reduction of Motion Artifacts in Photoplethysmographic Data. Biomedical Engineering, IEEE Transactions on, 2010. 57(8): p. 1867-1876) were used.

$$\text{Error}(1) = \frac{1}{W}\sum_{k=1}^{w} |HR_{SpaMA}(k) - HR_{ref}(k)| \qquad (1)$$

$$\text{Error}(2) = \frac{1}{W}\sum_{k=1}^{w} \frac{|HR_{SpaMA}(k) - HR_{ref}(k)|}{HR_{ref}(k)} \times 100\% \qquad (2)$$

where W is the total number of windows.

v. PPG Signal Reconstruction for HRV Analysis

For an HRV analysis application, the above-disclosed embodiments are identical except that the beat-by-beat shift is of data rather than the 8 second data segment shift or its variant. According to embodiments disclosed herein, the PPG signal may be reconstructed using heart rate frequency, amplitude and phase changes, window-by-window using the sample-by-sample windowing process:

$$Rec_{signal} = A_{HR}(k) \times \sin(2\pi t(k) f_{HR}(k) + \varphi_{HR}(k)) \qquad (3)$$

where k=1, . . . , N and N is number of signal samples and total number of windows. $A_{HR}(k)$ and $\varphi_{HR}(k)$ are calculated according to the power of the signal for HR frequencies in the PSD and phase angles of complex elements in a Fast Fourier Transform (FFT) matrix that correspond to HR frequencies.

Figure 10A:
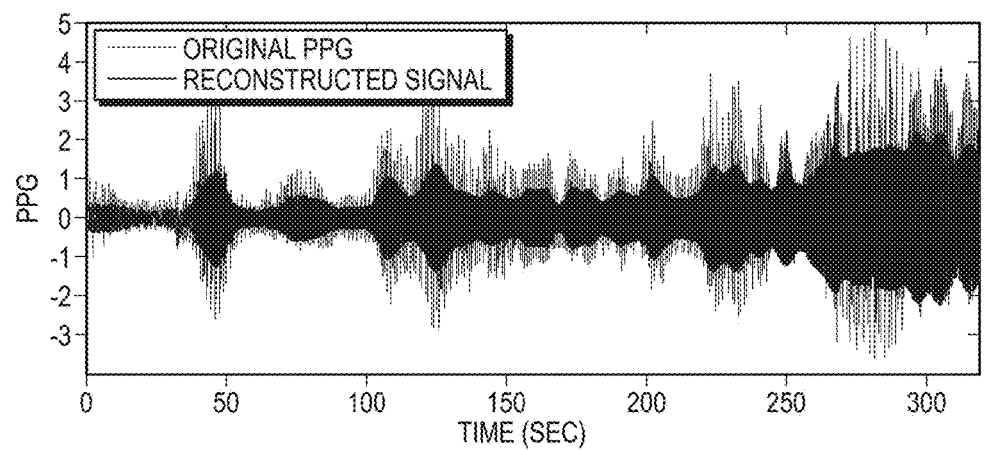
FIG. 10A is an example embodiment of PPG signal reconstruction according to embodiments disclosed herein.

FIG. 10A is an example embodiment of PPG signal reconstruction according to embodiments disclosed herein. FIG. 10A shows a comparison between reconstructed PPG and original recording #8 from IEEE competition training dataset. The left and right panels of FIGS. 10A-B show the reconstructed PPG versus the original PPG and their HRV time series, respectively.

Figure 10B:
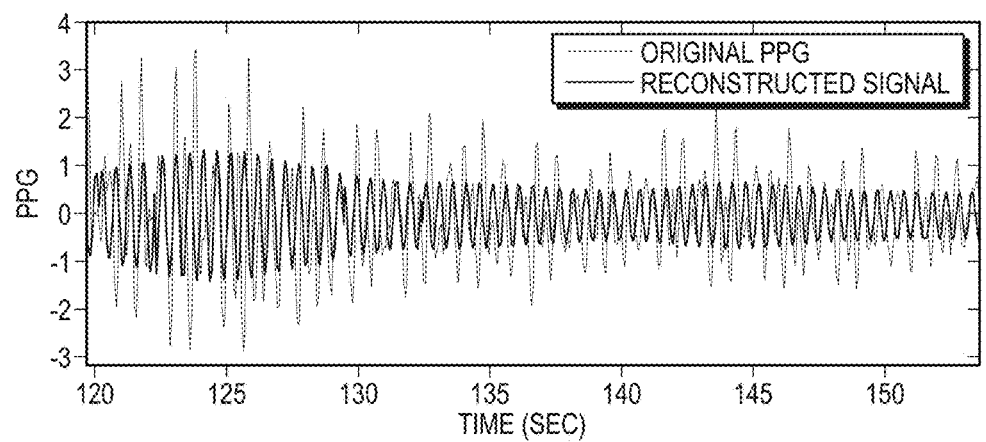
FIG. 10B is a zoomed-in version of FIG. 10A.

FIG. 10B is a zoomed-in version of FIG. 10A.

Given that embodiments disclosed herein estimate quite accurate heart rates, it is not surprising to observe similar frequency dynamics between the reference and reconstructed HRV time series, as shown in FIGS. HA-B.

Figure 11A:
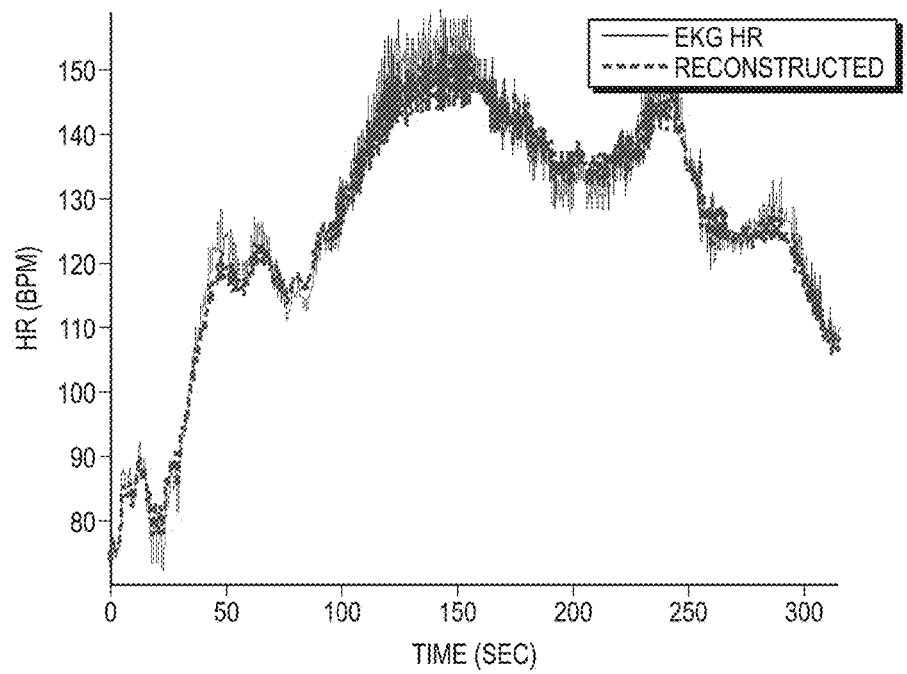
FIGS. 11A-B show comparisons of heart rate variability (HRV) spectra between a reference and a reconstructed HRV time series (e.g., as shown in FIGS. 10A-B) from a motion artifact-contaminated PPG signal for a given dataset.
Figure 11B:
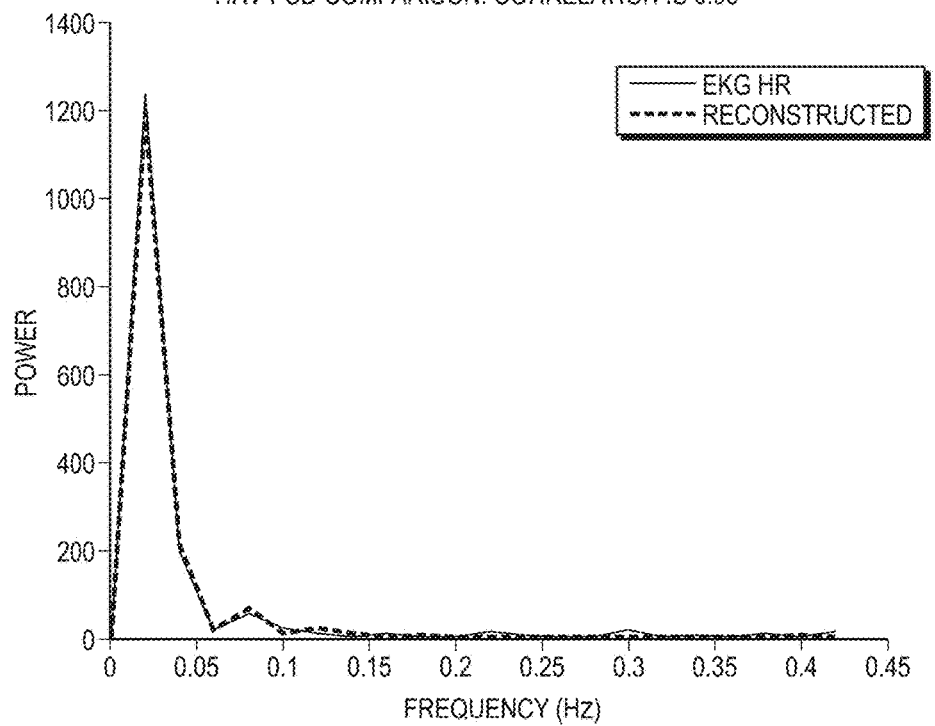

FIGS. 11A-B show comparisons of HRV spectra between the reference and the reconstructed HRV time series (e.g., as shown in FIGS. 10A-B) from the MA-contaminated PPG signal for dataset #8. Note that for computing HRV, matching the amplitude of the reference HR is not a concern, as the focus is only in the dynamics of the fluctuations in the heart rates.

FIG. 11A shows a time-domain comparison of a reconstructed HR and a reference HR.

FIG. 11B shows a spectral comparison of heart rate variability between reconstructed HR and reference HR calculated from the reference ECG using Pan & Tompkins peak detection approach (Pan J, T. W A real-time QRS detection algorithm. IEEE Trans Biomed Eng, 1985. 32(3): p. 230-236).

Results

Figure 11C:
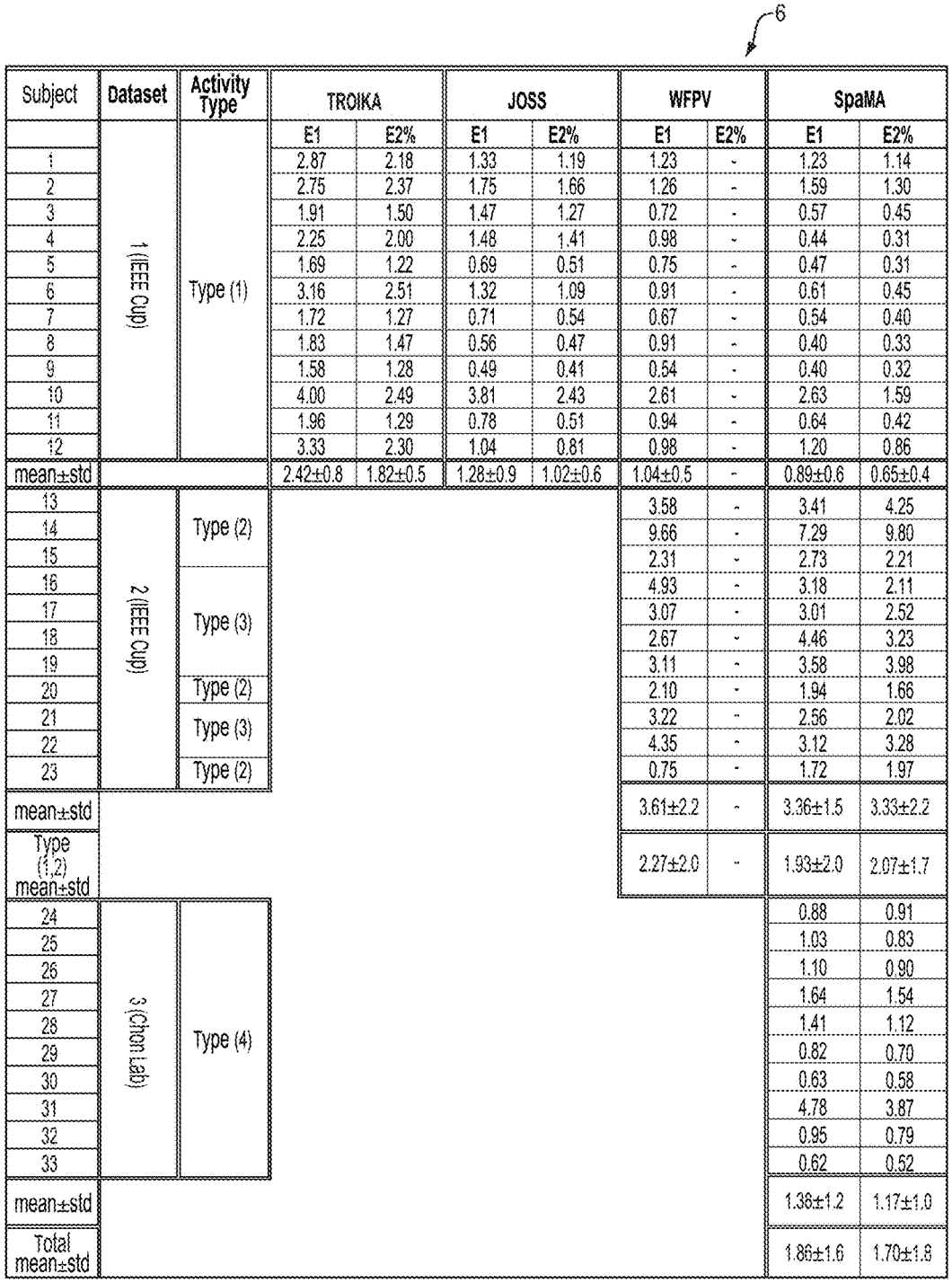
FIG. 11C is a performance comparison table of a spectral approach for filtering motion artifacts (SpaMA) method to alternative methods.

FIG. 11C is a "SpaMA Method Performance Comparison" table, Table 6, also referred to interchangeably herein as Table 6. Table 6 represents the average absolute error (E1) and the average absolute error percentage (E2) of embodiments disclosed herein as applied to all 3 datasets, respectively. Embodiments disclosed herein are compared to three methods: TROIKA, JOSS and WFPV. The results in Table 6 show that better performance from embodiments disclosed herein as compared to JOSS and TROIKA for all 12 subjects in the first datasets. In comparison to WFPV, embodiments disclosed herein outperform WFPV on average across all 23 subjects in both datasets (1) and (2). The total average of E1 for embodiments disclosed herein is less than 2 beats per minutes for all 33 subjects. The average of E1 across the treadmill experiment recordings (activity Type 1—IEEE dataset and Type 4—Chon Lab dataset) is around 1 beat per minute for all 22 subjects.

Figure 12A:
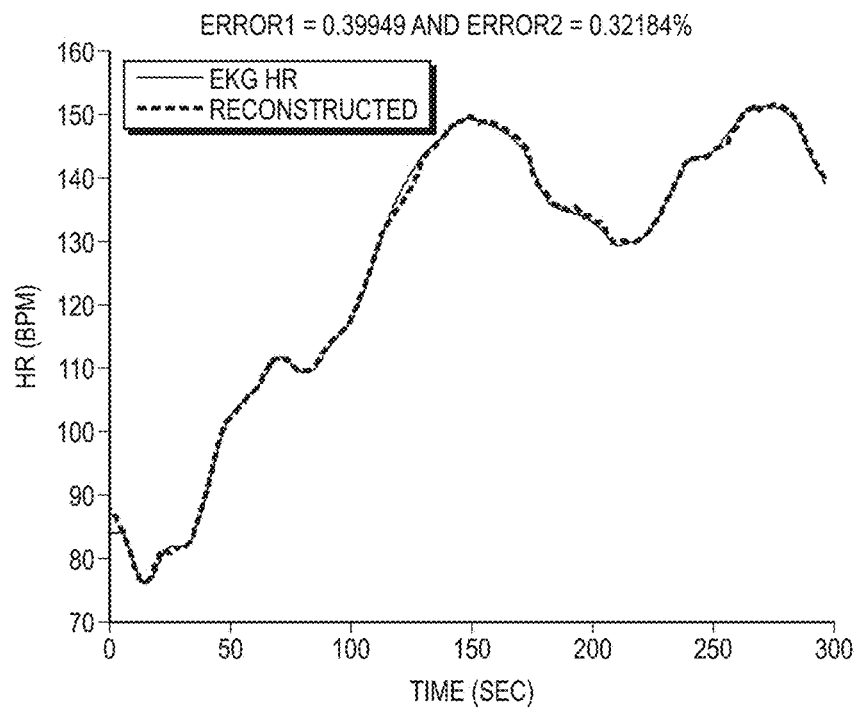
FIGS. 12A, 12B, 13A, 13B, 14A, and 14B show the reconstructed HR and corresponding power spectral density (PSD) of a sample-sample windowed HR, according to embodiments disclosed herein, in comparison to a reference HR from an ECG.
Figure 12B:
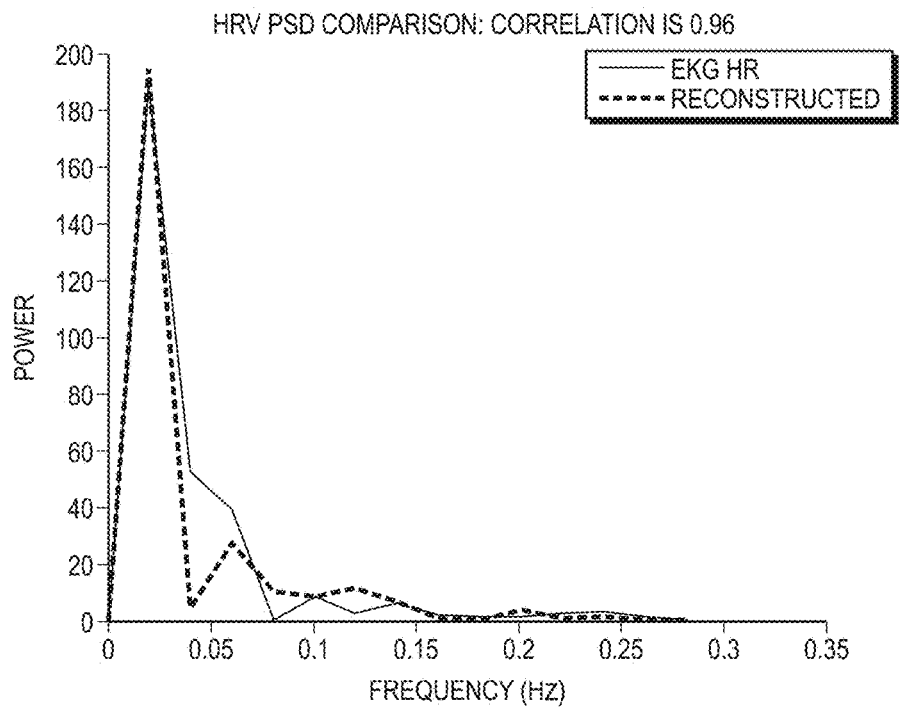
Figure 13A:
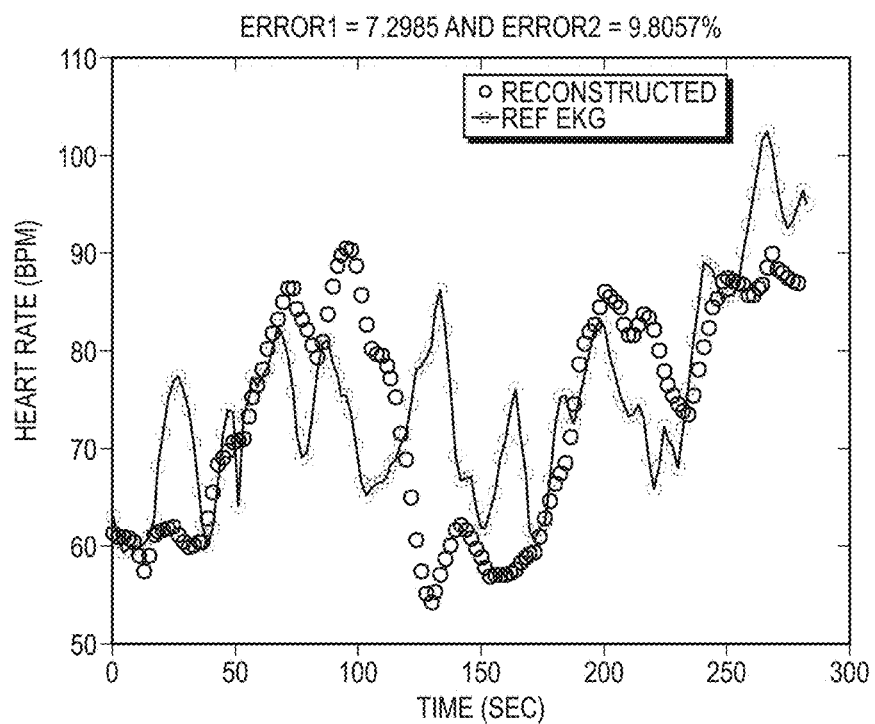
Figure 13B:
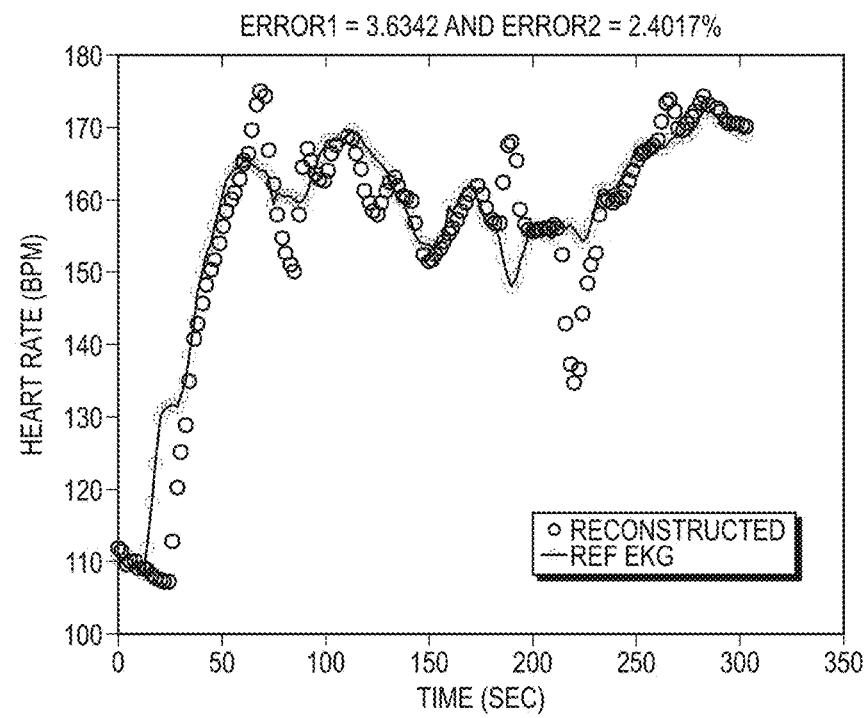

FIGS. 12A, 12B, 13A, 13B, 14A, and 14B show the reconstructed HR and corresponding PSD of a sample-sample windowed HR, according to embodiments disclosed herein, in comparison to a reference HR from an ECG. The results for recording #9 from the first dataset (IEEE Competition Training dataset) and activity Type 1 (e.g., running on treadmill) are shown in FIGS. 13A-B. As shown, E1 for this particular subject is as low as 0.4 bpm and the correlation between the PSD of reconstructed HR and reference HR is as high as 96%.

FIG. 12A shows a reconstructed HR vs. reference HR. FIG. 12B shows a spectral comparison of reconstructed HR and reference HR (estimated from reference ECG).

FIG. 13A illustrates the comparison between the reconstructed HR and the reference HR for Subject #14 (IEEE Competition Test Dataset) which has the highest errors. Subject #14 belongs to the second dataset (IEEE Competition Test dataset) and Type 2 activities (e.g. jumping). It can be seen that the largest error is obtained when both the physiological HR and the motion artifacts change rapidly so that the true HR cannot be reliably estimated.

FIG. 13B shows a reconstructed HR vs. reference HR for Subject 16 (IEEE Competition Test Dataset). FIG. 13B shows the comparison results of reconstructed HR and reference HR for recording #16 of the second dataset (IEEE Competition Test dataset) which has the Type 3 activities (e.g., arm exercise).

Figure 14A:
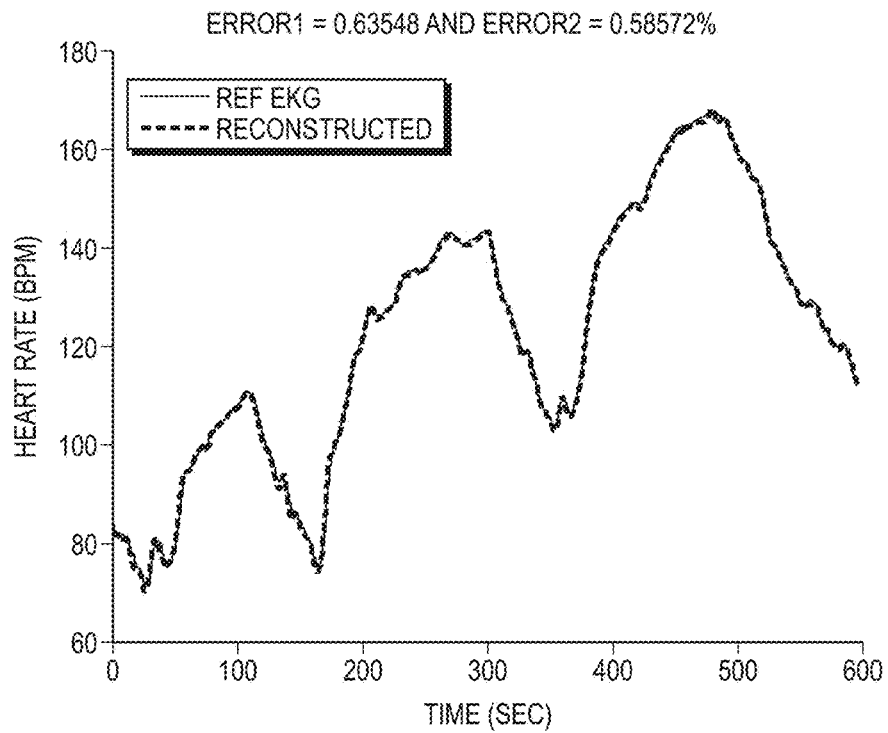
Figure 14B:
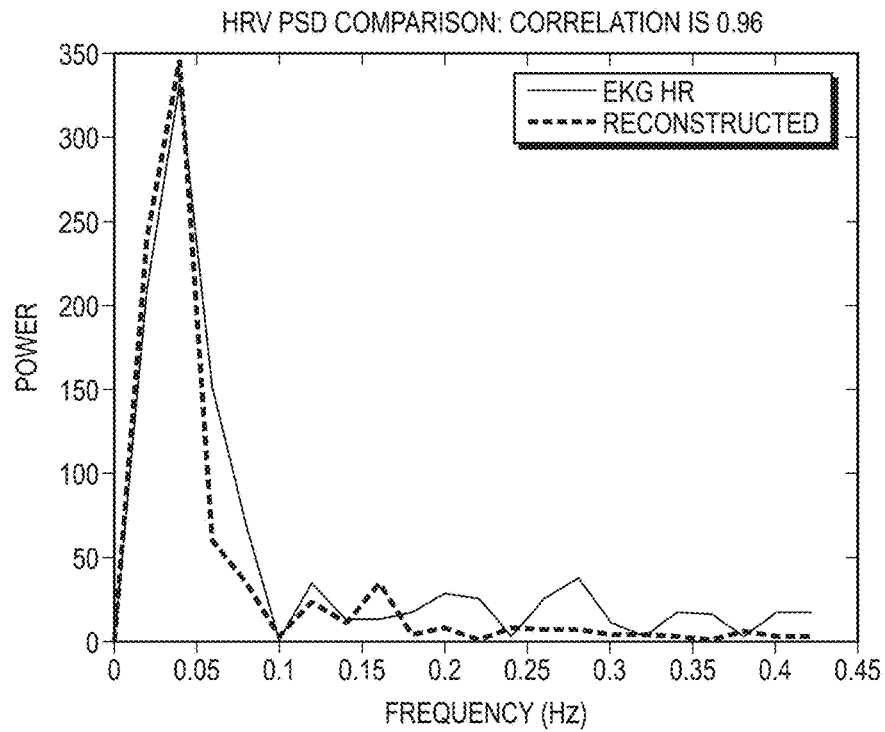

FIG. 14A shows a reconstructed HR vs. reference HR for Subject #30 (Chon Lab Dataset). FIG. 14B shows a spectral comparison of reconstructed HR and reference HR (estimated from reference ECG). The results for recording #30 from the third datasets (Chon Lab datasets) and activity Type 4 (e.g., running on treadmill) are shown in FIGS. 14A-B. It can be seen that the E1 for this subject is around 0.6 bpm and the correlation between the PSD of reconstructed HR and reference HR is as high as 99% for LF and 0.96 for HF frequency range. All subjects' results are provided in Table 7, disclosed below.

Table 7 represents the correlation and statistical difference using the student's t-test between PSD of estimated and reference HRV in both LF (0.04-0.15 Hz) and HF (0.15-0.4 Hz) frequency ranges. The correlation values in the table are calculated based on Pearson's linear correlation coefficient. As shown in Table 7, there was no difference between the reference and the derived HRV for LF, according to embodiments disclosed herein, and a difference was seen in only 4 out of 10 subjects for HF.

TABLE 7

Frequency Domain HRV analysis Comparison:
PSD of SpaMA Method vs. reference

| Subjects | Correlation LF (LF is [0.04-0.15] Hz and HF is [0.15-0.4] Hz) | HF |
|---|---|---|
| 1 | 0.99 | 0.98 |
| 2 | 0.99 | 0.96 |
| 3 | 0.99 | 0.95* |
| 4 | 1.00 | 0.99 |
| 5 | 1.00 | 0.99 |
| 6 | 0.99 | 0.96* |
| 7 | 0.98 | 0.92* |
| 8 | 0.97 | 0.90* |
| 9 | 1.00 | 0.99 |
| 10 | 1.00 | 0.99 |
| mean | 0.99 | 0.96 |

*indicates significantly different (P-value > 0.05)

Table 8 shows some of the widely-reported time-domain HRV parameters such as the mean HR, standard-deviation (SDNN) of the normal-to-normal (NN) interval, root-mean-square of successive difference (RMSSD) of the NN interval, and the number of interval differences of successive NN intervals greater than 50 ms divided by the total number of NN intervals (pNN50) estimated from embodiments disclosed herein in comparison to the reference ECG NN interval. None of these parameters were found to be significantly different between those derived according to embodiments disclosed herein and the reference HRV.

sive physical activities. Embodiments disclosed herein compare spectral changes in PPG and accelerometer signals. As disclosed above, three different datasets have been used to verify the SpaMA performance. Each dataset reflects different types of activities and movements. In all of the experiments, the reference HR was calculated from an ECG signal that was collected simultaneously with the PPG signal. The estimated HR was calculated from the spectrum of PPG in 8 second time windows. Based on the results, disclosed above, the SpaMA method may be used for tracking HR changes during severe motion artifacts with an average error of just 1.86 bpm compared to that of the reference ECG; these results are superior to three other methods tested: TROIKA, JOSS and WFPV (Zhilin, Z., P. Zhouyue, and L. Benyuan, TROIKA: A General Framework for Heart Rate Monitoring Using Wrist-Type Photoplethysmographic Signals During Intensive Physical Exercise. Biomedical Engineering, IEEE Transactions on, 2015. 62(2): p. 522-531; Zhang, Z., Photoplethysmography-Based Heart Rate Monitoring in Physical Activities via Joint Sparse Spectrum Reconstruction. Biomedical Engineering, IEEE Transactions on, 2015. PP(99): p. 1-1).

Out of 33 recordings, 23 are from a wrist pulse oximeter, and the rest of the data were recorded by a forehead pulse oximeter. The results from Table 8, disclosed above, show that the SpaMA method can be applied to monitor HR from both wrist and forehead pulse oximeters. By comparing the performance of the method for treadmill experiments (dataset 1 and dataset 3), the error is lower by almost 1 beat using a wrist pulse oximeter. However, it should be noted that from this result a conclusion that the wrist PPG provides less error than the forehead should not be drawn, as the experiments used different subjects and were two separate studies. The prior methods (TROIKA, JOSS and WFPV) were tested using only on the wrist-based PPG signals as the implementers of those methods did not have access to forehead PPG sensors. The SpaMA method, according to embodiment disclosed herein, was tested on data from both PPG sensor locations, and proved to be effective regardless of the location of the PPG sensor.

Several observations were made while analyzing the data, disclosed above. The tracking ability of the SpaMA method decreased as the frequency changes during recordings

TABLE 8

Time Domain HRV analysis Comparison: SpaMA Method vs. reference HRV

| | SDNN | | meanNN | | RMSSD | | pNN50 | |
|---|---|---|---|---|---|---|---|---|
| Subjects | SpaMA | Reference | SpaMA | Reference | SpaMA | Reference | SpaMA | Reference |
| 1 | 2620.75 | 2566.47 | 10481.89 | 10480.72 | 33.24 | 18.05 | 0.001 | 0.020 |
| 2 | 2115.44 | 2079.58 | 9908.00 | 10020.00 | 25.93 | 16.32 | 0.011 | 0.019 |
| 3 | 3173.73 | 3177.68 | 10764.20 | 10829.06 | 89.70 | 56.15 | 0.019 | 0.207 |
| 4 | 2517.78 | 2533.20 | 10376.95 | 10426.26 | 13.54 | 19.58 | 0.001 | 0.030 |
| 5 | 2654.42 | 2670.32 | 10846.04 | 10990.08 | 11.88 | 18.59 | 0.003 | 0.018 |
| 6 | 2012.53 | 1974.65 | 9737.35 | 9827.63 | 39.64 | 21.17 | 0.004 | 0.025 |
| 7 | 3056.36 | 2925.19 | 12519.74 | 13134.05 | 27.66 | 30.61 | 0.015 | 0.071 |
| 8 | 3133.76 | 2756.66 | 10504.00 | 10530.00 | 32.57 | 36.38 | 0.002 | 0.003 |
| 9 | 2195.08 | 2142.53 | 10499.81 | 10470.06 | 8.23 | 13.01 | 0.002 | 0.004 |
| 10 | 2454.57 | 2406.96 | 12936.62 | 12981.21 | 41.52 | 20.28 | 0.006 | 0.024 |
| p-value | >0.05 | | >0.05 | | >0.05 | | >0.05 | |

As such, the SpaMA method, according to embodiments disclosed herein, that may be based on time-varying spectral analysis of the PPG signal addresses Heart Rate monitoring in the real world with challenges ranging from a subject who makes sudden movements but is otherwise sedate, to intensive. This phenomenon mostly was observed while dealing with the second set of datasets from the IEEE competition, which involved Type (2) and Type (3) activities. These types of exercises involved more abrupt movements which consequently made it more difficult to track the HR-related frequencies in the spectrum. In the three datasets that have been analyzed, recordings #10 and 14 are examples of this phenomenon.

A strength of the PPG's LED is one of the most important factors determining the SpaMA method performance. Movement induces much less spectrum corruption (shift) in the PPG if the LED is sufficiently strong. A reduction in the strength of the PPG signal can also be caused by ambient light leaking into the gap between a PPG sensor and the skin surface (Zhang, Z., Photoplethysmography-Based Heart Rate Monitoring in Physical Activities via Joint Sparse Spectrum Reconstruction. Biomedical Engineering, IEEE Transactions on, 2015. PP(99): p. 1-1). This is because the power of the signal is dependent on the depth and reflection of the light from the pulse oximeter to the subject's skin. This gap between skin and the planar substrate where the LEDs and PD are mounted may be the result of movement during physical activities or the shape of tissue that the sensors touch. Among the three datasets, low performance for recordings #16 and 31 is the result of a weak PPG signal most likely due to a gap between the sensor and skin caused by motion artifacts.

By using the sample-by-sample windowing process, SpaMA, according to embodiments disclosed herein, can be utilized for both Heart Rate monitoring and HRV analysis in both frequency- and time-domains. From the results, disclosed above, it can be observed that embodiments disclosed here are able to replicate both the low frequency (0.04-0.15 Hz) and the high frequency (0.15-0.4) dynamics well, albeit better the former than the latter, when compared to a reference HRV. For time-domain HRV measures, the mean HR, SDNN, RMSSD, and pNN50 based on embodiments disclosed herein were all found to be not significantly different than the reference HRV. It has long been shown that during dynamic exercise, heart rate increases due to both a parasympathetic withdrawal and an augmented sympathetic activity (Iellamo, F., Neural mechanisms of cardiovascular regulation during exercise. Auton Neurosci, 2001. 90(1-2): p. 66-75; Bernardi, L. and M. F. Piepoli, [Autonomic nervous system adaptation during physical exercise]. Ital Heart J Suppl, 2001. 2(8): p. 831-9). The relative role of the two drives depends on the exercise intensity (Perini, R., et al., The influence of exercise intensity on the power spectrum of heart rate variability. Eur J Appl Physiol Occup Physiol, 1990. 61(1-2): p. 143-8; Sarmiento, S., et al., Heart rate variability during high-intensity exercise. Journal of Systems Science and Complexity, 2013. 26(1): p. 104-116; Roure, R., et al., Autonomic nervous system responses correlate with mental rehearsal in volleyball training. Eur J Appl Physiol Occup Physiol, 1998. 78(2): p. 99-108). Analysis of HRV permits insight into this control mechanism (Aubert, A. E., B. Seps, and F. Beckers, Heart rate variability in athletes. Sports Med, 2003. 33(12): p. 889-919). Also, being able to do HRV analysis from PPG even during movement and physical activities would be an advantage for detecting and diagnosing many cardiovascular diseases using only PPG recordings.

The SpaMA method, according to embodiments disclosed herein, can be potentially implemented in real time. The method written in Matlab®, version R2014 and CPU 3.4 GHz takes only 110 msec per 8 second segments. Therefore, given the high accuracy of the method in estimating HR despite severe motion artifacts, the SpaMA method, according to embodiments disclosed herein, has the potential to be applicable for implementation on wearable devices such as smart watches and PPG-based fitness sensors.

As disclosed above, accurate estimation of changing arterial oxygen saturation (SpO2) from photoplethysmogram (PPG) signals during movement is a very challenging problem. This is because strenuous and high intensity movements can result in severe motion artifacts (MA), making accurate SpO2 estimation from PPG signals difficult. As such, embodiment disclosed herein may applied the methods for reconstructing a PPG signal, as disclosed above, and include an additional stage of SpO2 estimation.

According to one embodiment, OxiMA may be comprised of the 6 stages disclosed above, with reference to FIGS. 3A-F, and include Stage 7, that is SpO2 Estimation.

According to another embodiment, OxiMA may be comprised of 6 stages: (1) Time-frequency Spectral Analysis, (2) Signal Decomposition, (3) Spectral Filtering, (4) Heart Rate (HR) extraction and tracking, (5) Signal Reconstruction, (6) SpO2 Estimation.

OxiMA

According to some embodiments, OxiMA may decompose the PPG signal into its frequency components by using a complex demodulation-based technique and may choose the components with frequencies close to the HR frequency for reconstructing the clean PPG signal. Next, SpO2 may be estimated from the reconstructed PPG signal. Such a method is applied to 22 minute datasets recorded from 10 subjects. A Nellcor OxiMax transmission sensor was used to collect analog PPG signals, while reference SpO2 and HR were collected simultaneously from the FDA approved Masimo SET Radical RDS-1 pulse oximeter. The performance of the OxiMA method according to embodiments disclosed herein, was determined by computing the mean absolute error between the estimated HR/SpO2 from the PPG and reference HR [Masimo]/SpO2[Masimo] oximeter. The results show the average estimation error using OxiMA are only 2.4 beats/minute for HR and 1.8% for SpO2, respectively. As such, the OxiMA method has great potential for MA reduction for both SpO2 and HR monitoring.

Vital signs and clinical symptoms have been shown to be poor predictors of hypoxia, and in order to rationalize oxygen therapy, measurement of arterial oxygen saturation by pulse oximetry is being increasingly recommended (Laman, M., et al., Can clinical signs predict hypoxaemia in Papua New Guinean children with moderate and severe pneumonia? Ann Trop Paediatr, 2005. 25(1): p. 23-7) Arterial oxygen saturation (SpO2) reflects the relative amount of oxyhemoglobin in the arterial blood. The most common method to measure SpO2 is based on pulse oximetry, whereby oxidized hemoglobin and reduced hemoglobin have significantly different optical spectra.

Specifically, at a red wavelength of about 660 nm, there is a significant difference in light absorbance between reduced (Hb) and oxidized hemoglobin (HbO2). A measurement of the percent oxygen saturation of blood is defined as the ratio of oxyhemoglobin to the total concentration of hemoglobin present in the blood. Pulse oximetry assumes that the fluctuations of the PPG signal are caused by changes in arterial blood volume associated with each heartbeat, where the magnitude of the fluctuations depends on the amount of arterial blood rushing into the peripheral vascular bed, the optical absorption of the blood, skin and tissue, and the wavelengths used to illuminate the blood. The photoplethysmogram (PPG) can be used to derive not only the SpO2 and heart rate (HR) data, but also other vital physiological information (Laman, M., et al., Can clinical signs predict hypoxaemia in Papua New Guinean children with moderate and severe pneumonia? Ann Trop Paediatr, 2005. 25(1): p. 23-7; Salehizadeh, S. M. A., et al., Photoplethysmograph Signal Reconstruction based on a Novel Motion Artifact Detection-Reduction Approach. Part Motion and Noise Artifact Removal. Annals of Biomedical Engineering, 2014. 42(11): p. 2251-2263; Tamisier, R., et al., A new model of chronic intermittent hypoxia in humans: effect on ventilation, sleep, and blood pressure. J Appl Physiol (1985), 2009. 107(1): p. 17-24; Jubran, A., Pulse oximetry. Crit Care, 1999. 3(2): p. R11-r17). As disclosed above, utilizing a pulse oximeter as a multi-purpose vital sign monitor has clinical appeal, since it is familiar to clinicians and comfortable for the patient (Salehizadeh, S. M. A., et al., Photoplethysmograph Signal Reconstruction based on a Novel Motion Artifact Detection-Reduction Approach. Part Motion and Noise Artifact Removal. Annals of Biomedical Engineering, 2014. 42(11): p. 2251-2263).

In healthy persons, SpO2 is typically near 98%. A lower reading indicates a level of hypoxia. SpO2 readings below 95% are usually a cause for concern, indicating the need for supplemental oxygen therapy. In certain individuals, such as those with chronic respiratory or cardiac diseases, SpO2 readings below 95% may be considered normal. However, in general, SpO2 readings between 90%-95% represent mild hypoxia, while 85%-90% indicates serious hypoxia, and readings below 85% are considered critical hypoxia (Tamisier, R., et al., A new model of chronic intermittent hypoxia in humans: effect on ventilation, sleep, and blood pressure. J Appl Physiol (1985), 2009. 107(1): p. 17-24).

As disclosed below, the OxiMA method according to embodiments disclosed herein, provides HR reconstruction with accurate SpO2 estimation even during movement. The most recent methods as noted above (e.g., TROIKA and JOSS) do not show their ability to obtain SpO2 estimates as they were mainly designed for HR calculations in the presence of intense motion artifacts.

The OxiMA method was evaluated on a lab controlled dataset that was recorded during voluntary induced hypoxia. In an IRB approved study which recruited 10 subjects, one set of data was collected from each subject for a duration of 22 min. Reference arterial SpO2 and HR were collected from the FDA approved Masimo SET Radical RDS-1 pulse oximeter (mounted on the left hand), while a Nelicor Oxi-Max sensor (mounted on the right hand) was used to collect analog PPG signals, simultaneously, as shown in Table 9 of FIG. 14C, disclosed below.

Figure 14C:
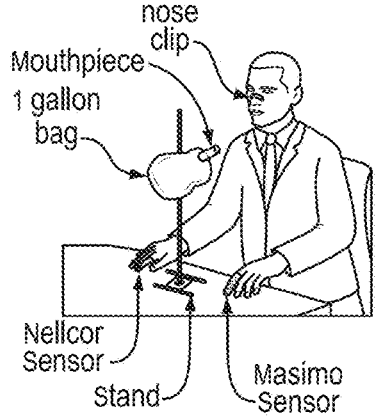
FIG. 14C is a table that includes PPG datasets and experiments settings.

FIG. 14C is a table, Table 9, that includes PPG datasets and experiments settings. Each subject sat in a chair and was asked to re-breathe into a 1-gallon bag four times for approximately two minutes each time. During the first and third time the subject rebreathed into the bag, subjects were asked to remain still. During the second and fourth time the subject rebreathed into the bag, subjects were asked to introduce motion artifacts into the measurement by shaking their right hand. Each subject wore a disposable nose clip to prevent accidental breathing of room air. The Masimo reference sensor placed in the left hand remained motionless for the entire duration of the study. Subjects had at least two minutes of rest between successive breathing maneuvers, with more time if requested. The protocol for this experiment is presented in Table 10. Worcester Polytechnic Institute IRB approved the study protocol and informed consent was required by all subjects prior to data recording.

This sequence of data recording allowed us to test the efficacy of the OxiMA method while a subject experienced different levels of short lasting hypoxia during motion artifacts. For reference, other clinical studies showed that SpO2 levels in patients suffering from mild to moderate sleep apnea can drop to about 80% for short periods of time until the patient is awakened without irreversible physiological effects (Maeda, Y., M. Sekine, and T. Tamura, Relationship between measurement site and motion artifacts in wearable reflected photoplethysmography. J Med Syst, 2011. 35(5): p. 969-76).

Methodology

The protocol for testing performance of the OxiMA method is presented in Table 10.

TABLE 10

EXPERIMENT PROTOCOL

| End Time (min) | Event |
| --- | --- |
| 2 | Rest (baseline) |
| 4 | Bag breathing (motion) |
| 5 | Rest (oxygen recovery) |
| 7 | Rest |
| 9 | Bag breathing (motion) |
| 10 | Rest (oxygen recovery) |
| 12 | Rest |
| 14 | Bag breathing (no motion) |
| 15 | Rest (oxygen recovery) |
| 17 | Rest |
| 19 | Bag breathing (motion) |
| 20 | Rest (oxygen recovery) |
| 22 | Rest |

Details of each stage of the OxiMA method as applied in the experiment are disclosed below.

Time-Varying Spectral Analysis of PPG and Accelerometer Data

To compute the time-frequency spectrum, a variable frequency complex demodulation technique was employed. Table 11, disclosed below, presents the OxiMA method, according to one embodiment.

The time-varying spectrum is estimated by taking a T-sec window of the PPG signal and computing the VFCDM time-frequency of the segment and then sliding the window through the whole dataset. There is no overlapping between the sliding time windows. The window segment length T was set to 8 seconds and was shifted by 8 seconds. The assumption of 8 second data length largely stems from the fact that SpO2 and heart rates do not change instantaneously; hence, an 8 second duration is a reasonable choice.

TABLE 11

OXIMA METHOD: HR AND SPO2 RECONSTRUCTION

Stage 1. VFCDM Time-Frequency Spectrum
1.1. Downsample the PPG signal to ¼ of the original sampling frequency.
1.2. Compute the VFCDM based time-frequency spectrum (TFS)
Stage 2. Signal Decomposition
2.1. Decompose the PPG signal into its frequency components according to frequency bands in the TFS
Stage 3. Spectral Filtering
3.1. Assume HR to be in the frequency range of [0.5 Hz-3 Hz], to account for both low and high HR values.
3.2. The first highest two peaks and their corresponding frequencies in the PPG filtered spectrum are assumed to have HR information.
Stage 4. Heart Rate Tracking and Extraction from PPG Spectrum
Case (1): From 3.1-if the spectrum is corrupted by movement and only the first largest peak is corrupted, then the HR frequency should be the frequency of the second peak in the spectrum.
Case (2): Due to the sensor-skin interface interruption, which could be a result of gap between the pulse oximeter and a subject's skin or slight sensor alignment variations relative to skin, the HR frequency cannot be extracted from the spectrum and in this case the previous HR frequency is used or for offline implementation a

TABLE 11-continued

OXIMA METHOD: HR AND SPO2 RECONSTRUCTION cubic spline interpolation can be applied to fill in the missing HR information.
Stage 5. PPG Signal Reconstruction
5.1. The PPG signal is reconstructed by using the summation of VFCDM components with frequency close to the HR frequency at each window.
Stage 6. Oxygen Saturation Estimation
6.1. Calculate the SpO2 estimations from reconstructed infrared and red PPG signals using the following empirical calibration equation [2]

Figure 15A:
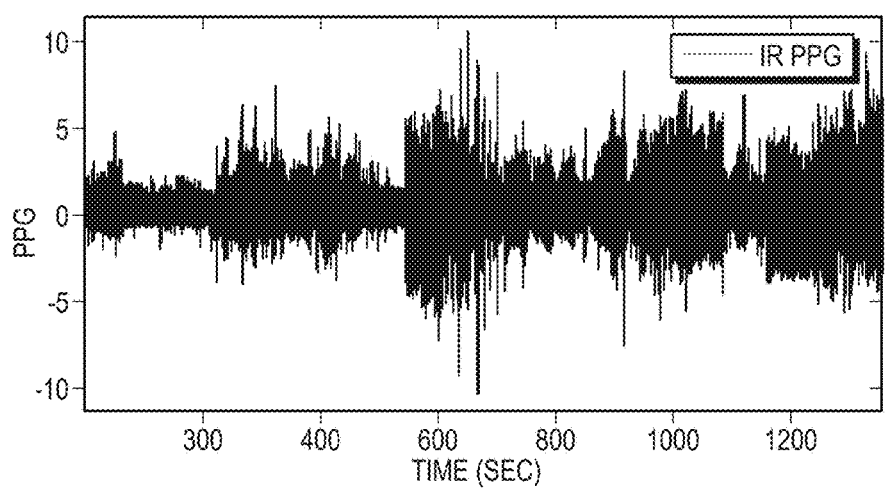
FIGS. 15A-B show an example resultant variable frequency complex demodulation (VFCDM) time-frequency spectrum of recordings from a given subject.
Figure 15B:
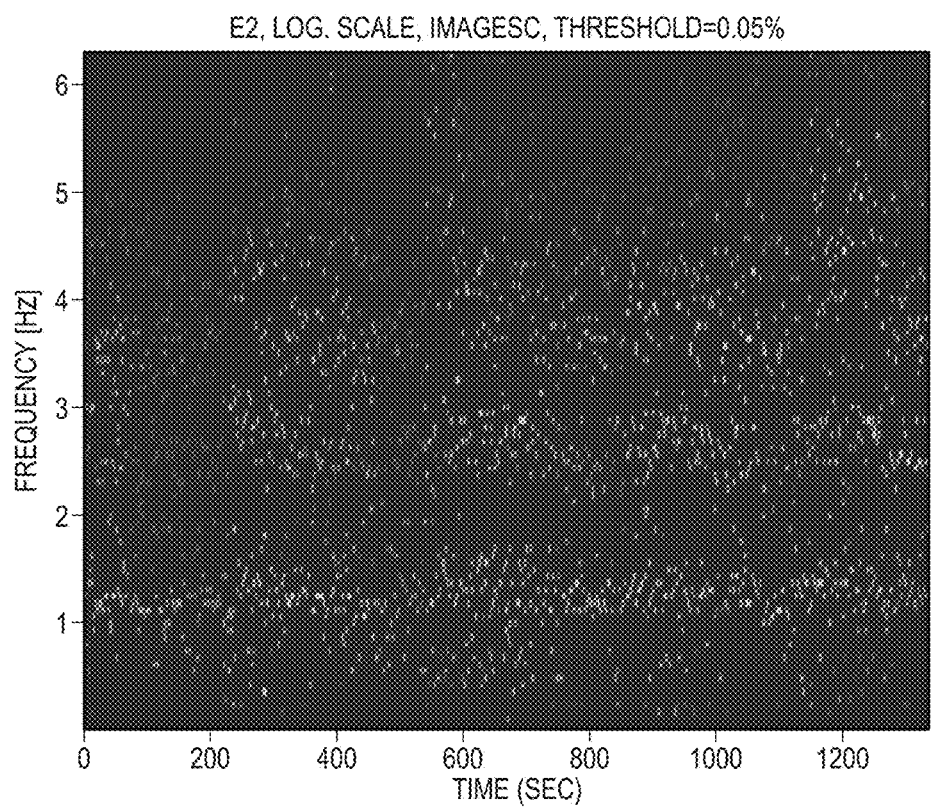

$SpO_2(\%) = (110 - 25R)$ where, $R = \dfrac{AC_{Red}/DC_{Red}}{AC_{IR}/DC_{IR}}$ FIGS. 15A-B show the resultant VFCDM time-frequency spectrum of recordings from subject #5, as a representative example.

The panels in FIGS. 15A-B show infrared PPG time series data. FIG. 15B represents the time-frequency plot of the infrared PPG signal. The next section details how the PPG data is decomposed into its frequency components using VFCDM.

Signal Decomposition

The original PPG signal was decomposed into sinusoidal modulations using a VFCDM method, as disclosed in Table 12 below.

$$x(t) = \sum_{i=1}^{N} \text{Component}\{i\} = \sum_{i=1}^{N} dc_i(t) A_i(t)\cos(2\pi f_i(t) + \phi_i(t)) \quad (4)$$

By assuming N=12 fixed frequency bands each with a distinct central frequency, the PPG and accelerometer signals may be decomposed using the VFCDM method of Table 12 which yields 12 components.

TABLE 12

VFCDM METHOD

Consider a sinusoidal signal x(t) to be a narrow band oscillation with a time-varying center frequency f(τ), instantaneous amplitude A(t), phase φ(t), and the direct current component dc(t):

$x(t) = dc(t) + A(t)\cos\left(\int_0^t 2\pi f(\tau) d\tau + \phi(t)\right)$

Step (1) For a given center frequency, we can extract the instantaneous amplitude information A(t) and phase information φ(t) by multiplying (1)

by $e^{-j\int_0^t 2\pi f(\tau)d\tau}$ which results in the following:

$z(t) = x(t)e^{-j\int_0^t 2\pi f(\tau)d\tau}$ $= dc(t)e^{-j\int_0^t 2\pi f(\tau)d\tau} + \dfrac{A(t)}{2}e^{j\phi(t)} + \dfrac{A(t)}{2}e^{-j(\int_0^t 4\pi f(\tau)d\tau + \phi(t))}$ Step (2) From (2), if z(t) is filtered with an ideal low-pass filter (LPF) with a cutoff frequency $f_c < f_0$, where $f_0$ is the center frequency of interest. Then the filtered signal $z_{lp}(t)$ will contain only the component of interest $z_{lp}(t) = \dfrac{A(t)}{2}e^{j\phi(t)}.$

TABLE 12-continued

VFCDM METHOD

Figure 16:
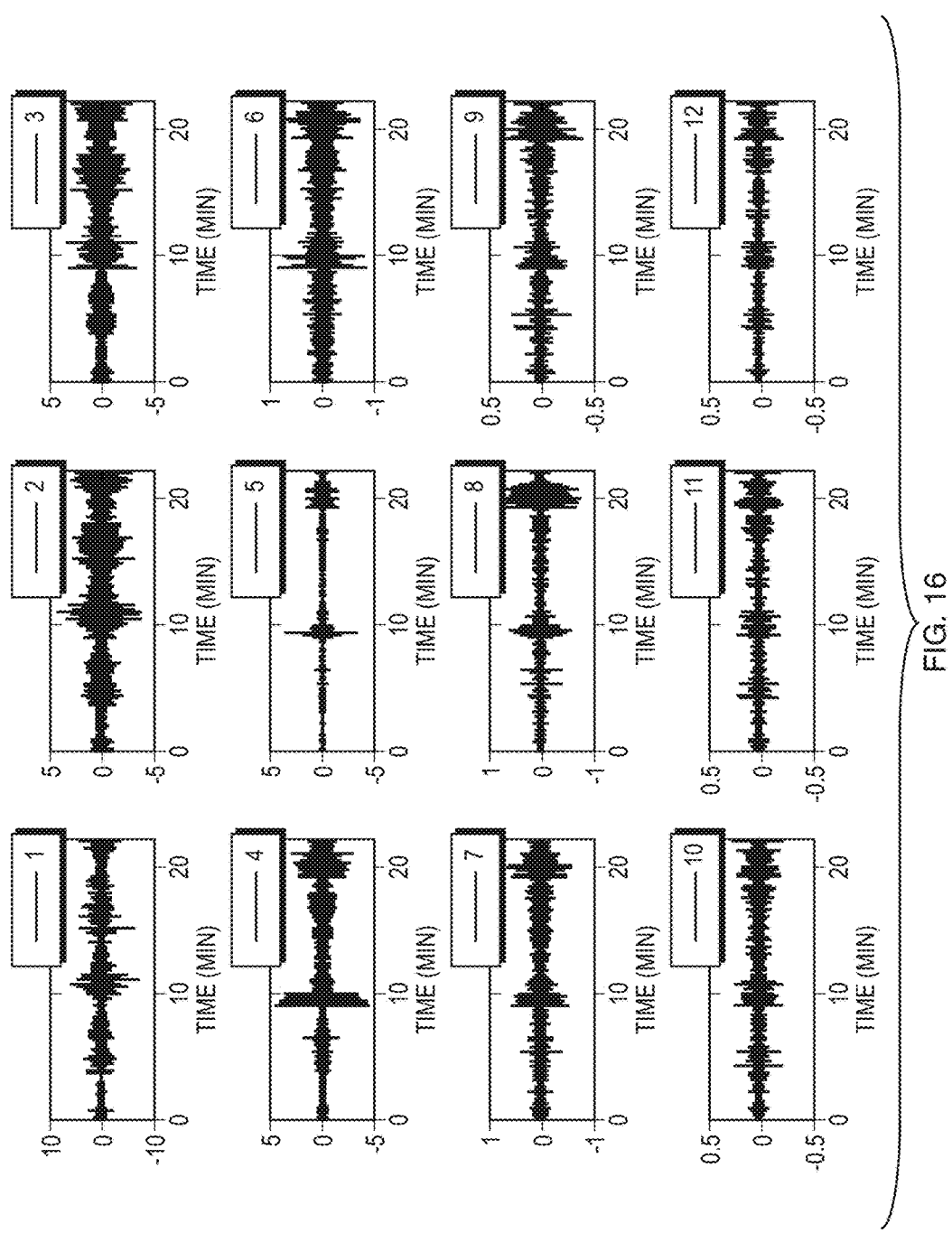
FIG. 16 shows twelve components corresponding to the Infrared (IR) and Red signal for the given subject.

Step (3) By changing the center frequency followed by using the variable frequency approach as well as the LPF, the signal, x(t), will be decomposed into the sinusoid modulations, $d_i$, by the CDM technique as follows:

$x(t) = \sum_i d_i = dc(t) + \sum_i A_i(t)\cos\left(\int_0^t 2\pi f_i(\tau) d\tau + \phi_i(t)\right)$ Step (4) The instantaneous frequency and amplitude of $d_i$ can be calculated using the Hilbert transform $A(t) = 2|z_{lp}(t)| = [X^2(t) + Y^2(t)]^{1/2}$ $X(t) = \text{real}(z_{lp}(t))$ $Y(t) = \text{imag}(z_{lp}(t))$ $= H[X(t)]$ $= \dfrac{1}{\pi}\int \dfrac{X(t')}{t-t'}dt'$ FIG. 16 shows the twelve components corresponding to the IR and Red signal for subject #5. Among the twelve frequency bands, bands 1 to 5 correspond to frequency range of [0.5 Hz to 3 Hz], which is typically the HR frequency range accounting for both normal and elevated heart rates. Embodiments disclosed herein select a component of these 5 components to reconstruct the signal that preserves the HR and is less corrupted by the motion artifacts. For the selection, an accurate HR may be estimated by selecting the components that match closest to the actual HR frequency in order to reconstruct a less noisy PPG signal than the original motion corrupted data.

Spectral Filtering

After obtaining the power spectral density at each window, HR frequency may be assumed to be confined in the range [0.5 Hz-3 Hz], which takes into account both at rest and high HR values due to either tachycardia or exercise scenarios. Next, for HR estimation, the strategy is to keep only frequencies that correspond to the first and second peak at each column of time-frequency matrix, as disclosed above, with reference to FIG. 3B.

In general, HR frequency in the VFCDM based power spectral density of the PPG at each window can have three different scenarios: (1) PPG is devoid of MA and there is no sensor-skin interface problems like a spatial gap between the sensor and the subject's skin during recording, (2) PPG is corrupted by MA and there is no spatial gap between the sensor and the subject's skin during recording and (3) There is a spatial gap between the sensor and the subject's skin during recording. For the ideal case (1), FIR can be extracted and it is most likely represented as the highest peak in the PPG spectrum. For case (2), MA dynamics can result in the dominant peak and HR frequency peak's magnitude become smaller than the MA frequency peak in the spectrum. The only scenario that makes it difficult to extract HR from the spectrum is scenario (3) when there is a spatial gap between the PPG sensor and the subject's skin during recording. In this scenario, assuming that the motion artifacts are short lasting, the missing HR values can be interpolated using the cubic spline approach.

Figure 17A:
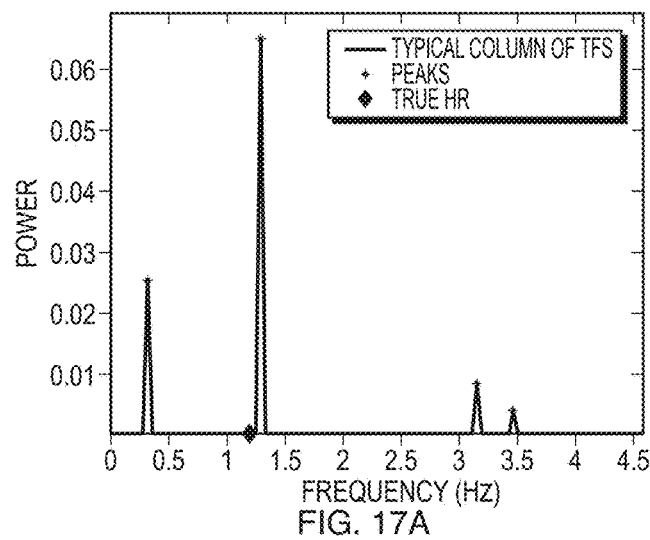
FIGS. 17A-C are example spectra plots corresponding to three scenarios.
Figure 17B:
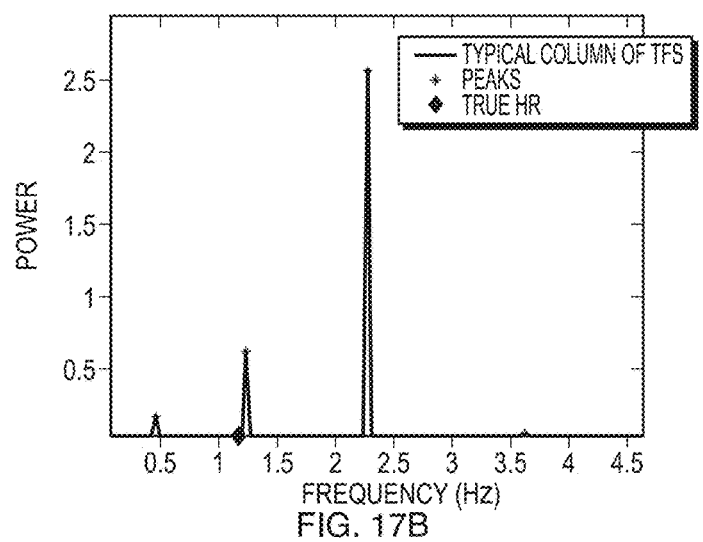
Figure 17C:
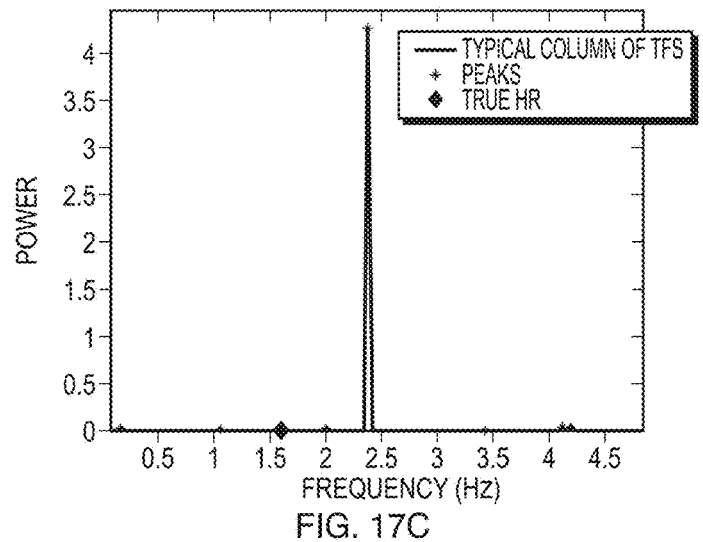

FIGS. 17A-C are plots of the above three scenarios. In FIG. 17A and FIG. 17B, the true HR frequency is close to the first and second peak respectively, while in FIG. 17C, the true HR frequency is far from the dominant peaks in the spectrum. As long as the PPG data is clean, an assumption may be made that the HR frequency belongs to the frequency component with the highest power (peak) at the each column of the TFS matrix. On the other hand, when the data becomes corrupted by MA, it might shift the HR frequency to the next highest peak in the spectrum or might lose the dominant HR frequency.

Embodiments disclosed herein employ a TFS filtering step to search for N first highest spectral peaks and their associated frequencies in each column of the TFS. Hence, the original TFS of FIG. 15B can be filtered to select only N, for example, 2, in the example embodiments, highest spectral peaks.

Figure 18A:
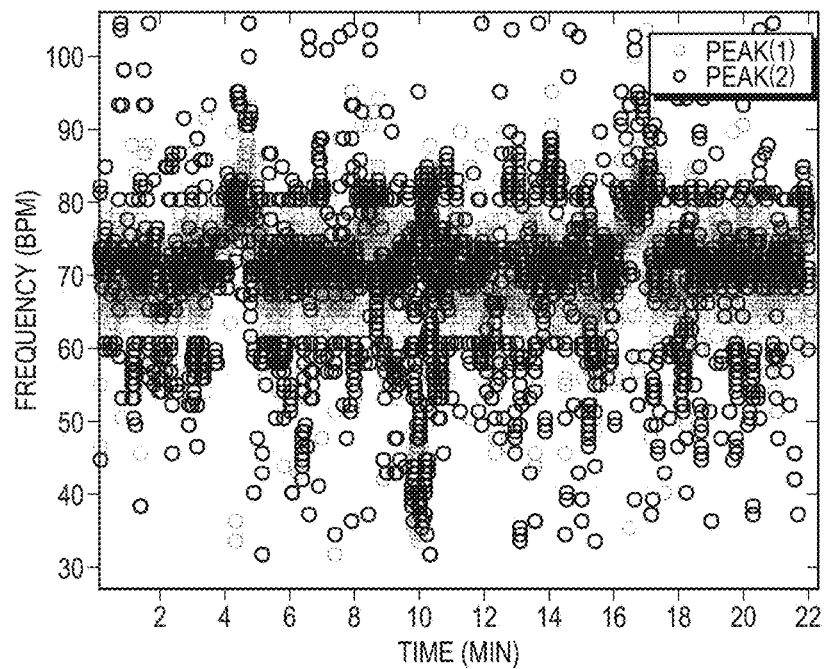
FIG. 18A shows a representative filtered time-frequency spectral plot of PPG recording from subject #5.

FIG. 18A shows a representative filtered time-frequency spectral plot of PPG recording from subject #5. This portion of the OxiMA method involves retaining only the two largest frequency peaks at each time point within the defined HR range (30-180 bpm) and they are represented as blue and green traces, respectively.

Heart Rate Tracking and Extraction

After filtering the TFS, the HR may be extracted. The HR tracking method may be summarized as: Assume there is only knowledge of the initial HR, the HR at each window is extracted by comparing the peaks to the previous HR value.

As disclosed above with reference to FIG. 3B, if the largest peak is within the 10 bpm range from the previous value of HR, it is chosen; if not, the second largest peak is checked for compliance of this scenario. If the HR value deviates by more than 10 bpm, the HR from the previous window may be adopted by the method.

Figure 18B:
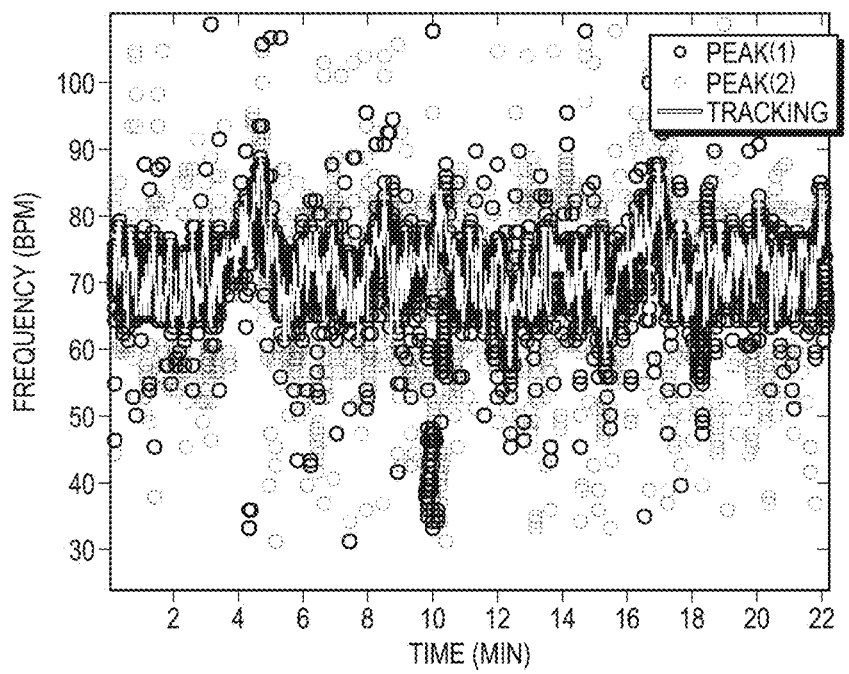
FIG. 18B shows tracking of HR based on embodiments disclosed herein.

FIG. 18B illustrates the tracking of HR based on OxiMA method, disclosed above.

Figure 19A:
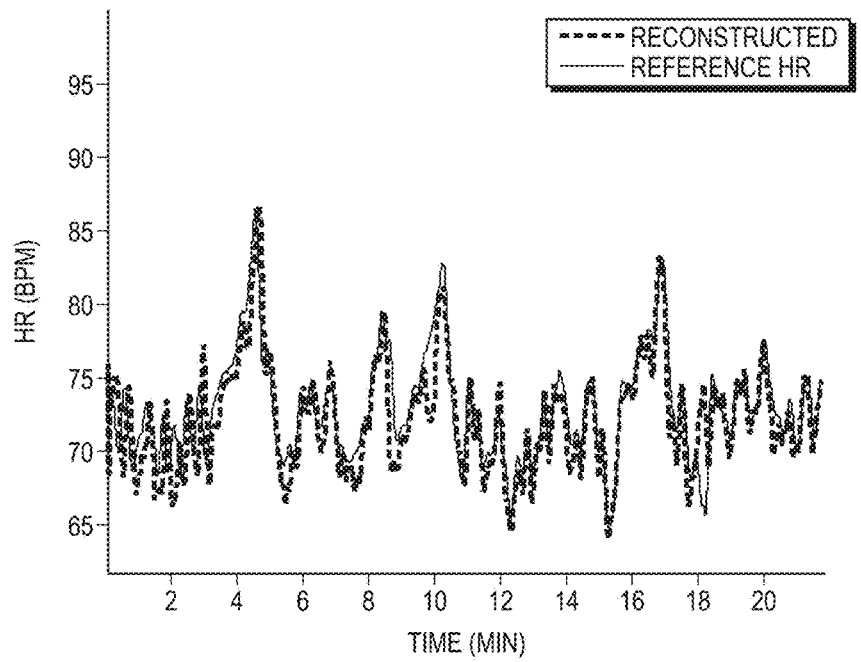
FIGS. 19A-B represent comparisons of an estimated 8 second moving average HR from a spectral approach for filtering motion artifacts for oxygen saturation estimation (OxiMA) method to a reference FIR, and an HR calculated from a motion-corrupted PPG signal compared to a reference HR from an ECG, respectively.
Figure 19B:
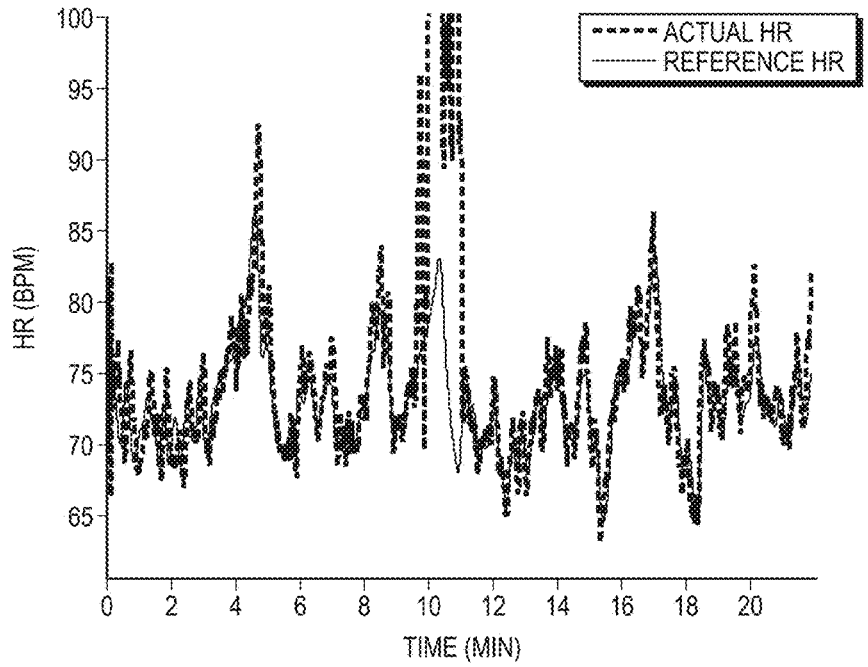

FIGS. 19A and 19B represent comparisons, of the estimated 8 second moving averaged HR from the OxiMA method, to the reference HR, and the HR calculated from the motion-corrupted PPG signal, compared to the reference HR from the ECG, respectively. In order to calculate the performance of the OxiMA method for HR reconstruction, the error value in each time window was calculated from the estimated HR to the reference ECG-derived HR. Two measurement indices of absolute and normalized errors similar to the indices in (Wang, H., et al., A high resolution approach to estimating time-frequency spectra and their amplitudes. Ann Biomed Eng, 2006. 34(2): p. 326-3) were used.

$$\text{Error}(1) = \frac{1}{W}\sum_{k=1}^{w} |HR_{OxiMA}(k) - HR_{ref}(k)| \tag{5}$$

$$\text{Error}(2) = \frac{1}{W}\sum_{k=1}^{w} \frac{|HR_{OxiMA}(k) - HR_{ref}(k)|}{HR_{OxiMA}(k)} \times 100\% \tag{6}$$

where, W is the total number of windows.

PPG Signal Reconstruction

Now that HR values at each time window are estimated from the time-frequency spectrum, the signal reconstruction phase of the OxiMA method may be performed. An assumption may be made that the signal components corresponding to the HR frequency are more robust against motion and, thus, a less corrupted signal can be reconstructed using the summation of these components.

Figure 20A:
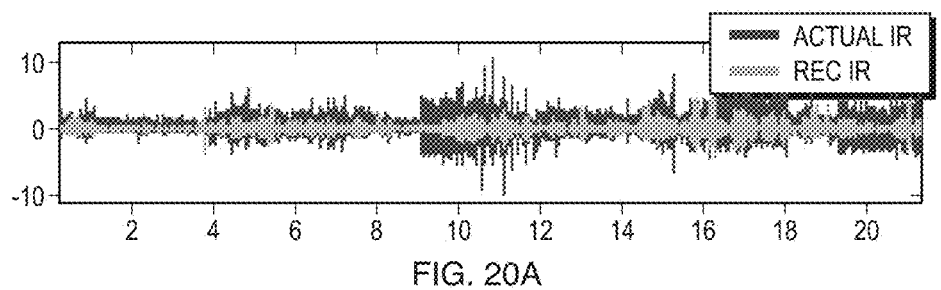
FIGS. 20A-C are example plots of data showing less motion-corrupted data that can be used for oxygen saturation estimation.
Figure 20B:
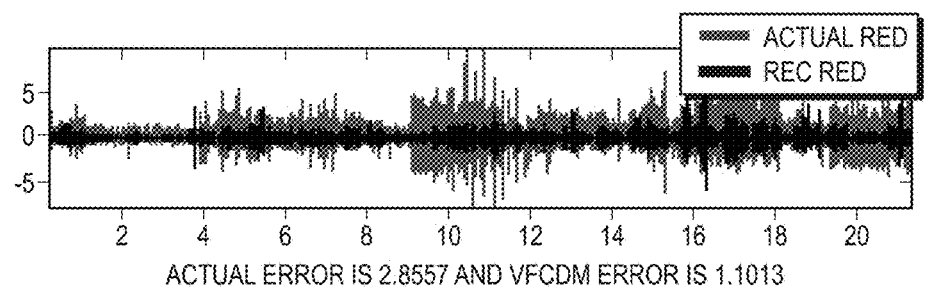

By calculating the components from the Signal Decomposition, using Eq (4) and the time-frequency spectrum of the PPG, at each 8-sec window a signal component may be chosen that has a frequency close to estimated HR frequency and that component may be employed to reconstruct infrared and red PPG data at each window. This yields a less motion-corrupted data that can be used for oxygen saturation estimation, as disclosed in FIG. 20A and FIG. 20B.

Oxygen Saturation Estimation

In order to calculate SpO2 from PPG signals, red and infrared PPG signals with clearly separable DC and AC components are required. Let the pulsatile components of the red and infrared PPG signals be denoted as $AC_{Red}$ and $AC_{IR}$, respectively, then the "ratio-of-ratio" R is estimated (Thakor, N. V. and Y. S. Zhu, Applications of adaptive filtering to ECG analysis: noise cancellation and arrhythmia detection. IEEE Trans Biomed Eng, 1991. 38(8): p. 785-94; Diniz, P., Adaptive filtering: algorithms and practical implementation. 2008: Springer Science, Business Media L.L.C) as $$R = \frac{AC_{Red}/DC_{Red}}{AC_{IR}/DC_{IR}} \tag{7}$$

Accordingly, SpO2 may be computed by substituting the R value in an empirical linear approximated relation given by $SpO_2(\%)=(110-25R)$.

Figure 20C:
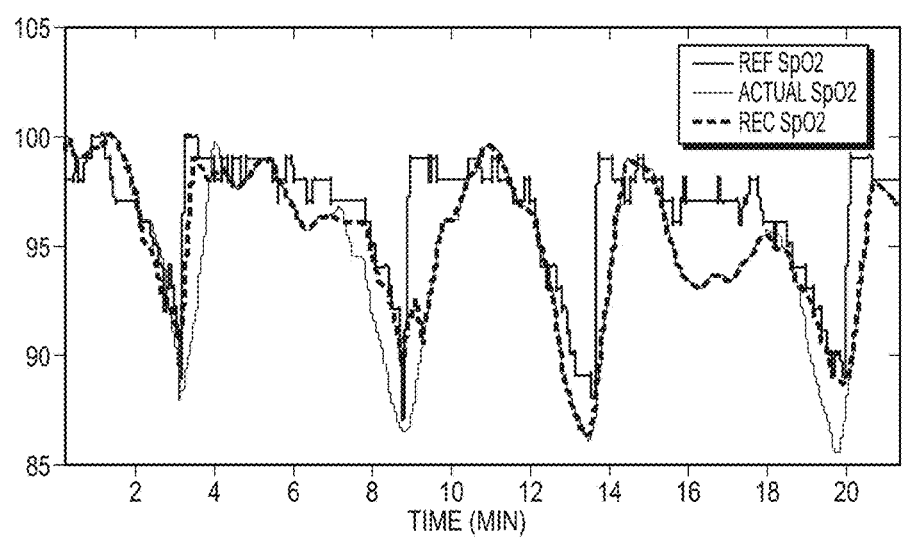
Figure 21A:
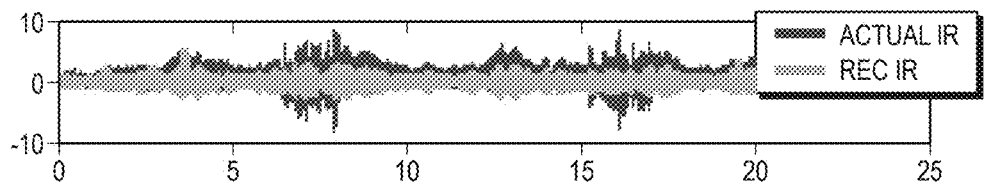
FIGS. 21A-C and FIGS. 22A-B show reconstructed arterial oxygen saturation (SpO2) and FIR in comparison to the reference HR from ECG recordings for the given subject.
Figure 21B:
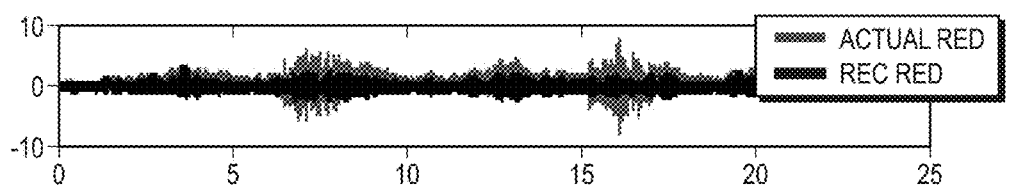
Figure 21C:
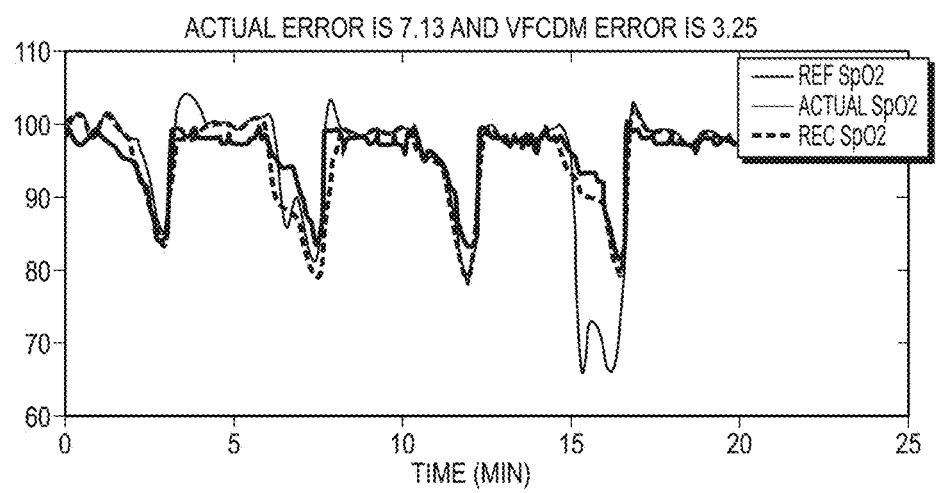
Figure 22A:
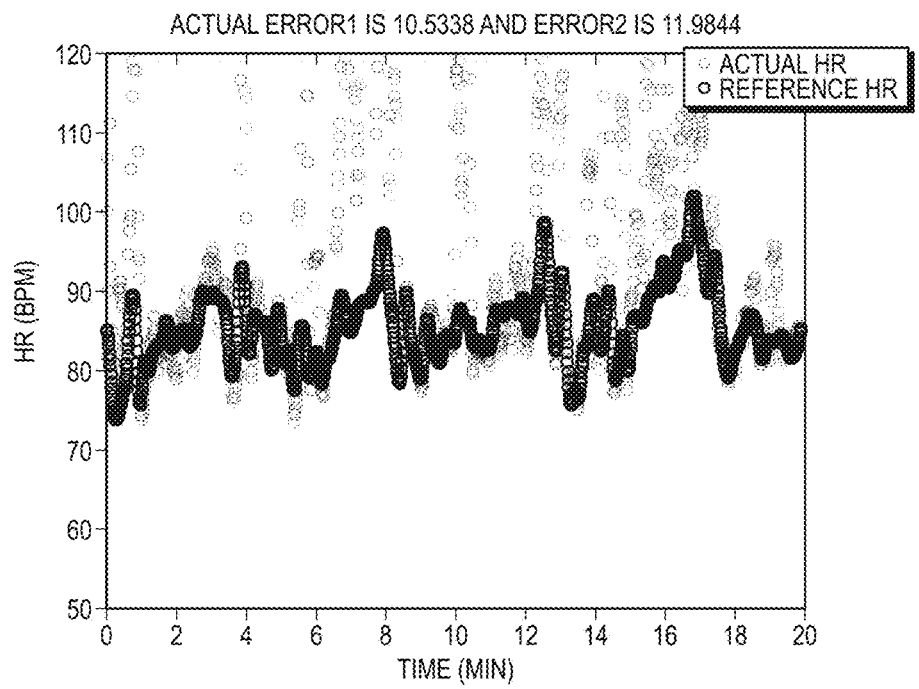
Figure 22B:
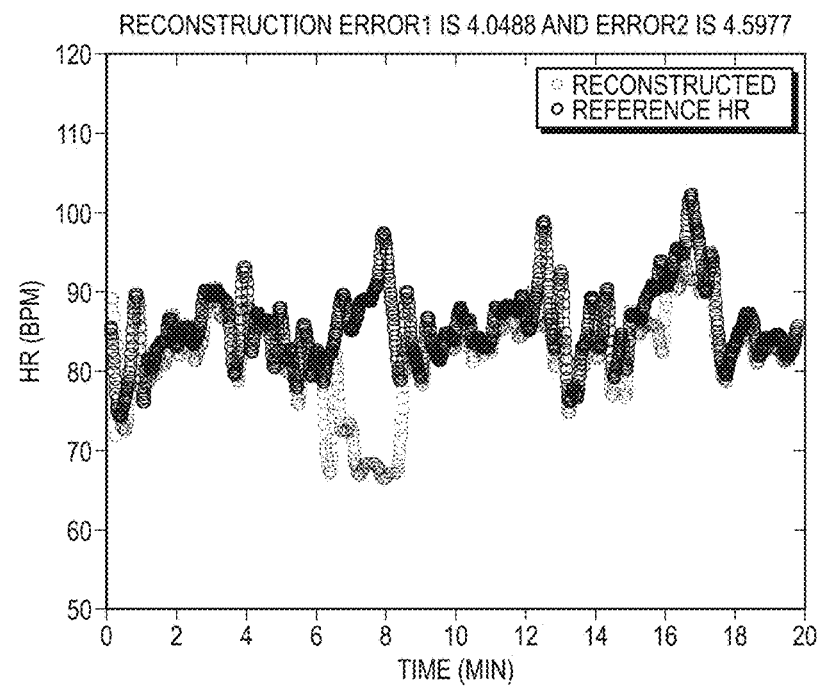

FIG. 20C represents the reconstructed SpO2 values obtained from OxiMA in comparison to the reference SpO2 values and the estimated values before reconstruction.

OxiMA Results

Table 13 represents the average absolute error (E1) and the average absolute error percentage (E2) of HR and SpO2 estimations of the OxiMA method on the varying hypoxia level dataset.

TABLE 13

OXIMA METHOD PERFORMANCE COMPARISON (HR ESTIMATIONS)

| | Actual HR estimation error | | OxiMA HR estimation error | |
|---|---|---|---|---|
| Subject | E1 | E2% | E1 | E2% |
| 1 | 3.84 | 4.83 | 1.53 | 2.10 |
| 2 | 6.84 | 9.57 | 2.72 | 3.97 |
| 3 | 8.15 | 9.59 | 1.69 | 2.29 |
| 4 | 4.55 | 5.39 | 2.61 | 3.18 |
| 5 | 10.53 | 11.96 | 4.04 | 4.60 |
| 6 | 4.46 | 5.52 | 2.04 | 2.66 |
| 7 | 12.41 | 19.65 | 2.81 | 4.37 |
| 8 | 3.84 | 4.35 | 2.10 | 2.46 |
| 9 | 3.80 | 4.13 | 2.57 | 2.83 |
| 10 | 3.65 | 4.20 | 1.85 | 2.41 |
| mean ± std | 6.20 ± 3.2 | 7.91 ± 5.0 | 2.40 ± 0.73 | 3.09 ± 0.90 |

The OxiMA method is compared to the HR and SpO2 estimations prior to the reconstruction method, where both pre- and post-reconstruction estimations are compared to the reference FIR and reference SpO2 values obtained from the Masimo pulse oximeter.

The results presented in Table 13 show that OxiMA on average improves the HR and SpO2 estimations by 100% and 105%, respectively when compared to those estimations without the reconstruction method. Improvement rates are calculated as follow:

$$ImRate1(\%) = \frac{1}{W}\sum_{k=1}^{w} \frac{|\text{Error}1_{OxiMA}(k) - \text{Error}1_{Act}(k)|}{\text{Error}1_{OxiMA}(k)} \times 100\% \tag{8}$$

-continued $$ImRate2(\%) = \frac{1}{W}\sum_{k=1}^{w}\frac{|Error2_{OxiMA}(k) - Error2_{Act}(k)|}{Error2_{OxiMA}(k)} \times 100\% \qquad (9)$$

FIGS. 21A-C and FIGS. 22A-B show the reconstructed SpO2 and HR in comparison to the reference HR from ECG recordings for subject #5. The largest error among all recordings was found to be from this recording, as shown in Tables 13 and 14. The larger error could be due to rapid movements or skin-sensor gap during the recordings.

TABLE 14

OXIMA METHOD PERFORMANCE COMPARISON (SPO$_2$ ESTIMATIONS)

| Subject | Actual SpO$_2$ estimation error | | OxiMA SpO$_2$ estimation error | |
|---|---|---|---|---|
| | E1 | E2% | E1 | E2% |
| 1 | 2.51 | 2.63 | 0.86 | 0.90 |
| 2 | 7.14 | 9.63 | 2.45 | 3.10 |
| 3 | 6.21 | 6.59 | 1.61 | 1.67 |
| 4 | 1.89 | 2.46 | 0.95 | 1.16 |
| 5 | 7.13 | 7.80 | 3.25 | 3.47 |
| 6 | 2.85 | 2.99 | 1.10 | 1.14 |
| 7 | 5.83 | 9.09 | 2.57 | 4.52 |
| 8 | 3.51 | 4.63 | 1.73 | 2.22 |
| 9 | 1.81 | 2.10 | 1.50 | 1.61 |
| 10 | 4.85 | 5.91 | 1.93 | 2.07 |
| mean ± std | 4.37 ± 2.1 | 5.38 ± 2.8 | 1.79 ± 0.8 | 2.19 ± 1.2 |

As such, the E1 (HR) for this particular subject is as low as 4.05 bpm while the E1 (SpO2) is as low as 3.25%. It can be seen from Table 15, disclosed below, that HR and SpO2 both improved by 160% and 119%, respectively, post reconstruction method.

TABLE 15

OXIMA METHOD PERFORMANCE COMPARISON (SPO$_2$ ESTIMATIONS)

| Subject | HR Improvement Rate | | SpO$_2$ Improvement Rate | |
|---|---|---|---|---|
| | ImRate1% | ImRate2% | ImRate1% | ImRate2% |
| 1 | 150.90 | 130.00 | 191.86 | 192.22 |
| 2 | 151.47 | 141.05 | 191.43 | 210.64 |
| 3 | 323.08 | 318.78 | 285.71 | 294.61 |
| 4 | 74.33 | 69.50 | 98.95 | 112.07 |
| 5 | 160.17 | 160.66 | 119.38 | 124.78 |
| 6 | 118.63 | 107.52 | 159.09 | 162.28 |
| 7 | 377.22 | 372.54 | 126.85 | 101.10 |
| 8 | 82.86 | 76.83 | 102.89 | 108.55 |
| 9 | 47.86 | 45.94 | 20.67 | 30.43 |
| 10 | 97.30 | 74.27 | 151.30 | 185.5 |
| mean ± | 158.38± | 149.71± | 144.81± | 152.2± |

V. Conclusions

As such, the OxiMA method that may be based on time-varying spectral analysis of the PPG signal combats motion artifacts that can degrade the accuracy of SpO2 and HR estimations. According to embodiments disclosed herein, the OxiMA method may decompose the PPG signal into many frequency bands using a VFCDM method (Chon, K. H., S. Dash, and J. Kihwan, Estimation of Respiratory Rate From Photoplethysmogram Data Using Time-Frequency Spectral Estimation. Biomedical Engineering, IEEE Transactions on, 2009. 56(8): p. 2054-2063), or any other suitable time-frequency technique, such as a wavelet analysis (Chon, K. H., S. Dash, and J. Kihwan, Estimation of Respiratory Rate From Photoplethysmogram Data Using Time-Frequency Spectral Estimation. Biomedical Engineering, IEEE Transactions on, 2009. 56(8): p. 2054-2063). According to embodiments disclosed herein, those components that are within the heart rate ranges including both extreme ranges of the low and high heart rates may be decomposed and used to reconstruct the PPG signal based on those components. As such, frequencies that are not within the prescribed HR ranges may be removed. From this reconstructed time series FIR may be estimated and SpO2 may be estimated, as disclosed above.

The dataset used to verify the OxiMA method's performance was collected from 10 subjects during hypoxic experiments. The results show accurate estimation of both FIR and SpO2 even during the presence of severe motion artifacts where the average error was only 2.4 bpm. More importantly, the average improvements in these estimates are astoundingly high for both HR (149%) and SpO2 (152%) when the reconstruction method applied, according to embodiments disclosed herein. Other methods for estimates of HR during severe motion artifacts for PPG signal Zhilin, Z., P. Zhouyue, and L. Benyuan, TROIKA: A General Framework for Heart Rate Monitoring Using Wrist-Type Photoplethysmographic Signals During Intensive Physical Exercise. Biomedical Engineering, IEEE Transactions on, 2015. 62(2): p. 522-531; Zhang, Z., Photoplethysmography-Based Heart Rate Monitoring in Physical Activities via Joint Sparse Spectrum Reconstruction. Biomedical Engineering, IEEE Transactions on, 2015. PP(99): p. 1-1; Salehizadeh, S., et al., A Novel Time-Varying Spectral Filtering Algorithm for Reconstruction of Motion Artifact Corrupted Heart Rate Signals During Intense Physical Activities Using a Wearable Photoplethysmogram Sensor. Sensors, 2015. 16(1): p. 10) produced good results (Kalman, R. E., A New Approach to Linear Filtering and Prediction Problems Transactions of the ASME—Journal of Basic Engineering, 1960. Series D (82)). However, these methods are only confined to HR estimation and not SpO2. Specifically, previous PPG reconstruction methods, such as (Salehizadeh, S. M. A., et al., Photoplethysmograph Signal Reconstruction based on a Novel Motion Artifact Detection-Reduction Approach. Part II: Motion and Noise Artifact Removal. Annals of Biomedical Engineering, 2014. 42(11): p. 2251-2263; Kim, B. S. and S. K. Yoo, Motion artifact reduction in photoplethysmography using independent component analysis. IEEE Trans Biomed Eng, 2006. 53(3): p. 566-8), have been tested under MA conditions but not with concomitant hypoxia. The results, disclosed abele, illustrate the efficacy of a method which provides accurate estimates of both SpO2 and HR even when there are significant MA and concomitant low oxygen saturation values.

Observations were made while analyzing the OxiMA data. The tracking ability of the OxiMA method decreased as the frequency changes during recordings increased. This is mostly likely because OxiMA tracks a dominant frequency through an 8-second window. Since each subjects' motion varied throughout each hypoxic maneuver, the dominant frequency can change within the observed window. The strength of the PPG's LED is one of the most important factors determining the performance. A reduction in the strength of the PPG signal can be caused by ambient light leaking into the gap between a PPG sensor and the skin surface (Zhang, Z., Photoplethysmography-Based Heart Rate Monitoring in Physical Activities via Joint Sparse Spectrum Reconstruction. Biomedical Engineering, IEEE Transactions on, 2015. PP(99): p. 1-1). This is because the power of the signal is dependent on the depth and reflection of the light from the pulse oximeter sensor to the subject's skin. This gap between the skin and the sensor may be the result of movement during physical activities or the shape of tissue that the sensors touch. In the datasets that have been analyzed, recordings #5 and #7 are examples of the above two scenarios.

Additionally, the local blood perfusion of the monitored region affects the signal-to-noise ratio of the PPG signal. When performing the hypoxic maneuvers, subjects' HR and breathing rate normally increase as oxygen saturation decreases. These physiologic changes cause more distinct pulsations in the digits, which increase the signal-to-noise ratio.

The OxiMA method can be easily implemented in real-time. Execution time of the method has been found to be only 180 msec on data divided into 8 second segments using Matlab® R2014a and CPU 3.6 GHz. Therefore, given the high accuracy of the OxiMA method in estimating FIR and SpO2 despite severe motion artifacts, this method has the potential to be applicable for implementation on wearable devices such as smart watches and PPG-based fitness sensors.

FIG. 23 is a block diagram of an example of the internal structure of a computer 2300 in which various embodiments of the present disclosure may be implemented. The computer 2300 contains a system bus 2302, where a bus is a set of hardware lines used for data transfer among the components of a computer or processing system. The system bus 2302 is essentially a shared conduit that connects different elements of a computer system (e.g., processor, disk storage, memory, input/output ports, network ports, etc.) that enables the transfer of information between the elements. Coupled to the system bus 2302 is an I/O device interface 2404 for connecting various input and output devices (e.g., keyboard, mouse, displays, printers, speakers, etc.) to the computer 2300. A network interface 2306 allows the computer 2300 to connect to various other devices attached to a network. Memory 2308 provides volatile storage for computer software instructions 2310 and data 2312 that may be used to implement embodiments of the present disclosure. Disk storage 2314 provides non-volatile storage for computer software instructions 2310 and data 2312 that may be used to implement embodiments of the present disclosure. A central processor unit 2318 is also coupled to the system bus 2302 and provides for the execution of computer instructions.

Further example embodiments disclosed herein may be configured using a computer program product; for example, controls may be programmed in software for implementing example embodiments. Further example embodiments may include a non-transitory computer-readable medium containing instructions that may be executed by a processor, and, when loaded and executed, cause the processor to complete methods described herein. It should be understood that elements of the block and flow diagrams, such as the reconstruction unit 416, output unit 418, reconstruction unit 516, output unit 518, heart rate unit, arterial oxygen saturation (SpO2) unit, and ailment unit, disclosed above, may be implemented in software, hardware, such as via one or more arrangements of circuitry of FIG. 23, disclosed above, or equivalents thereof, firmware, a combination thereof, or other similar implementation determined in the future. In addition, the elements of the block and flow diagrams described herein may be combined or divided in any manner in software, hardware, or firmware. If implemented in software, the software may be written in any language that can support the example embodiments disclosed herein. The software may be stored in any form of computer readable medium, such as random access memory (RAM), read only memory (ROM), compact disk read-only memory (CD-ROM), and so forth. In operation, a general purpose or application-specific processor or processing core loads and executes software in a manner well understood in the art. It should be understood further that the block and flow diagrams may include more or fewer elements, be arranged or oriented differently, or be represented differently. It should be understood that implementation may dictate the block, flow, and/or network diagrams and the number of block and flow diagrams illustrating the execution of embodiments disclosed herein.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method for reconstructing a heart-related signal output by a biomedical sensor, the method comprising:
reconstructing a representation of the heart-related signal to produce a reconstructed representation of the heart-related signal, the reconstructing based on (i) a time-varying spectral analysis of the heart-related signal and a motion signal, the motion signal output by a motion sensor and representative of motion artifacts in the heart-related signal, the motion artifacts being signal artifacts produced by movement of the biomedical sensor relative to a sensing location, and (ii) a classification of the movement, wherein the time-varying spectral analysis includes pre-processing the heart-related signal to produce a pre-processed heart-related signal, pre-processing the motion signal to produce a pre-processed motion signal, and computing a first time-frequency spectrum (TFS) of the heart-related signal using the pre-processed heart-related signal and a second TFS of the motion signal using the pre-processed motion signal; and
outputting the reconstructed representation of the heart-related signal.

2. The method of claim 1, wherein the motion artifacts are suppressed in the reconstructed representation of the heart-related signal.

3. The method of claim 1, wherein:
in an event the classification indicates that the movement does not rise to a level causing the motion artifacts, the reconstructed representation is based on an average value of peak-to-peak intervals in the pre-processed heart-related signal.

4. The method of claim 1, wherein the pre-processing includes filtering the heart-related signal to produce a filtered heart-related signal, the filtered heart-related signal being the pre-processed heart-related signal.

5. The method of claim 4, wherein the pre-processing further includes down-sampling the filtered heart-related signal, the down-sampling being at a sampling rate less than an original sampling rate.

6. The method of claim 1, wherein the first TFS computed and the second TFS computed are 3-dimensional spectra, the first TFS computed and the second TFS computed each including a respective time-varying amplitude or power distribution with respect to time and frequency.

7. The method of claim 1, wherein the first TFS computed is a first time-varying power spectral density (PSD) and the second TFS computed is a second time-varying PSD.

8. The method of claim 1, wherein the reconstructed representation is a current reconstructed representation and wherein, based on the classification indicating that the movement does rise to a level causing the motion artifacts and is a pseudo-periodic movement or a periodic movement, the reconstructing includes:
determining whether at least one spectral peak is present having a corresponding frequency within a given frequency range at a point in time in the first TFS computed, the current reconstructed representation being reconstructed for the point in time; and
wherein, based on a determination that the at least one spectral peak is not present, the current reconstructed representation is based on a prior reconstructed representation, the prior reconstructed representation associated with a previous point in time in the first TFS computed.

9. The method of claim 8, wherein the given frequency range is 0.5 Hz to 3 Hz.

10. The method of claim 1, wherein the reconstructing includes:
retaining up to a pre-determined number of candidate spectral peaks located at a first point in time in the first TFS computed, the candidate spectral peaks retained based on having corresponding frequencies within a given frequency range and highest amplitude or power values relative to other spectral peaks located at the first point in time, the other spectral peaks having respective frequencies within the given frequency range; and
discarding each of the candidate spectral peaks retained that is associated with a same frequency as a dominant spectral peak located at a second point in time in the second TFS computed, the first point in time and the second point in time having same time values.

11. The method of claim 10, wherein the given frequency range is 0.5 Hz to 3 Hz.

12. The method of claim 10, wherein the representation is a current representation, the reconstructed representation is a current reconstructed representation, and wherein, in an event the discarding discards each of the candidate spectral peaks retained, reconstructing the current representation is based on a prior reconstructed representation, the prior reconstructed representation associated with a previous point in time in the first TFS computed, the previous point in time being an earlier point in time with respect to the first point in time.

13. The method of claim 10, wherein the discarding is a first discarding and wherein the representation is a current representation and, wherein, in an event the first discarding results in at least one remaining candidate spectral peak retained, reconstructing the current representation further includes:
second discarding, wherein the second discarding discards remaining candidate spectral peaks, of the at least one remaining candidate spectral peak retained, based on whether a corresponding frequency of the at least one remaining candidate spectral peak retained is distanced by at least a frequency difference threshold from a prior reconstructed representation's frequency, the prior reconstructed representation associated with a previous point in time in the first TFS computed, the previous point in time being an earlier point in time with respect to the first point in time.

14. The method of claim 13, wherein:
based on each of the at least one remaining candidate spectral peak retained having been discarded by the second discarding, reconstructing the current representation is based on the prior reconstructed representation; and
based on at least one last candidate spectral peak remaining, the at least one last candidate spectral peak remaining not discarded by the second discarding, reconstructing the current representation is based on a selected candidate spectral peak selected from amongst the at least one last candidate spectral peak remaining having a closest corresponding frequency to the prior reconstructed representation's frequency relative to respective frequencies of each of the at least one last candidate spectral peak remaining.

15. The method of claim 10, wherein the dominant spectral peak has a largest power or amplitude value relative to other peaks located at the second point in time in the second TFS.

16. The method of claim 10, wherein the retaining and the discarding are based on:
the classification indicating that the movement is a pseudo-periodic movement or a periodic movement; and
determining that at least one spectral peak with a corresponding frequency in the given frequency range is present at the first point in time.

17. The method of claim 1, wherein the pre-processing includes filtering the heart-related signal and the motion signal to produce a filtered heart-related signal and a filtered motion signal, respectively, the filtered heart-related signal being the pre-processed heart-related signal and the filtered motion signal being the pre-processed motion signal.

18. The method of claim 17, wherein the pre-processing further includes down-sampling both the filtered heart-related signal and the filtered motion signal, the down-sampling being at a sampling rate less than an original sampling rate.

19. The method of claim 1, further including:
classifying the classification of the movement by comparing an amount of amplitude modulation in the second TFS computed to an amplitude modulation threshold, wherein the classification indicates whether the movement rises to a level of causing the motion artifacts based on a result of the comparing.

20. The method of claim 19, wherein the amplitude modulation threshold is dependent on a type of the motion detector sensor.

21. The method of claim 19, wherein, in an event the result indicates that the movement does rise to the level causing the motion artifacts, classifying the classification of the movement further includes determining whether the movement is either a pseudo-periodic movement or a periodic movement, versus a random movement.

22. The method of claim 21, wherein, in determining whether the movement is either the pseudo-periodic movement or the periodic movement, versus the random movement includes, the method further includes:
identifying a first, second, and third frequency associated, respectively, with a first, second, and third spectral peak in the second TFS at a point in time in the second TFS, the first, second, and third peaks having largest power or amplitude values relative to other peaks in the second TFS at the point in time, the first spectral peak being a largest spectral peak amongst the first, second, and third spectral peaks;

computing a first ratio of the second frequency identified to the first frequency identified and determining a first comparison result by comparing the first ratio computed to a first ratio value; and computing a second ratio of the third frequency identified to the first frequency identified and determining a second comparison result by comparing the second ratio computed to a second ratio value, wherein the classification further indicates that the movement is either the pseudo-periodic movement or the periodic movement, versus the random movement, based on the first comparison result and the second comparison result.

23. The method of claim 22, wherein the first ratio value is 2 and the second ratio value is 3.

24. The method of claim 1, wherein, in an event the classification of the movement indicates random movement, the reconstructing includes:

computing an average value of a number of prior reconstructed representations outputted prior to the reconstructing, the number based on a duration of consecutive motion artifacts, detected prior to the reconstructing;

computing a bandpass filter cutoff frequency based on the average value computed;

filtering the pre-processed heart-related signal by applying the band pass filter computed to produce a filtered, pre-processed heart-related signal; and wherein the reconstructed representation is based on an average peak-to-peak interval value of the filtered, pre-processed heart-related signal.

25. The method of claim 1, wherein the heart-related signal and the motion signal are produced, concurrently.

26. The method of claim 1, further comprising:

segmenting the heart-related signal into a plurality of windowed heart-related signal data segments and the motion signal into a corresponding plurality of windowed motion signal data segments; and repeating the reconstructing and the outputting for each windowed heart-related signal data segment and each corresponding motion signal data segment.

27. The method of claim 26, wherein the time window is a value in a range from 2 to 32 seconds.

28. The method of claim 1, wherein the biomedical sensor is at least one of: a photoplethysmogram (PPG) sensor, piezoelectric sensor, Light Emitting Diode (LED) based sensor, camera sensor, and pulse oximeter sensor, and wherein the motion sensor is an accelerometer.

29. The method of claim 1, wherein the biomedical sensor and the motion sensor are co-located.

30. The method of claim 1, further comprising employing the reconstructed representation to determine a heart rate estimate.

31. The method of claim 1, further comprising employing the reconstructed representation to determine an arterial oxygen saturation (SpO2) estimate.

32. The method of claim 1, further comprising employing the reconstructed representation to detect or predict a heart-related ailment, the heart-related ailment including at least one of a heart rate variability (HRV) condition, atrial fibrillation condition, congestive heart failure condition, and tachycardia condition.

33. The method of claim 1, wherein the reconstructing and the outputting are performed in real-time with respect to production of the heart-related signal and the motion signal.

34. The method of claim 1, wherein the reconstructing and the outputting are performed in non-real-time with respect to production of the heart-related signal and the motion signal.

35. An apparatus for reconstructing a heart-related signal output by a biomedical sensor, the apparatus comprising:

a reconstruction unit configured to reconstruct a representation of the heart-related signal to produce a reconstructed representation of the heart-related signal, the reconstructing based on (i) a time-varying spectral analysis of the heart-related signal and a motion signal, the motion signal output by a motion sensor and representative of motion artifacts in the heart-related signal, the motion artifacts being signal artifacts produced by movement of the biomedical sensor relative to a sensing location, and (ii) a classification of the movement, wherein the time-varying spectral analysis includes pre-processing the heart-related signal to produce a pre-processed heart-related signal, pre-processing the motion signal to produce a pre-processed motion signal, and computing a first time-frequency spectrum (TFS) of the heart-related signal using the pre-processed heart-related signal and a second TFS of the motion signal using the pre-processed motion signal; and an output unit configured to output the reconstructed representation of the heart-related signal.

36. The apparatus of claim 35, wherein the motion artifacts are suppressed in the reconstructed representation of the heart-related signal.

37. The apparatus of claim 35, wherein:

in an event the classification indicates that the movement does not rise to level causing the motion artifacts, the reconstructed representation is based on an average value of peak-to-peak intervals in the pre-processed heart-related signal.

38. The apparatus of claim 35, wherein the pre-processing includes filtering the heart-related signal to produce a filtered heart-related signal, the filtered heart-related signal being the pre-processed heart-related signal.

39. The apparatus of claim 38, wherein the pre-processing further includes down-sampling the filtered heart-related signal, the down-sampling being at a sampling rate less than an original sampling rate.

40. The apparatus of claim 35, wherein the first TFS computed and the second TFS computed are 3-dimensional spectra, the first TFS computed and the second TFS computed each including a respective time-varying amplitude or power distribution with respect to time and frequency.

41. The apparatus of claim 35, wherein the first TFS computed is a first time-varying power spectral density (PSD) and the second TFS computed is a second time-varying PSD.

42. The apparatus of claim 35, wherein the reconstructed representation is a current reconstructed representation and wherein, based on the classification indicating that the movement does rise to a level causing the motion artifacts and is a pseudo-periodic movement or a periodic movement, to reconstruct the representation includes:

determining whether at least one spectral peak is present having a corresponding frequency within a given frequency range at a point in time in the first TFS computed, the current reconstructed representation being reconstructed for the point in time; and wherein, based on a determination that the at least one spectral peak is not present, the reconstructed current representation is based on a prior reconstructed representation, the prior reconstructed representation associated with a previous point in time in the first TFS computed.

43. The apparatus of claim 42, wherein the given frequency range is 0.5 Hz to 3 Hz.

44. The apparatus of claim 35, wherein to reconstruct the representation includes:
retaining up to a pre-determined number of candidate spectral peaks located at a first point in time in the first TFS computed, the candidate spectral peaks retained based on having corresponding frequencies within a given frequency range and highest amplitude or power values relative to other spectral peaks located at the first point in time, the other spectral peaks having respective frequencies within the given frequency range; and
discarding each of the candidate spectral peaks retained that is associated with a same frequency as a dominant spectral peak located at a second point in time in the second TFS computed, the first point in time and the second point in time having same time values.

45. The apparatus of claim 44, wherein the given frequency range is 0.5 Hz to 3 Hz.

46. The apparatus of claim 44, wherein the representation is a current representation, wherein the reconstructed representation is a current reconstructed representation, and wherein, in an event the discarding discards each of the candidate spectral peaks retained, reconstructing the current representation is based on a prior reconstructed representation, the prior reconstructed representation associated with a previous point in time in the first TFS computed, the previous point in time being an earlier point in time with respect to the first point in time.

47. The apparatus of claim 44, wherein the discarding is a first discarding and wherein the representation is a current representation and, wherein, in an event the first discarding results in at least one remaining candidate spectral peak retained, reconstructing the current representation further includes:
second discarding, wherein the second discarding discards remaining candidate spectral peaks, of the at least one remaining candidate spectral peak retained, based on whether a corresponding frequency of the at least one remaining candidate spectral peak retained is distanced by at least a frequency difference threshold from a prior reconstructed representation's frequency, the prior reconstructed representation associated with a previous point in time in the first TFS computed, the previous point in time being an earlier point in time with respect to the first point in time.

48. The apparatus of claim 47, wherein:
based on each of the at least one remaining candidate spectral peak retained having been discarded by the second discarding, reconstructing the current representation is based on the prior reconstructed representation; and
based on at least one last candidate spectral peak remaining, the at least one last candidate spectral peak remaining not discarded by the second discarding, reconstructing the current representation is based on a selected candidate spectral peak selected from amongst the at least one last candidate spectral peak remaining having a closest corresponding frequency to the prior reconstructed representation's frequency relative to respective frequencies of each of the at least one last candidate spectral peak remaining.

49. The apparatus of claim 44, wherein the dominant spectral peak has a largest power or amplitude value relative to other peaks located at the second point in time in the second TFS.

50. The apparatus of claim 44, wherein the retaining and the discarding are based on:
the classification of the movement indicating that the movement is a pseudo-periodic movement or a periodic movement; and
determining that at least one spectral peak with a corresponding frequency in the given frequency range is present at the first point in time.

51. The apparatus of claim 35, wherein the pre-processing includes filtering the heart-related signal and the motion signal to produce a filtered heart-related signal and a filtered motion signal, respectively, the filtered heart-related signal being the pre-processed heart-related signal and the filtered motion signal being the pre-processed motion signal.

52. The apparatus of claim 51, wherein the pre-processing further includes down-sampling, at a sampling rate less than an original sampling rate, both the filtered heart-related signal and the filtered motion signal.

53. The apparatus of claim 35, further including a classification unit, the classification unit configured to:
classify the classification of the movement by comparing an amount of amplitude modulation in the second TFS computed to an amplitude modulation threshold, wherein the classification indicates whether the movement rises to a level causing the motion artifacts based on a result of the comparing.

54. The apparatus of claim 53, wherein the amplitude modulation threshold is dependent on a type of the motion detector sensor.

55. The apparatus of claim 53, wherein, in an event the result indicates that the movement does rise to the level causing the motion artifacts, the classification unit is further configured to classify the classification of the movement by determining whether the movement is either a pseudo-periodic movement or a periodic movement, versus a random movement.

56. The apparatus of claim 55, wherein to determine whether the movement is either the pseudo-periodic movement or the periodic movement versus a random movement includes:
identifying a first, second, and third frequency associated, respectively, with a first, second, and third spectral peak in the second TFS at a point in time in the second TFS, the first, second, and third peaks having largest power or amplitude values relative to other peaks in the second TFS at the point in time, the first spectral peak being a largest spectral peak amongst the first, second, and third spectral peaks;
computing a first ratio of the second frequency identified to the first frequency identified and determining a first comparison result by comparing the first ratio computed to a first ratio value; and
computing a second ratio of the third frequency identified to the first frequency identified and determining a second comparison result by comparing the second ratio computed to a second ratio value, wherein the classification further indicates that the movement is either the pseudo-periodic movement or the periodic movement, versus the random movement, based on the first comparison result and the second comparison result.

57. The apparatus of claim 56, wherein the first ratio value is 2 and the second ratio value is 3.

58. The apparatus of claim 55, wherein, in an event the classification of the movement indicates random movement, the reconstructing includes:
   computing an average value of a number of prior reconstructed representations outputted prior to the reconstructing, the number based on a duration of consecutive motion artifacts, detected prior to the reconstructing;
   computing a bandpass filter cutoff frequency based on the average value computed;
   filtering the pre-processed heart-related signal by applying the band pass filter computed to produce a filtered, pre-processed heart-related signal; and
   wherein the reconstructed representation is based on an average peak-to-peak interval value of the filtered, pre-processed heart-related signal.

59. The apparatus of claim 35, wherein the heart-related signal and the motion signal are produced, concurrently.

60. The apparatus of claim 35, further comprising segmentation unit configured to:
   segment the heart-related signal into a plurality of windowed heart-related signal data segments and the motion signal into corresponding plurality of windowed motion signal data segments, wherein the reconstruction unit and the output unit reconstruct the representation and output the reconstructed representation, respectively, based on each windowed heart-related signal data segment and each corresponding motion signal data segment.

61. The apparatus of claim 60, wherein the time window is a value in a range from 2 to 32 seconds.

62. The apparatus of claim 35, wherein the biomedical sensor is at least one of: a photoplethysmogram (PPG) sensor, piezoelectric sensor, Light Emitting Diode (LED) based sensor, camera sensor, and pulse oximeter sensor, and wherein the motion sensor is an accelerometer.

63. The apparatus of claim 35, wherein the apparatus includes the biomedical sensor and the motion sensor.

64. The apparatus of claim 35, further comprising a heart rate unit configured to employ the reconstructed representation to determine a heart rate estimate.

65. The apparatus of claim 35, further comprising an arterial oxygen saturation (SpO2) unit configured to employ the reconstructed representation to determine a SpO2 estimate.

66. The apparatus of claim 35, further comprising an ailment unit configured to employ the reconstructed representation to detect or predict a heart-related ailment, the heart-related ailment including at least one of a heart rate variability (HRV) condition, an atrial fibrillation condition, a congestive heart failure condition, and a tachycardia condition.

67. The apparatus of claim 35, wherein the reconstruction unit and the output unit are configured to reconstruct and to output, respectively, in real-time with respect to production of the heart-related signal and the motion signal.

68. The apparatus of claim 35, wherein the reconstruction unit and the output unit are configured to reconstruct and to output, respectively, in non-real-time with respect to production of the heart-related signal and the motion signal.

69. A non-transitory computer-readable medium having encoded thereon a sequence of instructions which, when loaded and executed by a processor, causes the processor to reconstruct a heart-related signal output by a biomedical sensor, the processor reconstructing the heart-related signal by:
   reconstructing a representation of the heart-related signal to produce a reconstructed representation of the heart-related signal, the reconstructing based on (i) a time-varying spectral analysis of the heart-related signal and a motion signal, the motion signal output by a motion sensor and representative of motion artifacts in the heart-related signal, the motion artifacts being signal artifacts produced by movement of the biomedical sensor relative to a sensing location, and (ii) a classification of the movement, wherein the time-varying spectral analysis includes pre-processing the heart-related signal to produce a pre-processed heart-related signal, pre-processing the motion signal to produce a pre-processed motion signal, and computing a first time-frequency spectrum (TFS) of the heart-related signal using the pre-processed heart-related signal and a second TFS of the motion signal using the pre-processed motion signal; and
   outputting the reconstructed representation of the heart-related signal.

70. A method for reconstructing a heart-related signal output by a biomedical sensor, the method comprising:
   reconstructing a representation of the heart-related signal to produce a reconstructed representation of the heart-related signal, the reconstructing based on (i) a time-varying spectral analysis of the heart-related signal and a motion signal, the motion signal output by a motion sensor and representative of motion artifacts in the heart-related signal, the motion artifacts being signal artifacts produced by movement of the biomedical sensor relative to a sensing location, and (ii) a classification of the movement, wherein the time-varying spectral analysis includes computing a first time-frequency spectrum (TFS) of the heart-related signal and computing a second TFS of the motion signal; and
   outputting the reconstructed representation of the heart-related signal, wherein the reconstructed representation is a current reconstructed representation and wherein, based on the classification indicating that the movement does rise to a level causing the motion artifacts and is a pseudo-periodic movement or a periodic movement, the reconstructing includes:
   determining whether at least one spectral peak is present having a corresponding frequency within a given frequency range at a point in time in the first TFS computed, the current reconstructed representation being reconstructed for the point in time; and
   wherein, based on a determination that the at least one spectral peak is not present, the current reconstructed representation is based on a prior reconstructed representation, the prior reconstructed representation associated with a previous point in time in the first TFS computed.

71. A method for reconstructing a heart-related signal output by a biomedical sensor, the method comprising:
   reconstructing a representation of the heart-related signal to produce a reconstructed representation of the heart-related signal, the reconstructing based on (i) a time-varying spectral analysis of the heart-related signal and a motion signal, the motion signal output by a motion sensor and representative of motion artifacts in the heart-related signal, the motion artifacts being signal artifacts produced by movement of the biomedical sensor relative to a sensing location, and (ii) a classification of the movement, wherein the time-varying spectral analysis includes computing a first time-frequency spectrum (TFS) of the heart-related signal and computing a second TFS of the motion signal; and outputting the reconstructed representation of the heart-related signal, wherein the reconstructing includes:

retaining up to a pre-determined number of candidate spectral peaks located at a first point in time in the first TFS computed, the candidate spectral peaks retained based on having corresponding frequencies within a given frequency range and highest amplitude or power values relative to other spectral peaks located at the first point in time, the other spectral peaks having respective frequencies within the given frequency range; and discarding each of the candidate spectral peaks retained that is associated with a same frequency as a dominant spectral peak located at a second point in time in the second TFS computed, the first point in time and the second point in time having same time values.

72. A method for reconstructing a heart-related signal output by a biomedical sensor, the method comprising:

reconstructing a representation of the heart-related signal to produce a reconstructed representation of the heart-related signal, the reconstructing based on (i) a time-varying spectral analysis of the heart-related signal and a motion signal, the motion signal output by a motion sensor and representative of motion artifacts in the heart-related signal, the motion artifacts being signal artifacts produced by movement of the biomedical sensor relative to a sensing location, and (ii) a classification of the movement, wherein the time-varying spectral analysis includes computing a first time-frequency spectrum (TFS) of the heart-related signal and computing a second TFS of the motion signal;

classifying the classification of the movement by comparing an amount of amplitude modulation in the second TFS computed to an amplitude modulation threshold, wherein the classification indicates whether the movement rises to a level of causing the motion artifacts based on a result of the comparing; and outputting the reconstructed representation of the heart-related signal.

73. An apparatus for reconstructing a heart-related signal output by a biomedical sensor, the apparatus comprising:

a reconstruction unit configured to reconstruct a representation of the heart-related signal to produce a reconstructed representation of the heart-related signal, the reconstructing based on (i) a time-varying spectral analysis of the heart-related signal and a motion signal, the motion signal output by a motion sensor and representative of motion artifacts in the heart-related signal, the motion artifacts being signal artifacts produced by movement of the biomedical sensor relative to a sensing location, and (ii) a classification of the movement, wherein the time-varying spectral analysis includes computing a first time-frequency spectrum (TFS) of the heart-related signal and computing a second TFS of the motion signal; and an output unit configured to output the reconstructed representation of the heart-related signal, wherein the reconstructed representation is a current reconstructed representation and wherein, based on the classification indicating that the movement does rise to a level causing the motion artifacts and is a pseudo-periodic movement or a periodic movement, to reconstruct the representation includes:

determining whether at least one spectral peak is present having a corresponding frequency within a given frequency range at a point in time in the first TFS computed, the current reconstructed representation being reconstructed for the point in time; and wherein, based on a determination that the at least one spectral peak is not present, the reconstructed current representation is based on a prior reconstructed representation, the prior reconstructed representation associated with a previous point in time in the first TFS computed.

74. An apparatus for reconstructing a heart-related signal output by a biomedical sensor, the apparatus comprising:

a reconstruction unit configured to reconstruct a representation of the heart-related signal to produce a reconstructed representation of the heart-related signal, the reconstructing based on (i) a time-varying spectral analysis of the heart-related signal and a motion signal, the motion signal output by a motion sensor and representative of motion artifacts in the heart-related signal, the motion artifacts being signal artifacts produced by movement of the biomedical sensor relative to a sensing location, and (ii) a classification of the movement, wherein the time-varying spectral analysis includes computing a first time-frequency spectrum (TFS) of the heart-related signal and computing a second TFS of the motion signal; and an output unit configured to output the reconstructed representation of the heart-related signal, wherein to reconstruct the representation includes:

retaining up to a pre-determined number of candidate spectral peaks located at a first point in time in the first TFS computed, the candidate spectral peaks retained based on having corresponding frequencies within a given frequency range and highest amplitude or power values relative to other spectral peaks located at the first point in time, the other spectral peaks having respective frequencies within the given frequency range; and discarding each of the candidate spectral peaks retained that is associated with a same frequency as a dominant spectral peak located at a second point in time in the second TFS computed, the first point in time and the second point in time having same time values.

75. An apparatus for reconstructing a heart-related signal output by a biomedical sensor, the apparatus comprising:

a reconstruction unit configured to reconstruct a representation of the heart-related signal to produce a reconstructed representation of the heart-related signal, the reconstructing based on (i) a time-varying spectral analysis of the heart-related signal and a motion signal, the motion signal output by a motion sensor and representative of motion artifacts in the heart-related signal, the motion artifacts being signal artifacts produced by movement of the biomedical sensor relative to a sensing location, and (ii) a classification of the movement, wherein the time-varying spectral analysis includes computing a first time-frequency spectrum (TFS) of the heart-related signal and computing a second TFS of the motion signal;

a classification unit configured to classify the classification of the movement by comparing an amount of amplitude modulation in the second TFS computed to an amplitude modulation threshold, wherein the classification indicates whether the movement rises to a level causing the motion artifacts based on a result of the comparing; and an output unit configured to output the reconstructed representation of the heart-related signal.

* * * * *